US012653891B2

(12) United States Patent
Deisher et al.

(10) Patent No.: US 12,653,891 B2
(45) Date of Patent: Jun. 16, 2026

(54) STABLE GLUCOCORTICOID FORMULATION

(71) Applicant: AVM Biotechnology, LLC, Seattle, WA (US)

(72) Inventors: Theresa Deisher, Seattle, WA (US); Adalbert Jarzyna, Seattle, WA (US); Iain Duncan, Seattle, WA (US)

(73) Assignee: AVM Biotechnology, LLC, Seattle, WA (US)

( * ) Notice: Subject to any disclaimer, the term of this patent is extended or adjusted under 35 U.S.C. 154(b) by 678 days.

(21) Appl. No.: 16/885,815

(22) Filed: May 28, 2020

(65) Prior Publication Data

US 2020/0289650 A1 Sep. 17, 2020

Related U.S. Application Data

(63) Continuation of application No. PCT/US2019/061363, filed on Nov. 14, 2019.

(60) Provisional application No. 62/767,448, filed on Nov. 14, 2018.

(51) Int. Cl.
*A61K 47/02* (2006.01)
*A61K 31/573* (2006.01)
*A61K 47/18* (2017.01)

(52) U.S. Cl.
CPC ............ *A61K 47/02* (2013.01); *A61K 31/573* (2013.01); *A61K 47/183* (2013.01)

(58) Field of Classification Search
CPC ..... A61K 31/573; A61K 47/02; A61K 47/183
See application file for complete search history.

(56) References Cited

U.S. PATENT DOCUMENTS

| | | | | |
|---|---|---|---|---|
| 9,512,200 | B2 | 12/2016 | Deisher | |
| 9,962,408 | B2 | 5/2018 | Deisher | |
| 10,030,230 | B2 | 7/2018 | Deisher | |
| 10,426,740 | B1 | 10/2019 | Deisher | |
| 2004/0197333 | A1* | 10/2004 | Suthanthiran | C07K 16/22 424/145.1 |
| 2005/0281861 | A1* | 12/2005 | Hughes | A61K 47/34 424/145.1 |
| 2008/0038316 | A1* | 2/2008 | Wong | A61P 31/00 514/169 |
| 2011/0195988 | A1* | 8/2011 | Alan March | A61K 31/485 514/282 |
| 2013/0243862 | A1* | 9/2013 | Alferiev | A61L 27/50 435/235.1 |
| 2018/0296572 | A1 | 10/2018 | Deisher | |
| 2020/0108078 | A1 | 4/2020 | Deisher | |

FOREIGN PATENT DOCUMENTS

| | | | |
|---|---|---|---|
| AU | 2013000089 | * | 1/2013 |
| AU | 2013/200089 | * | 2/2013 |
| CN | 101623291 | A | 1/2010 |
| EP | 2995298 | A1 | 3/2016 |
| EP | 3488851 | A1 | 5/2019 |
| JP | 2006136490 | A | 6/2006 |
| JP | 2011136973 | | 7/2011 |
| JP | 2014207983 | A | 11/2014 |
| KR | 20080080387 | A | 9/2008 |
| WO | 9940430 | A2 | 8/1999 |
| WO | 2009099641 | A2 | 8/2009 |
| WO | 2010054356 | A1 | 5/2010 |
| WO | 2017097432 | A1 | 6/2017 |
| WO | WO 2018/183927 | * | 4/2018 |
| WO | 2018183927 | A1 | 10/2018 |
| WO | 2020072713 | A1 | 4/2020 |

OTHER PUBLICATIONS

SOLCORT Intravenous Injection prescription (Jun. 2011, Japanese Version). (Year: 2011).*
SOLCORT Intravenous Injection prescription (Jun. 2011, partial English translation). (Year: 2011).*
SOLCORT Intravenous Injection prescription (Jun. 2011). (Year: 2011).*
Michiels et al. Applied Sciences (2017) 7:1-30 (Year: 2017).*
Jaime et al., Journal of Drug Delivery Science and Technology (2022) 71:1-9 (Year: 2022).*
Communication from International Bureau issued in International Application No. PCT/US2019/061363 dated Apr. 22, 2020, acknowledging receipt of Informal Comments filed by Applicant in International Application No. PCT/US2019/061363 on Apr. 21, 2020 (5 pages).
Haynes et al., "Intratympanic Dexamethasone for Sudden Sensorineural Hearing Loss After Failure of Systemic Therapy," The Laryngoscope 117(1):3-15 (2007).
Hughes et al., "Dexamethasone Otoprotection in a Multidose Cisplatin Ototoxicity Mouse Model," Otology and Neurotology 150(1):115-120 (2013).
International Search Report and Written Opinion issued in International Application No. PCT/US2019/061363, mailed Feb. 13, 2020, 17 pages.
Ministry of Health, Labour and Welfare: Pharmaceuticals and Medical Devices Safety Information No. 219, pp. 1-20, Retrieved from the Internet: URL:https://www.pmda.go.jp/files/000153438.pdf (2005).
Li et al., "Mechanism of base-catalyzed autooxidation of corticosteroids containing 20-keto-21-hydroxyl side chain," Tetrahedron Letters 50(32):4575-4581 (2009), Abstract only.
Alexander et al., "Dose Effect of Intratympanic Dexamethasone for Idiopathic Sudden Sensorineural Hearing Loss: 24 mg/mL Is Superior to 10 mg/mL," Otology and Neurotology 36:1321-1327 (2015).
Cao, Xiaochen, "Study on Impurities and Preparation Process of Dexamethasone Sodium Phosphate Injection," China Doctoral/Master High Quality Dissertation Full-text Database (Master), Medicine & Public Health, E079-33 (2014).
English translation of Notice of Reasons for Rejection issued in Japanese Application No. 2020-529561, mailed Jul. 5, 2022, 2 pages.

(Continued)

*Primary Examiner* — Marcos L Sznaidman
(74) *Attorney, Agent, or Firm* — McNeill PLLC

(57) ABSTRACT

This invention relates to aqueous pharmaceutical formulations comprising a glucocorticoid. These have been formulated to contain high concentrations of glucocorticoid and reduced levels of preservatives.

17 Claims, 31 Drawing Sheets

(56) References Cited

OTHER PUBLICATIONS

English translation of Notification of the Second Office Action issued in Chinese Application No. 201980007393.X, mailed Jul. 1, 2022, 7 pages.
Pharmaceutical Product Interview Form, SOLCORT intravenous solution 100 mg, 17 pages (2011).
"Allowable Excess Volume and Labeled Vial Fill Size in Injectable Drug and Biological Products: Guidance for Industry," U.S. Department of Health and Human Services Food and Drug Administration Center for Drug Evaluation and Research (CDER) Center for Biologics Evaluation and Research (CBER), Jun. 2015 Pharmaceutical Quality/CMC, 8 pages.
"Guidance for Industry: Q1D Bracketing and Matrixing Designs for Stability Testing of New Drug Substances and Products," U.S. Department of Health and Human Services, Food and Drug Administration, Center for Drug Evaluation and Research (CDER), Center for Biologics Evaluation and Research (CBER), Jan. 2003, 11 pages.
Certificate of Analysis—Certified Reference Material: Polyethylene Glycol 300, www.signmaaldrich.com, 5 pages, issued 2023.
Dasnoy et al., "A Predictive Modeling Approach to Support the Overfill Volume Definition of Liquid-in-Vial Drug Products," PDA J Pharm Sci and Tech 76:384-394 (2022).
PubChem Compound Summary for CID 5743, Dexamethasone; Available from: https://pubchem.ncbi.nlm.nih.gov/compound/Dexamethasone (last accessed Mar. 2024).
Rushton et al., "Key Role for Efflux in the Preservative Susceptibility and Adaptive Resistance of Burkholderia cepacia Complex Bacteria," Antimicrobial Agents and Chemotherapy, 57(7), p. 2972-2980 (2013).
Technical Data Sheet, CAS No. 25322-68-3, CARPOL PEG-400, Polyethylene Glycol, 1 page, Updated May 2015.
USP-NF General Chapter <1151> Pharmaceutical Dosage Forms, https://doi.org/10.31003/USPNF_M99860_08_01, 27 pages (2021) (last accessed Mar. 2024).
Yang et al., "Toxicity of benzethonium chloride and polyhexamethylene guanidine hydrochloride mixtures on Daphnia carinata: synergistic and antagonistic effects at specific ratios," Ecotoxicology and Environmental Safety 263 (2023) 115268, 8 pages.
Zhao et al., "Benzalkonium Chloride and Benzethonium Chloride Effectively Reduce Spore Germination of Ginger Soft Rot Pathogens: Fusarium solani and Fusarium oxysporum," Journal of Fungi 2024, 10(8), 15 pages.
Jaime et al., "Moisture and oxygen barrier properties of glass, PET and HDPE bottles for pharmaceutical products," Journal of Drug Delivery Science and Technology 71 103330, 9 pages (2022).
Michiels et al., "Barriers and Chemistry in a Bottle: Mechanisms in Today's Oxygen Barriers for Tomorrow's Materials," Appl. Sci. 7(665): 1-30 (2017).
Cholayudth et al., "Establishing Target Fills for Semisolid and Liquid Dosage Forms," Pharmaceutical Technology 142-152 (2005).
Lighthouse E-Book, "Manufacturing Sterile Parenteral Pharmaceuticals: How to Protect Oxygen Sensitive Formulations," 13 pages, available at https://www.pharmaceuticalonline.com/doc/manufacturing-sterile-parenteral-pharmaceuticals-how-to-protect-oxygen-sensitive-formulations-0001 (2021).
Ruesch et al., "Strategies for Setting Patient-Centric Commercial Specifications for Biotherapeutic Products," Journal of Pharmaceutical Sciences 110:771-784 (2021).
"Handbook of Pharmaceutical Manufacturing Formulations: Sterile Products" vol. 6, retrieved from the internet Jan. 29, 2025 https://www.taylorfrancis.com/chapters/mono/10.3109/9781420081312-17/approved-excipients-sterile-dosage-forms-safaraz-niaz (2 pages).
SCOGS (Select Committee on GRAS Substances), FDA database, retrieved from the internet Jan. 28, 2025, https://www.hfpappexternal.fda.gov/scripts/fdcc/index.cfm?set=SCOGS&sort=Sortsubstance&order=ASC&startrow=1&type=basic&search=benzethonium%20chloride, 3 pages.
Benzethonium chloride, Meyler's Side Effects of Drugs (16th Edition), 2016, retrieved from the internet Jan. 29, 2025, https://www.sciencedirect.com/topics/pharmacology-toxicology-and-pharmaceutical-science/benzethonium- chloride, 10 pages.
Civen et al., "Outbreak of Serratia marcescens Infections following Injection of Betamethasone Compounded at a Community Pharmacy," Clinical Infectious Diseases 43:831-837 (2006).
United States Pharmacopeia, Pharmaceutical Compounding—Sterile Preparations, obtained from the internet: https://www.usp.org/compounding/general-chapter-797, 56 pages (2021).
Qureshi et al., "Sterile Compounding: Clinical, Legal, and Regulatory Implications for Patient Safety," J. Managed Care & Specialty Pharm. 20(12):1183-91 (2014).

* cited by examiner

*Figure 5*
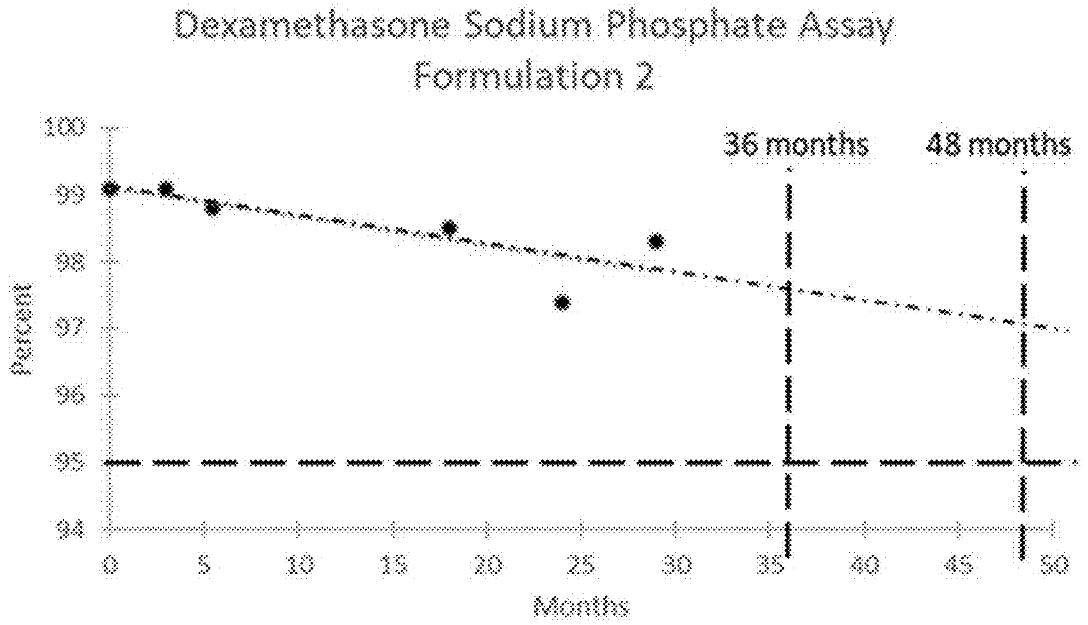
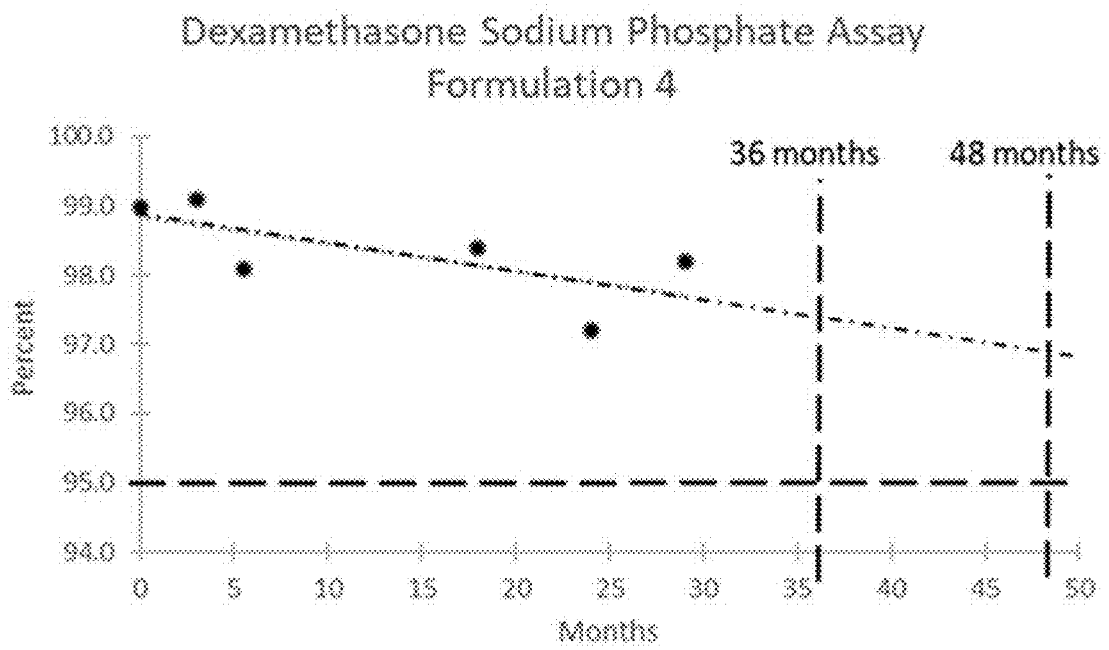

Figure 27

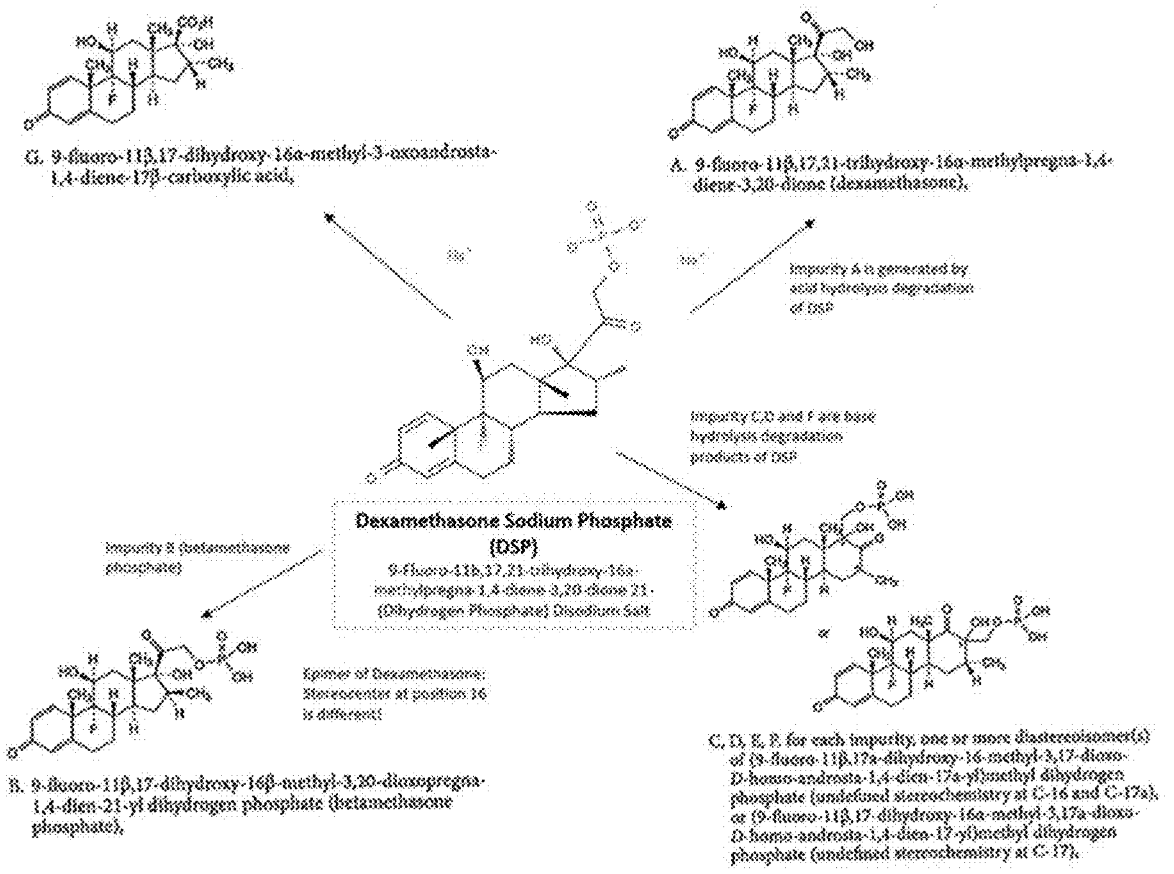

G. 9-fluoro-11β,17-dihydroxy-16α-methyl-3-oxoandrosta-1,4-diene-17β-carboxylic acid, A. 9-fluoro-11β,17,21-trihydroxy-16α-methylpregna-1,4-diene-3,20-dione (dexamethasone), B. 9-fluoro-11β,17-dihydroxy-16β-methyl-3,20-dioxopregna-1,4-dien-21-yl dihydrogen phosphate (betamethasone phosphate), C, D, E, F. for each impurity, one or more diastereoisomer(s) of (9-fluoro-11β,17a-dihydroxy-16-methyl-3,17-dioxo-D-homo-androsta-1,4-dien-17a-yl)methyl dihydrogen phosphate (undefined stereochemistry at C-16 and C-17a), or (9-fluoro-11β,17-dihydroxy-16α-methyl-3,17a-dioxo-D-homo-androsta-1,4-dien-17-yl)methyl dihydrogen phosphate (undefined stereochemistry at C-17).

| | Equivalent USP Impurity |
|---|---|
| Impurity A | Dexamethasone |
| Impurity B | Betamethasone sodium phosphate |
| Impurity C | USP Impurity a |
| Impurity D | USP Impurity b |
| Impurity E | USP Impurity c |
| Impurity F | USP Impurity d |
| Impurity G | USP Impurity f |

*Figure 28*

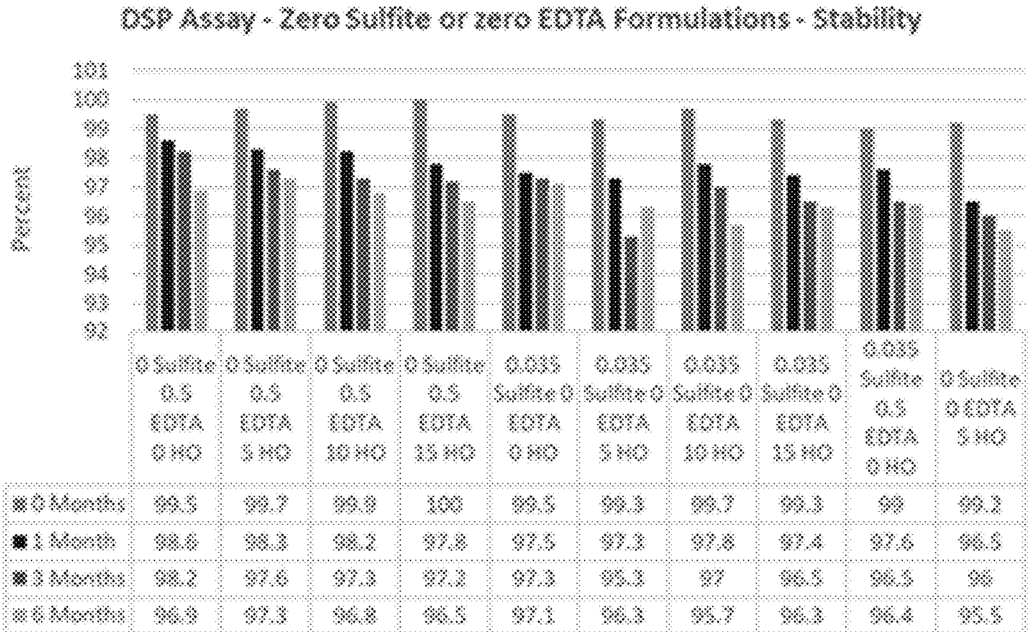

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 99.5 | 99.7 | 99.9 | 100 | 99.5 | 99.3 | 99.7 | 99.3 | 99 | 99.2 |
| 1 Month | 98.6 | 98.3 | 98.2 | 97.8 | 97.5 | 97.3 | 97.8 | 97.4 | 97.6 | 96.5 |
| 3 Months | 98.2 | 97.6 | 97.3 | 97.2 | 97.3 | 95.3 | 97 | 96.5 | 96.5 | 96 |
| 6 Months | 96.9 | 97.3 | 96.8 | 96.5 | 97.1 | 96.3 | 95.7 | 96.3 | 96.4 | 95.5 |

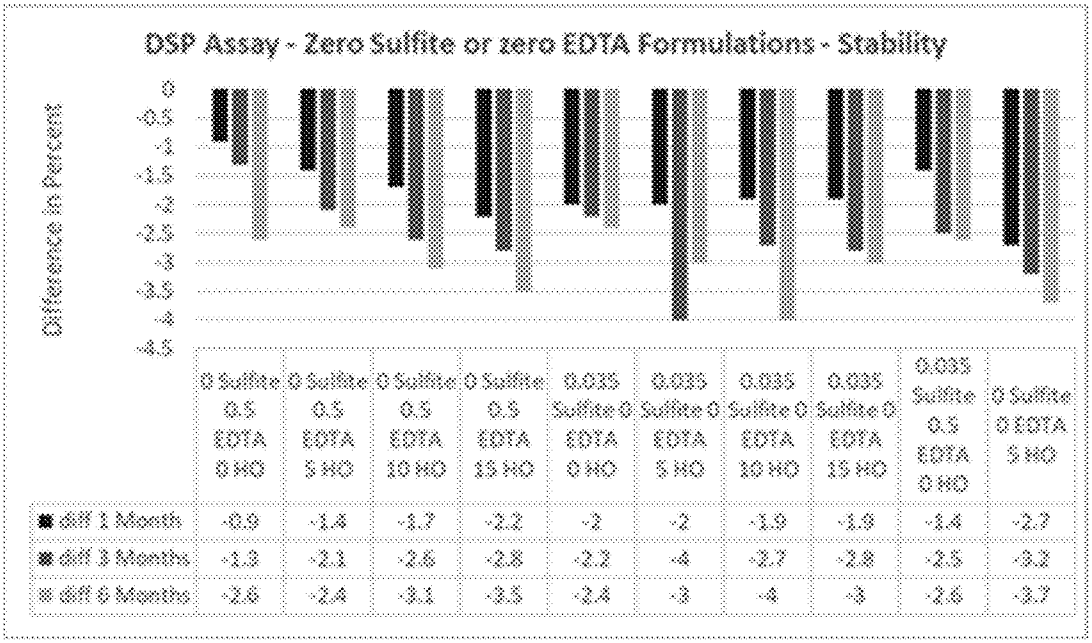

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| diff 1 Month | -0.9 | -1.4 | -1.7 | -2.2 | -2 | -2 | -1.9 | -1.9 | -1.4 | -2.7 |
| diff 3 Months | -1.3 | -2.1 | -2.6 | -2.8 | -2.2 | -4 | -2.7 | -2.8 | -2.5 | -3.2 |
| diff 6 Months | -2.6 | -2.4 | -3.1 | -3.5 | -2.4 | -3 | -4 | -3 | -2.6 | -3.7 |

Figure 29

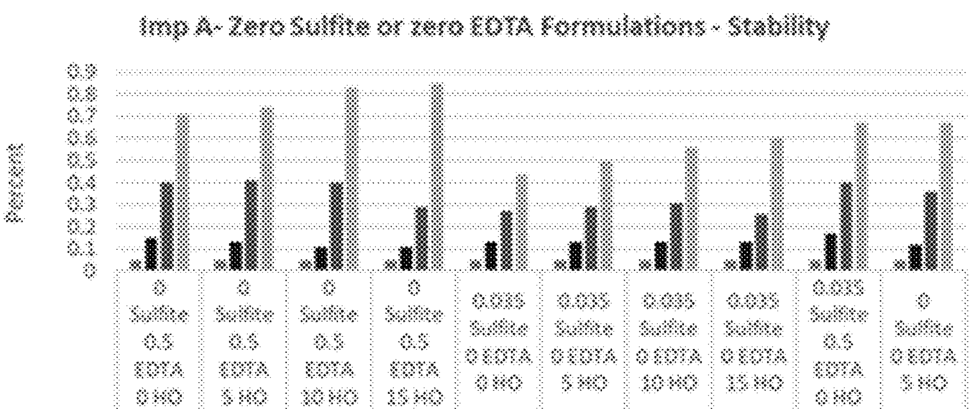

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.049 | 0.049 | 0.049 | 0.049 | 0.049 | 0.049 | 0.049 | 0.049 | 0.049 | 0.049 |
| 1 Month | 0.15 | 0.13 | 0.11 | 0.11 | 0.13 | 0.13 | 0.13 | 0.13 | 0.17 | 0.12 |
| 3 Months | 0.4 | 0.41 | 0.4 | 0.29 | 0.27 | 0.29 | 0.31 | 0.26 | 0.4 | 0.36 |
| 6 Months | 0.71 | 0.74 | 0.83 | 0.85 | 0.44 | 0.5 | 0.56 | 0.6 | 0.67 | 0.67 |

Figure 30

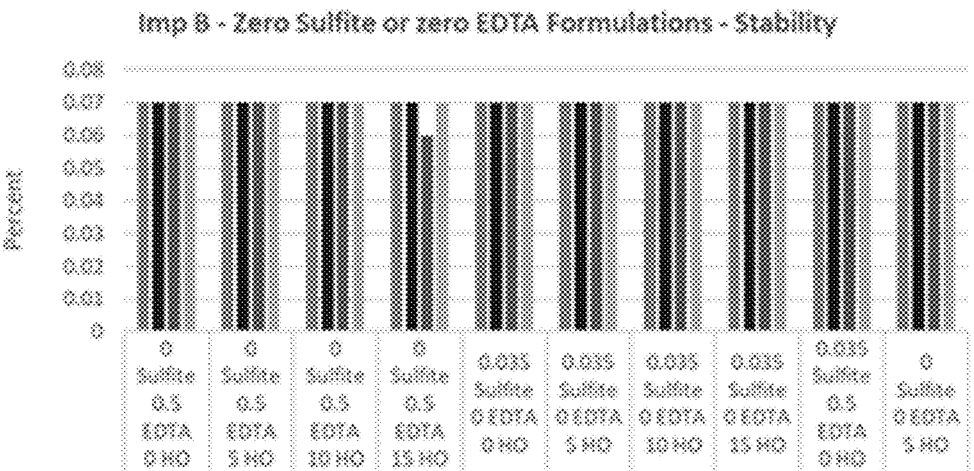

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.07 | 0.07 | 0.07 | 0.07 | 0.07 | 0.07 | 0.07 | 0.07 | 0.07 | 0.07 |
| 1 Month | 0.07 | 0.07 | 0.07 | 0.07 | 0.07 | 0.07 | 0.07 | 0.07 | 0.07 | 0.07 |
| 3 Months | 0.07 | 0.07 | 0.07 | 0.06 | 0.07 | 0.07 | 0.07 | 0.07 | 0.07 | 0.07 |
| 6 Months | 0.07 | 0.07 | 0.07 | 0.07 | 0.07 | 0.07 | 0.07 | 0.07 | 0.07 | 0.07 |

Figure 31

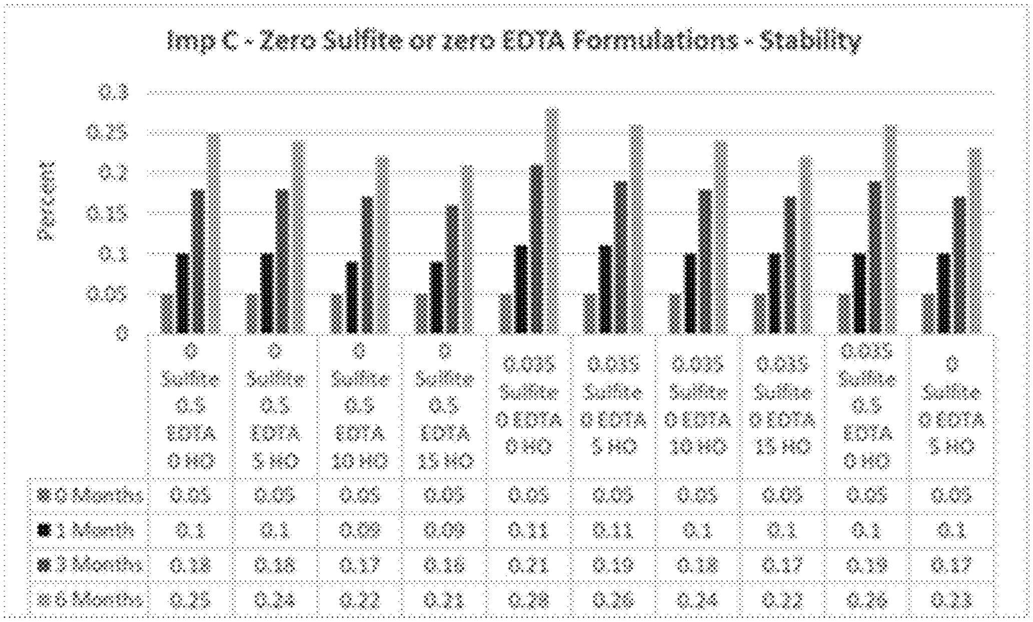

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.05 | 0.05 | 0.05 | 0.05 | 0.05 | 0.05 | 0.05 | 0.05 | 0.05 | 0.05 |
| 1 Month | 0.1 | 0.1 | 0.09 | 0.09 | 0.11 | 0.11 | 0.1 | 0.1 | 0.1 | 0.1 |
| 3 Months | 0.18 | 0.18 | 0.17 | 0.16 | 0.21 | 0.19 | 0.18 | 0.17 | 0.19 | 0.17 |
| 6 Months | 0.25 | 0.24 | 0.22 | 0.21 | 0.28 | 0.26 | 0.24 | 0.22 | 0.26 | 0.23 |

Figure 32

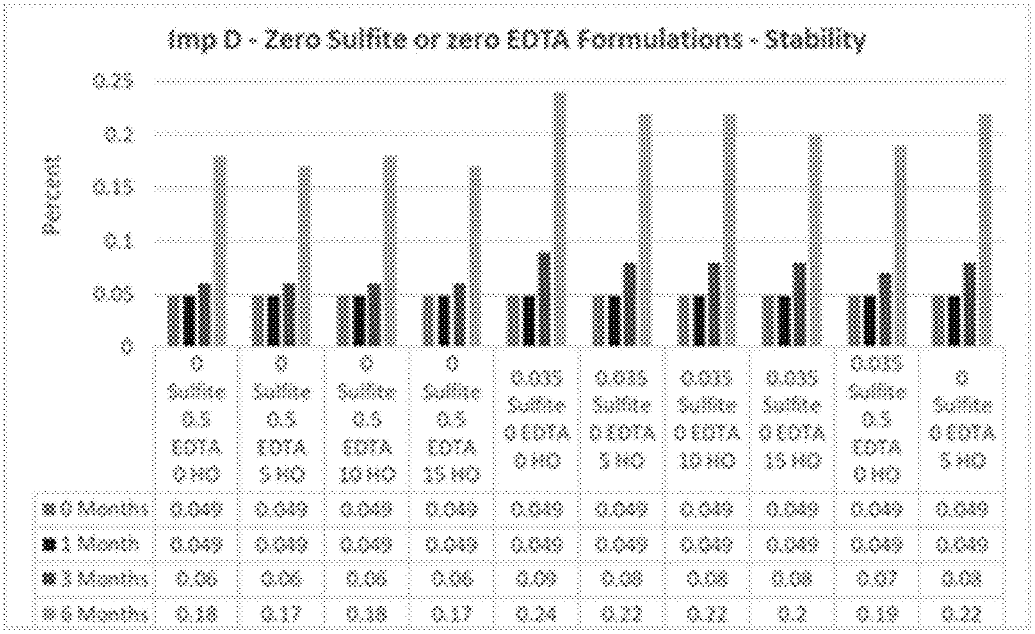

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.049 | 0.049 | 0.049 | 0.049 | 0.049 | 0.049 | 0.049 | 0.049 | 0.049 | 0.049 |
| 1 Month | 0.049 | 0.049 | 0.049 | 0.049 | 0.049 | 0.049 | 0.049 | 0.049 | 0.049 | 0.049 |
| 3 Months | 0.06 | 0.06 | 0.06 | 0.06 | 0.09 | 0.08 | 0.08 | 0.08 | 0.07 | 0.08 |
| 6 Months | 0.18 | 0.17 | 0.18 | 0.17 | 0.24 | 0.22 | 0.22 | 0.2 | 0.19 | 0.22 |

Figure 33

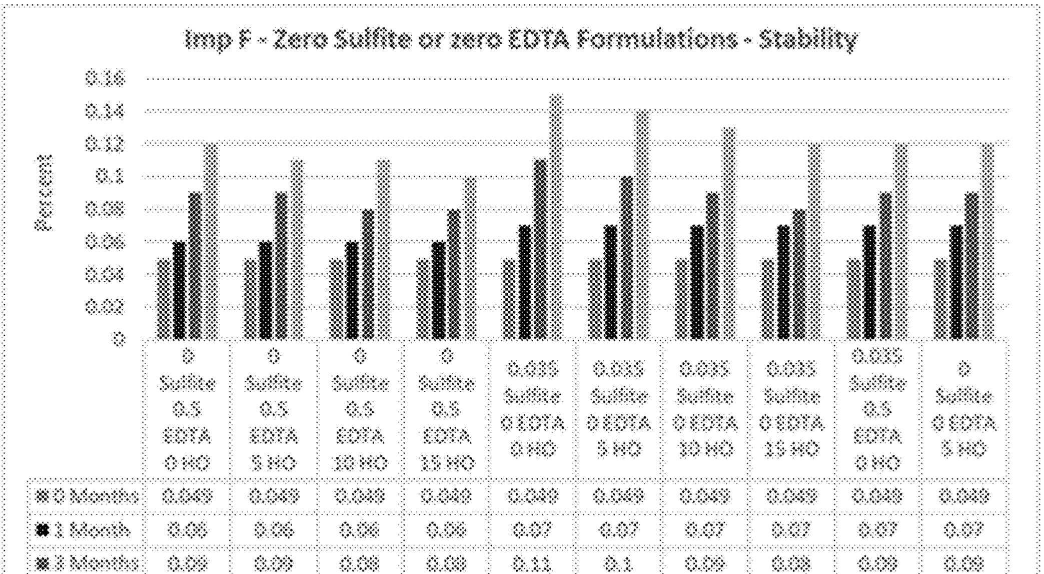

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.049 | 0.049 | 0.049 | 0.049 | 0.049 | 0.049 | 0.049 | 0.049 | 0.049 | 0.049 |
| 1 Month | 0.06 | 0.06 | 0.06 | 0.06 | 0.07 | 0.07 | 0.07 | 0.07 | 0.07 | 0.07 |
| 3 Months | 0.09 | 0.09 | 0.08 | 0.08 | 0.11 | 0.1 | 0.09 | 0.08 | 0.09 | 0.09 |
| 6 Months | 0.12 | 0.11 | 0.11 | 0.1 | 0.15 | 0.14 | 0.13 | 0.12 | 0.12 | 0.12 |

Figure 34

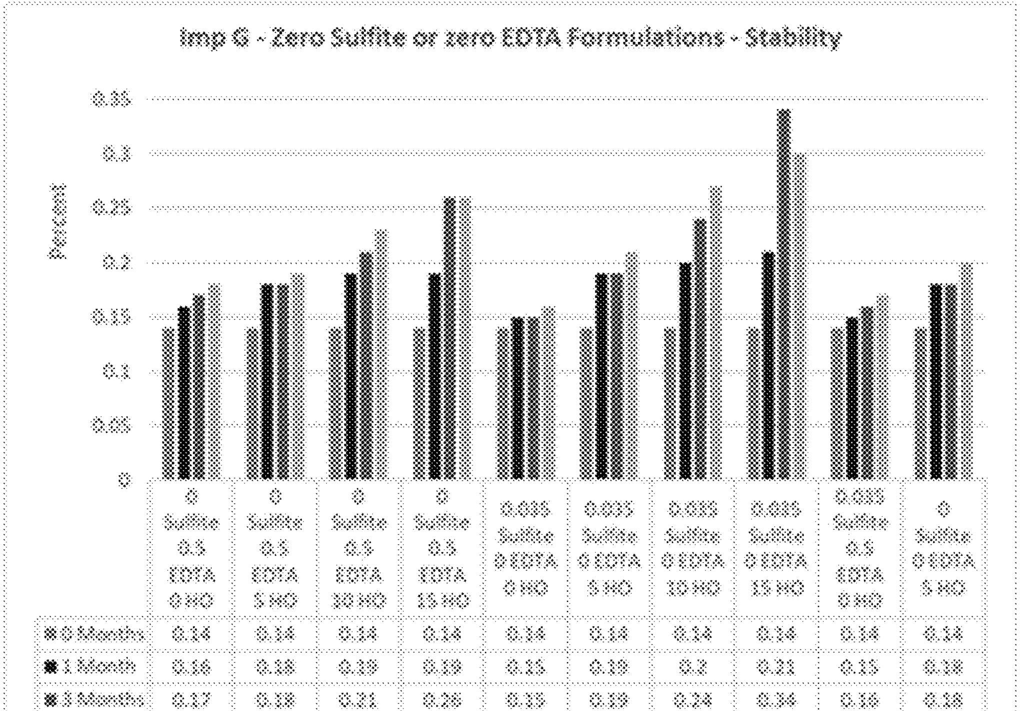

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.14 | 0.14 | 0.14 | 0.14 | 0.14 | 0.14 | 0.14 | 0.14 | 0.14 | 0.14 |
| 1 Month | 0.16 | 0.18 | 0.19 | 0.19 | 0.15 | 0.19 | 0.2 | 0.21 | 0.15 | 0.18 |
| 3 Months | 0.17 | 0.18 | 0.21 | 0.26 | 0.15 | 0.19 | 0.24 | 0.34 | 0.16 | 0.18 |
| 6 Months | 0.18 | 0.19 | 0.23 | 0.26 | 0.16 | 0.21 | 0.27 | 0.3 | 0.17 | 0.2 |

*Figure 35*

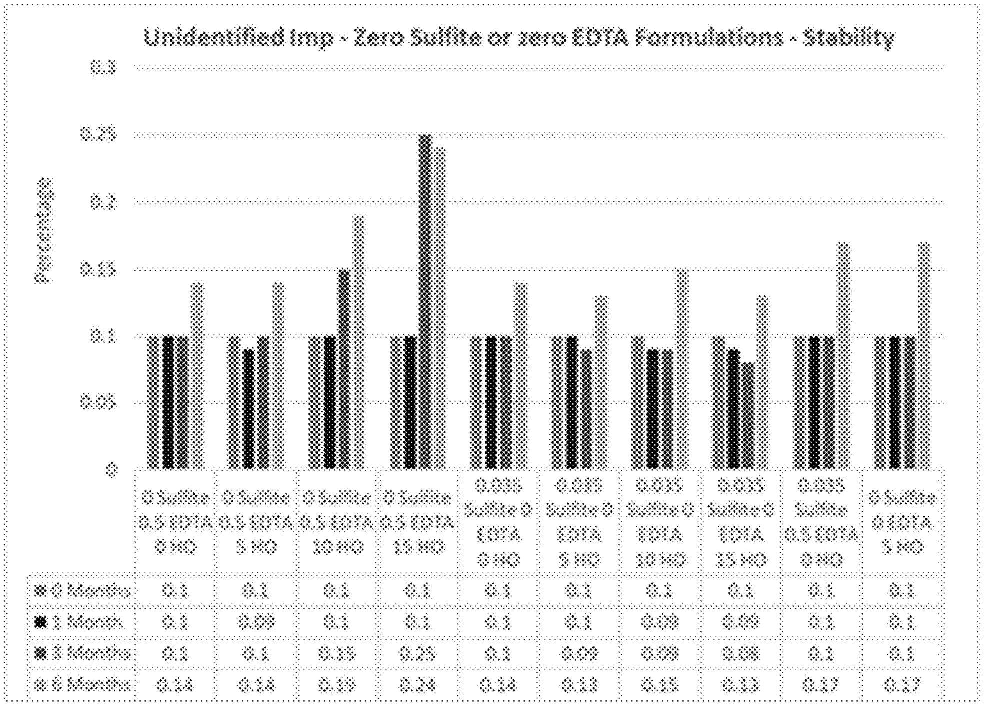

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.1 | 0.1 | 0.1 | 0.1 | 0.1 | 0.1 | 0.1 | 0.1 | 0.1 | 0.1 |
| 1 Month | 0.1 | 0.09 | 0.1 | 0.1 | 0.1 | 0.1 | 0.09 | 0.09 | 0.1 | 0.1 |
| 3 Months | 0.1 | 0.1 | 0.15 | 0.25 | 0.1 | 0.09 | 0.09 | 0.08 | 0.1 | 0.1 |
| 6 Months | 0.14 | 0.14 | 0.19 | 0.24 | 0.14 | 0.13 | 0.15 | 0.13 | 0.17 | 0.17 |

*Figure 36*

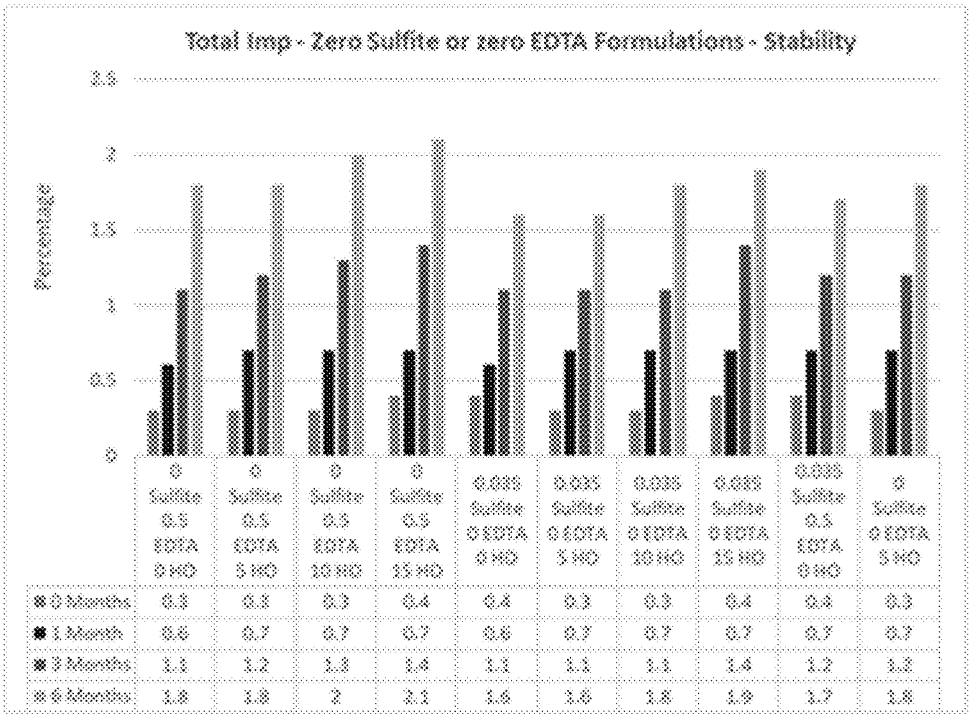

| | 0 Sulfite 0.5 EDTA 0 HO | 0 Sulfite 0.5 EDTA 5 HO | 0 Sulfite 0.5 EDTA 10 HO | 0 Sulfite 0.5 EDTA 15 HO | 0.035 Sulfite 0 EDTA 0 HO | 0.035 Sulfite 0 EDTA 5 HO | 0.035 Sulfite 0 EDTA 10 HO | 0.035 Sulfite 0 EDTA 15 HO | 0.035 Sulfite 0.5 EDTA 0 HO | 0 Sulfite 0 EDTA 5 HO |
|---|---|---|---|---|---|---|---|---|---|---|
| 0 Months | 0.3 | 0.3 | 0.3 | 0.4 | 0.4 | 0.3 | 0.3 | 0.4 | 0.4 | 0.3 |
| 1 Month | 0.6 | 0.7 | 0.7 | 0.7 | 0.6 | 0.7 | 0.7 | 0.7 | 0.7 | 0.7 |
| 3 Months | 1.1 | 1.2 | 1.3 | 1.4 | 1.1 | 1.1 | 1.1 | 1.4 | 1.2 | 1.2 |
| 6 Months | 1.8 | 1.8 | 2 | 2.1 | 1.6 | 1.6 | 1.8 | 1.9 | 1.7 | 1.8 |

*Figure 43*
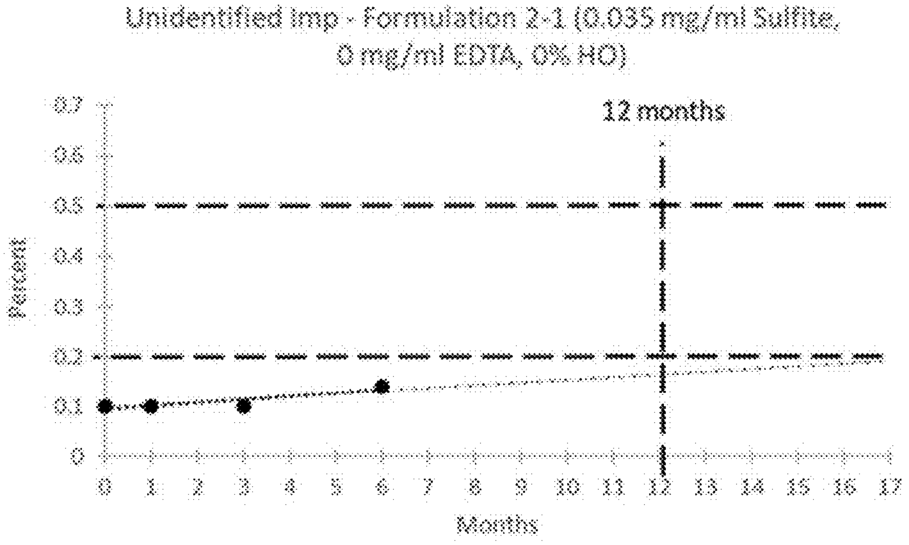
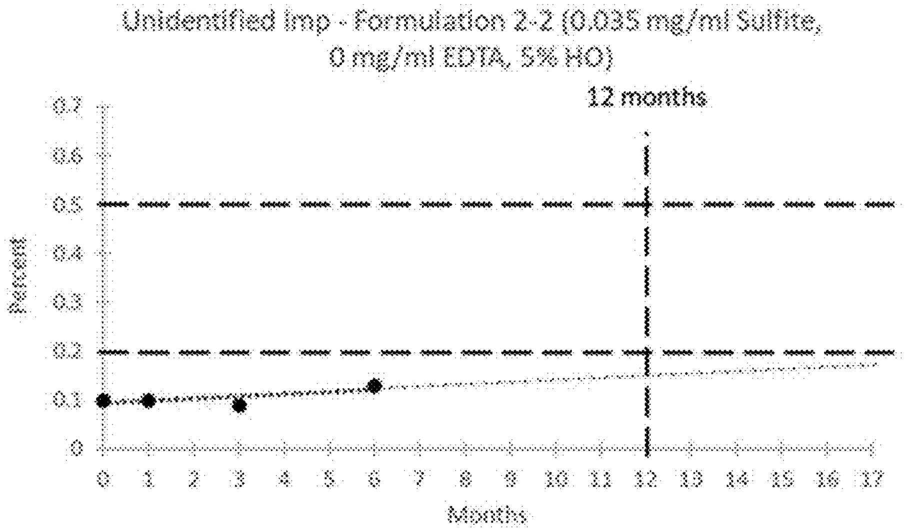
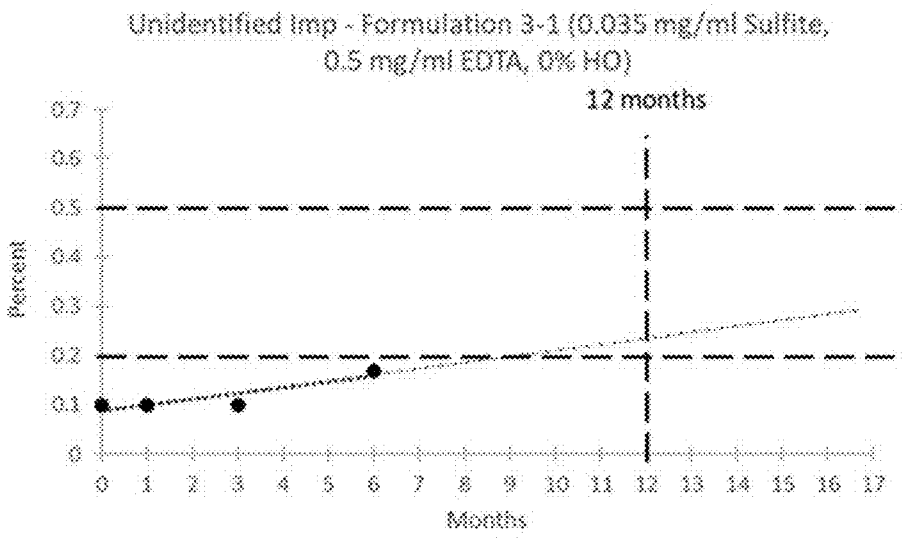

*Figure 45*
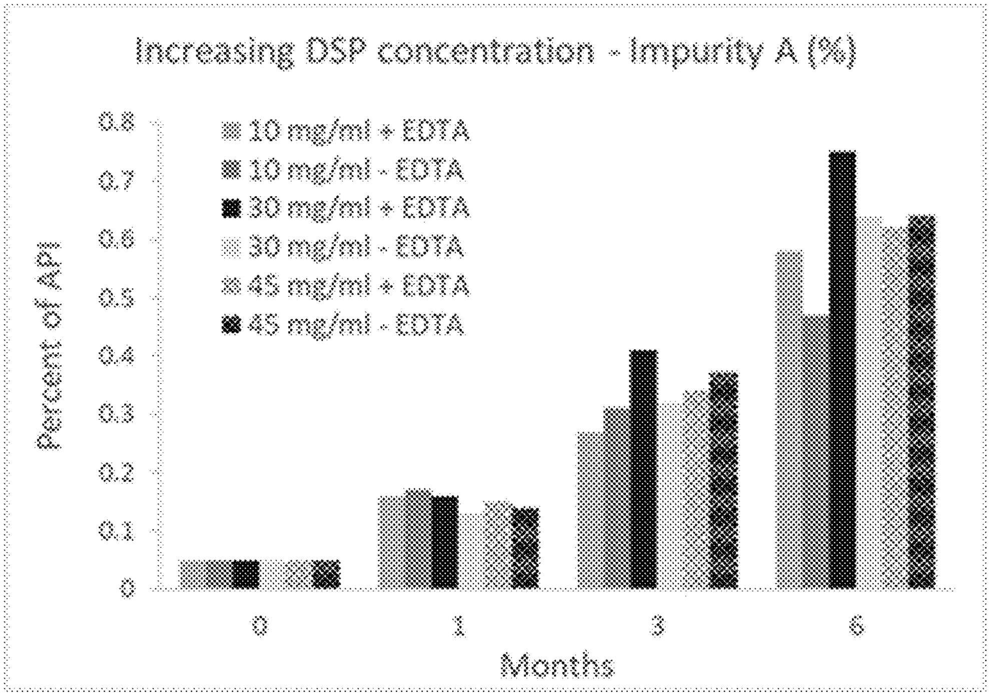
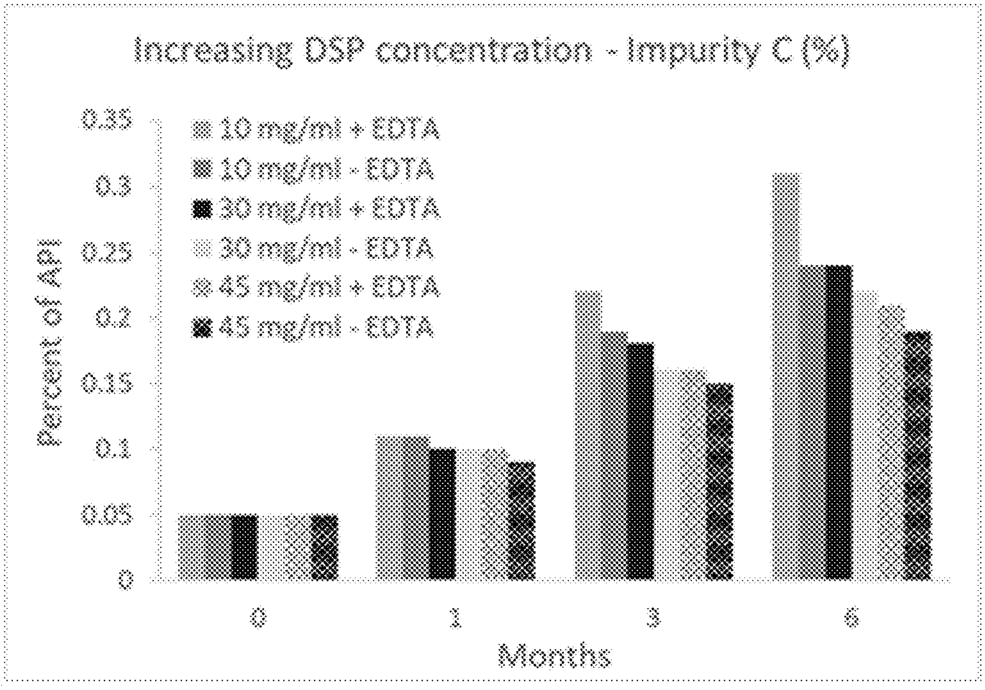

Figure 47
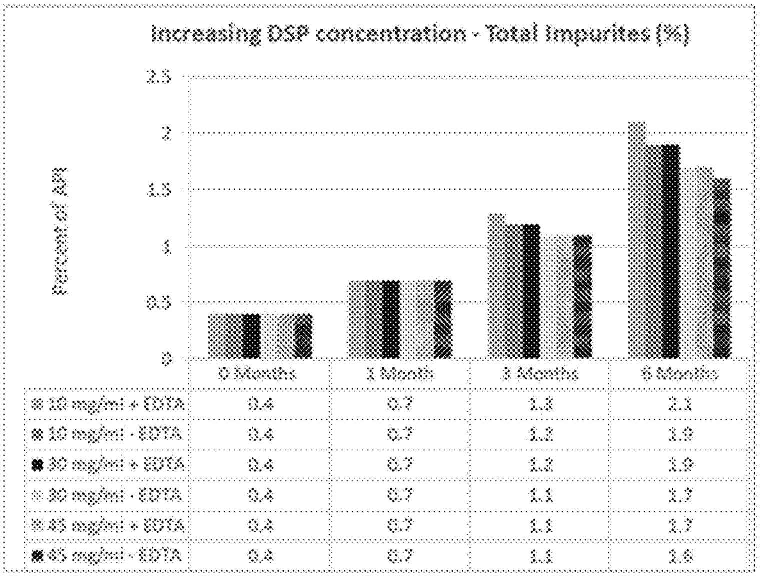
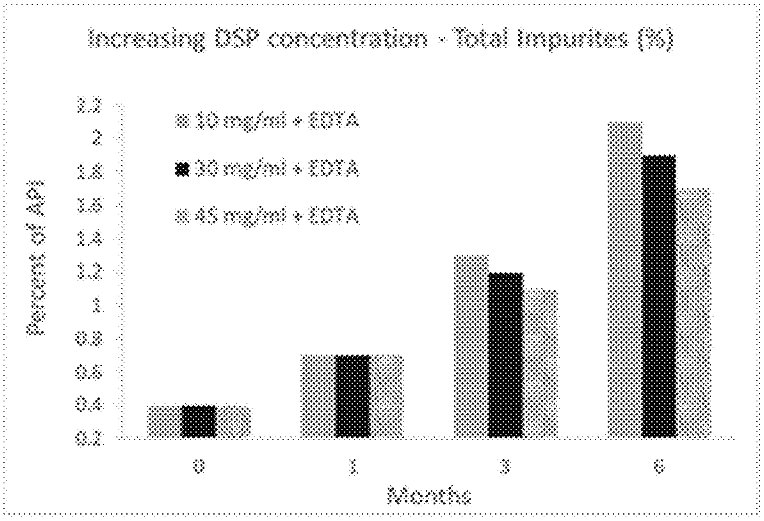
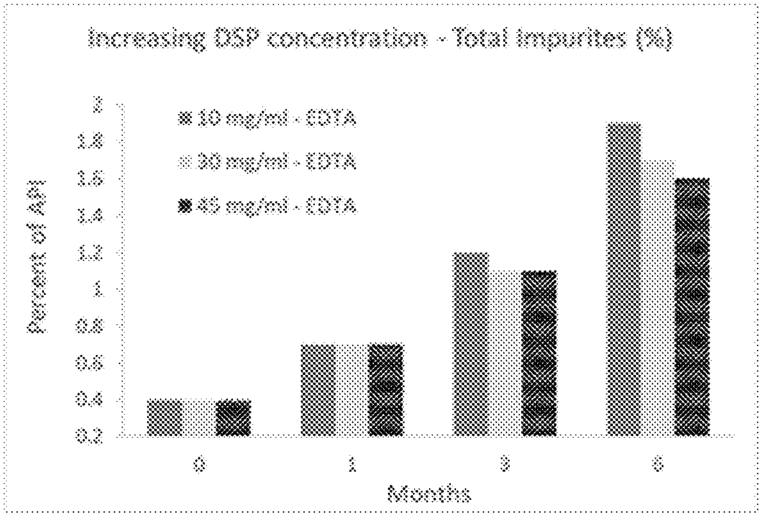

STABLE GLUCOCORTICOID FORMULATION

CROSS-REFERENCE TO RELATED APPLICATIONS

This application is a continuation of International Application No. PCT/US2019/061363, filed Nov. 14, 2019, which claims the benefit of priority of U.S. Provisional Application No. 62/767,448, filed Nov. 14, 2018, each of which is incorporated by reference herein in its entirety for any purpose.

FIELD

The present invention relates to stable glucocorticoid formulations with low concentrations of preservatives. More particularly, the present invention relates to high concentration formulations of a glucocorticoid-containing aqueous pharmaceutical composition that is formulated with low levels of antioxidant acting preservatives. Such preservatives that have previously been formulated at high dose levels have been found to be associated with patient toxicity. Accordingly, the ability to achieve continued drug stability and purity in the presence of low levels of antioxidants, as disclosed herein, is highly desirable.

BACKGROUND

There are many reported disadvantages associated with the use of preservatives and antioxidants typically added to pharmaceutical compositions to maintain stability. (American Hospital Formulary Service. Volumes I and II. Washington, DC: American Society of Hospital Pharmacists, to 1984., p. 40:08). For example, the field of pediatrics is struggling with toxic excipients of liquid formulations to the extent that an entire industry is making an effort to switch to new solid formulation forms (mini-tablets, orodisperse films etc.; Thabet et al. 2018). The European Paediatric Formulation Initiative is working on the "Safety and Toxicity of Excipients for Paediatrics" (STEP)—database, which provides toxicologic information (thresholds etc.) on selected pharmaceutical excipients for pediatric use. (see www.eupfi.org/step-database-info/). New liquid formulations with excipients either absent from the STEP database list or without a set threshold are desperately needed.

Parabens are a class of widely used preservatives in both cosmetic and pharmaceutical products. There are reports that parabens are associated with toxic side effects—for example, the controversial status of propylparaben concerning reproductive toxicity (Oishi et al., 2002) has not yet been resolved (excipient no longer covered by the European Food Safety Authority (EFSA) entry for food additives; EFSA unable to recommend a specific acceptable daily intake (ADI)). Parabens were associated with aeroallergen sensitization (Savage et al. 2012; Spanier et al. 2014) and an increase in the potential risk of allergic disease. In particular when administered as a high-dose bolus due to compounding formulations (increased levels), parabens might become a dangerous trigger for allergies.

Benzyl alcohol is used as a bacteriostatic preservative at low concentration in a number of intravenous medications, cosmetics, and topical drugs. Benzyl alcohol's severe toxicity regarding neonates is well-recognised (Gershanik et al., 1982; Hiller et al., 1986; Benda et al., 1986; Jardine and Rogers at al., 1989). Due to its generally recognized toxicity (neural, hemolytic, mucous membrane irritant), the World Health Organisation (Joint FAO/WHO Expert Committee on Food Additives; JECFA) set an ADI treshold of 5 mg/kg.

Benzethonium chloride is used as a preservative in pharmaceutical and cosmetic products. It is an irritant and allergic sensitizer in humans (Benjamin et al. 2011, Dao et al. 2012). Very recent data suggests that it could potentially exacerbate inflammatory bowel disease and associated colon cancer (Sanidad et al. 2018).

Propylene glycol is used as a vehicle for topical, oral, and intravenous pharmaceutical preparations. It may also be used as a preservative in pharmaceutical and cosmetic products. Propylene glycol, given in amounts ≥3 g/day IV, can accumulate and cause lactic acidosis, CNS depression, coma, hypoglycemia, seizures, and hemolysis (Lim et al. 2014). Patients at risk for toxicity include infants, patients with renal insufficiency or patients with epilepsy. Therefore the Committee for Human Medicinal Products, EMA/CHMP/334655/2013 (November 2014) has set thresholds of 1 mg/kg (neonates up to 28 days), 50 mg/kg (29 days up to 4 years), 500 mg/kg (5 years up to 17 years and adults).

Creatinine has been used as a stabilizing excipient for high-concentration, low volume Dexamethasone Sodium Phosphate (DSP; withdrawn) formulations in the past. Intravenous administration of those formulations lead to artifactually elevated patient creatinine lab results due to analytically correct measurement of creatinine added as an excipient (Darby et al. 2012).

Sulfites are also widely used as preservative and antioxidant additives in the pharmaceutical industries. Exposure to such sulfites has been reported to induce a range of adverse clinical effects in sensitive individuals, ranging from dermatitis, urticaria, flushing, hypotension and abdominal pain to life-threatening anaphylactic and asthmatic reactions. Sulfite-inducing symptoms range from mild in some individuals, to severe in others, and in some individuals the reactions can be life threatening (See, EFSA Journal 2016; 14(4):4438; www.efsa.europa.eu/en/efsajournal/pub/4438).

Obtaining the stability of a drug formulation without the potential toxicological side effects of preservatives and stabilizers can be difficult to achieve and it is difficult to prevent adverse and/or safety issues from occuring. More specifically, the concentration of a preservative necessary for stability of the formulation may create the potential for toxicological effects. Using lower concentrations of the preservative may help to reduce the potential for such toxicological side effects, but the lower concentrations of the preservatives may also be inadequate to achieve the desired assay level. That is, using lower concentrations of the preservative may help to reduce the potential for such toxicological side effects, but the lower concentrations of the preservatives may also be inadequate to maintain required levels of chemical and physical stability of the formulation over time. Stability of the formulation over time may be determined, for example, by assaying quantitative chemical attributes of the formulation such as levels of the active pharmaceutical ingredient (API) or its degradation products.

As stated above, pharmaceutical compositions typically require the addition of preservatives, stabilizers, and antioxidant additives such as sodium sulfite to maintain the stability of the composition. Examples of such pharmaceutical compositions include solutions and suspensions that are injected into the bodies of humans or other mammals. For such parenteral products, where inert gases as well as nitrogen are used as the interior gas within the vials of injectables, manufacturers strive to reach a 100% level of saturation of a chosen gas within the vial headspace in order to restrict the amount of oxygen which can contribute to oxidative degradation of the API. However, due to manufacturing limitations during good manufacturing practice (GMP) manufacture and filling, it is possible for trace amounts of oxygen to be introduced inadvertently, reducing the product's shelf-life and stability when compared to its registration label.

Furthermore, since it is known that no containers are perfectly gas tight (e.g. tested for stoppered vials with lyophilized product: ~1.3% atm oxygen permeation per year; Lighthouse Instruments webinar "Determining & Controlling Oxygen Levels in Sensitive Formulations"-www2.lighthouseinstruments.com/1/302881/2018-02-26/2nytk), oxygen permeates into the vials over time. Permeation occurs either through the rubber stopper material of the vial or through microchannels between the rubber stopper and the vial neck interphase.

Therefore, when a new formulation is planned, a threshold of headspace oxygen needs to be considered. Knowing the impact of excess oxygen allows the manufacturer to calculate the impact on stability of the drug product and potentially reduce the quantity of excipient utilized in that formulation. Formulations with increasing amounts of oxygen content in percent can be manufactured for Design of Experiment (DoE) studies to simulate a worst-case scenario. The formulations with varying levels of headspace oxygen are then set on stability and eventually an assay and shelf-life is determined for increasing levels of oxygen. That is, the formulations with varying levels of headspace oxygen are then tested for stability and an assay of quantitative chemical attributes (e.g. API amount, presence of degradation products, pH, etc.) and shelf-life is determined for increasing levels of oxygen.

Means for determining headspace oxygen levels in a given headspace volume are well known to those skilled in the art. For example, headspace oxygen levels may be measured by conventional destructive techniques, such as electrochemical methods or gas chromatography, or by non-destructive methods such as laser-based Frequency Modulation Spectroscopy (Pharmaceutical Technology, July 2002; Lighthouse Instruments Application Note 102).

Such compositions and formulations once packaged can therefore carry trace amounts of oxygen from the manufacturing process, thereby decreasing the stability of the composition or formulation. Moreover, aside from degrading oxidative processes, hydrolyzation contributes to degradation of the API and reduces the assay as well as increases the accumulation of unwanted impurities above a safe threshold.

Accordingly, it is necessary to employ a means for preventing such degradation from occurring and the means employed may be the addition of an antioxidant, stabilizer, and/or antimicrobial chemical agent (herein referred to as "preservative") that maintains the assay of the composition.

Decadron™ 24 mg/ml, manufactured by Merck (withdrawn) had a headspace volume to API ratio of 0.0075 and a "(Sulfite:API)×headspace" value of 0.03750, with antioxidants (preservatives) present at 1 mg/ml sodium bisulfite, 1.5 mg/ml methylparaben, 0.2 mg/ml propylparaben, 8 mg/ml creatinine. DBL™ Dexamethasone Sodium Phosphate 24 mg/ml, manufactured by Hospira (withdrawn) had a headspace volume to API ratio of 0.0075, with antioxidants (preservatives) present at 8 mg/ml creatinine and 0.5 mg/ml disodium edetate. Solcort™ 24 mg/ml manufactured by Fuji Pharma (Japan) has a headspace volume to API ratio of 0.0075, with antioxidants (preservatives) present at 0.5 mg/5 ml Benzethonium chloride.

Dexamethasone 10 mg/ml, manufactured by Hameln Pharmaceuticals has a headspace volume to API ratio of 0.0075 with propylene glycol and disodium edetate as antioxidants (preservatives). Dexamethasone Sodium Phosphate 10 mg/ml, distributed by Physicians Total Care, Inc. has a headspace volume to API ratio of 0.01920 and a "(Sulfite:API)×headspace"—value of 0.19200 and antioxidants (preservatives) of 1 mg/ml sodium metabisulfite and 10 mg/ml benzyl alcohol. Dexamethasone Sodium Phosphate 10 mg/ml, manufactured by West-Ward Pharmaceuticals Corp. has a headspace volume to API ratio of 0.02 and a "(Sulfite:API)×headspace"—value of 0.03, with antioxidants (preservatives) present at 1.5 mg/ml sodium sulfite 10.42 mg/ml benzyl alcohol. Dexamethasone Sodium Phosphate 10 mg/ml, manufactured by Mylan has a headspace volume to API ratio of 0.02 and antioxidants (preservatives) of 1.5 mg/ml methylparaben, 0.2 mg/ml propylparaben, 0.11 mg/ml disodium edetate (0.11 mg in 1 mL). Dexamethasone Sodium Phosphate (preservative free) 10 mg/ml (only 1 ml total volume), manufactured by Fresenius has a headspace volume to API ratio of 0.02. Dexamethasone Sodium Phosphate (preserved) 10 mg/ml (10 ml total volume), manufactured by Fresenius has a headspace volume to API ratio of 0.0404 and antioxidants (preservatives) present at 10 mg/ml benzyl alcohol.

Dexamethasone Sodium Phosphate 4 mg/ml, manufactured by West-Ward Pharmaceuticals Corp. has a headspace volume to API ratio of 0.0375 and a "(Sulfite:API)×headspace"—ratio of 0.1875, with antioxidants (preservatives) present at 1 mg/ml sodium sulfite anhydrous, 10.42 mg/ml benzyl alcohol. Dexamethasone 4 mg/ml (2 ml total volume), manufactured by Hospira has a headspace volume to API ratio of 0.05 and a "(Sulfite: API)×headspace"—ratio of 0.007 with antioxidants (preservatives) present at 0.5 mg/ml disodium edetate, 0.07 mg/ml sodium sulphite anhydrous.

Dexaject SP 3.66 mg/ml, manufactured by Henry Schein Animal Health has a headspace volume to API ratio of 0.04918 and a "(Sulfite: API)×headspace"—ratio of 9.836 with antioxidants (preservatives) present at 2 mg/ml sodium bisulfite, 1.5% benzyl alcohol.

These and other dexamethasone-containing formulations are described in Supplementary Tables A-F.

Thus, there is a need for a means to maintain the stability of the pharmaceutical environment so that very low concentrations of preservatives can be utilized without reducing the shelf-life of the product to the extent where the product would no longer be safely administered.

A need exists for a means to maintain the stability of aqueous pharmaceutical formulations comprising a glucocorticoid with low concentrations of preservatives. Aqueous pharmaceutical formulations comprising a glucocorticoid and low or no amounts of preservative without reduced stability or shelf-life are desired.

SUMMARY

The following brief summary is not intended to include all features and aspects of the present invention, nor does it imply that the invention must include all features and aspects discussed in this summary.

The present disclosure is directed to high concentration glucocorticoid-containing pharmaceutical compositions comprising reduced levels of antioxidant-acting preservatives. More particularly, the present disclosure is directed to aqueous pharmaceutical formulations comprising a glucocorticoid. The pharmaceutical formulations disclosed herein comprise reduced levels of preservative and/or chelating agent as compared to known glucocorticoid-containing formulations.

The present disclosure is based on the finding that use of a defined headspace volume to API ratio during the filling of the formulation into vials results in a maintained stability of the compositions close to the state directly after manufacture in the presence of reduced levels of antioxidant preservatives.

That is, the present disclosure is based on the finding that use of a defined headspace volume (ml) to glucocorticoid (mg) ratio during packaging of the glucocorticoid containing formulation into containers (e.g. vials) results in stability of the formulation being maintained close to its state directly after manufacture. Surprisingly, this effect is observed even when the formulation comprises reduced or no amounts of preservative (e.g. antioxidants). The defined headspace volume (ml) to glucocorticoid (mg) ratio disclosed herein is lower than that used in known glucocorticoid formulations (see Example 1, Table 1).

Without being bound by theory, it is believed that use of a defined headspace volume (ml) to glucocorticoid (mg) ratio as disclosed herein (and which is lower than that used in known glucocorticoid formulations) results in fewer oxygen molecules being present per given molecule of glucocorticoid. Accordingly, a given amount of glucocorticoid molecules is presented with fewer oxygen molecules resulting in less oxidative degradation (and accumulation of impurities over time).

More specifically, the present invention is based on a finding that reduced headspace volume to API ratio, beyond typical manufacturing (see Table 1), allows sulfite preservatives to be 35 ppm or lower as well as chelators (Disodium Edetate) to be 500 ppm or lower (Example 2) to achieve at least a minimum of 24 months shelf-life at between 2° C. to 30° C. (Table 4, FIG. 1-26).

That is, the present authors have demonstrated that use of such a reduced headspace volume (ml) to glucocorticoid (mg) ratio allows sulfite preservatives to be present at 0.035 mg/ml (35 ppm) or less, and chelating agent (Disodium Edetate) to be present at 0.5 mg/ml (500 ppm) or less in a formulation with up to 48 months shelf-life when stored at 25° C./60% RH (see Example 2).

Moreover, the present invention is additionally based on the finding that Dexamethasone Sodium Phosphate (DSP) in higher concentration in a solution becomes increasingly self-protective as an API (concentration dependence not known in the industry) against degrading processes like hydrolyzation and oxidization, enabling the above ranges of 0-35 ppm for sulfite preservatives and 0-500 ppm for chelators (Disodium Edetate).

That is, the present disclosure is also based on the unexpected finding that the glucocorticoid Dexamethasone Sodium Phosphate (DSP), when present in high concentrations in an aqueous formulation, is increasingly self-protective against degradative processes like hydrolyzation and oxidization. This concentration-dependent self-protection, which has not previously been reported, also contributes to stability of the disclosed aqueous formulations These unexpected findings of the present authors allow for the manufacture of aqueous pharmaceutical formulations comprising a glucocorticoid and low or no amounts of preservative and/or chelating agent, which formulations have shelf-lives which are comparable to, or longer than, those of known preservative-containing glucocorticoid formulations. That is, the compositions and formulations of the invention allow for long-term storage of glucocorticoid solutions which contain low or no amounts of preservative and/or chelating agent.

Accordingly, in a first aspect, the invention provides a pharmaceutical composition comprising (i) a glucocorticoid, packaged with a headspace (volume; [ml]) to glucocorticoid (weight [mg]) ratio of 0-0.00588, and (ii) a preservative in a concentration of less than 70 ppm.

The pharmaceutical compositions of the present invention offer several advantages over existing formulations. Given that antioxidant preservatives have been found to be associated with patient sensitivity and toxicity, pharmaceutical compositions comprising lower levels of such preservatives, while retaining stability of the composition, is highly desirable. In a specific embodiment of this invention, the antioxidant is Sodium Sulfite (Anhydrous), an excipient absent from the STEP—database, which is monitoring toxic excipients for use in pediatric populations (Thabet et al. 2018; Nellis et al. 2015; Turner et al. 2014). In a specific embodiment of the invention, AVM0703 refers to the initial target formulation of the DoE study (see Formulations 2, 4, 6, 8, 12 in Tables 4-7).

In a second aspect, the invention provides a method for producing a pharmaceutical composition having a low concentration of preservative, based on packing of said pharmaceutical composition with a headspace (volume; [ml]) to glucocorticoid (weight [mg]) ratio of 0-0.00588.

As outlined above, the present disclosure also relates to methods for production of high concentration glucocorticoid containing pharmaceutical compositions comprising reduced levels of antioxidant preservatives. Such methods comprise the step of mixing components of the composition and packaging said composition in an environment wherein the headspace volume to API ratio as well as the antioxidant to total API ratio is decreased.

In a third aspect, the invention provides a method of treating a host in need of glucocorticoid treatment, comprising administering a pharmaceutical composition of the invention. That is, the present disclosure is further directed to use of the pharmaceutical compositions disclosed herein for treatment of patients in need of glucocorticoid drugs. Such methods of treating a host include administration of the compositions to patients in need of anti-inflammatory, immunosuppression, lymphoablation, germinal center elimination, IL-2 IL-7 IL-12 and/or IL-15 elevation, mesenchymal stem cell elevation, G-CSF increase, neutrophil increase, tumor/cancer killing or lymphodepletion (preconditioning) before cell-based therapy, FGF-18 elevation, cartilage production, hematopoietic stem cell elevation and/or neutrophil production, or improvement in Performance Status among patients with diseases that include but are not limited to cancer and autoimmune diseases, for example.

In a fourth aspect, the invention provides an aqueous pharmaceutical formulation comprising dexamethasone and a preservative, wherein the formulation is packaged in a container with a headspace volume (ml) to dexamethasone content (mg) ratio of 0.007 or less, and wherein the concentration of preservative is or is less than about 0.1 mg/ml. The present inventors have found that use of a defined headspace volume (ml) to glucocorticoid (mg) ratio during packaging of the glucocorticoid containing formulation into containers (e.g. vials) results in stability of the formulation being maintained close to its state directly after manufacture. Surprisingly, this effect is observed even when the formulation comprises reduced or no amounts of preservative (e.g. antioxidants).

In some embodiments, the dexamethasone is dexamethasone sodium phosphate. In some embodiments, the concentration of dexamethasone phosphate in the formulation is at least 24 mg/ml. In some embodiments, the headspace volume (ml) to dexamethasone content (mg) ratio is 0.00588 or less. In some embodiments, the headspace volume comprises less than about 10% oxygen, more preferably less than about 5% oxygen.

In some embodiments, the concentration of preservative is or is less than about 0.035 mg/ml. In some embodiments, the preservative is a sulfite, a paraben, benzyl alcohol, benzethonium chloride, propylene glycol, and/or creatinine. In some embodiments, the sulfite is sodium sulfite (anhydrous), sodium bisulfate, and/or sodium metabisulfite. In some particularly preferred embodiments, the formulation does not comprise a preservative. The present inventors have demonstrated that use of the defined headspace volume (ml) to glucocorticoid (mg) ratios of the present invention allows the formulations of the invention to remain stable up to 29 months (and projected up to 48 months) after manufacture, even with low or no amounts of preservative.

In some embodiments the formulation comprises one or more chelating agent. In some embodiments, the concentration of chelating agent is or is less than about 0.50 mg/ml. In some embodiments, the chelating agent is disodium edetate (disodium EDTA). In some particularly preferred embodiments, the formulation does not comprise a chelating agent. The present inventors have demonstrated that use of the defined headspace volume (ml) to glucocorticoid (mg) ratios of the present invention allows the formulations of the invention to remain stable without use of a chelating agent.

In some embodiments, the dexamethasone is selected from the group consisting of dexamethasone base, dexamethasone sodium phosphate and dexamethasone acetate. In some preferred embodiments, the dexamethasone is dexamethasone sodium phosphate.

In some embodiments, the shelf-life of the formulation is at least about 18, 24, 36, or 48 months when stored between 2° C. to 40° C. In some embodiments, the formulation remains stable when stored between 2° C. to 40° C. for at least about 18, 24, 36, or 48 months.

In some embodiments, the amount of glucocorticoid in the formulation is maintained between ±5.0% as compared to the date of manufacture when the formulation is stored between 2° C. to 40° C. for at least about 18, 24, 36, or 48 months. In some embodiments, the formulation exhibits less than ±0.5 change in pH when stored between 2° C. to 40° C. for at least about 18, 24, 36, or 48 months.

In some embodiments, the formulation exhibits less than about 0.50% accumulation of impurity A when stored between 2° C. to 40° C. for at least about 18, 24, 36, or 48 months. In some embodiments, the formulation exhibits less than about 0.50% accumulation of impurity B when stored between 2° C. to 40° C. for at least about 18, 24, 36, or 48 months. In some embodiments the formulation exhibits less than about 0.50% accumulation of impurity G when stored between 2° C. to 40° C. for at least about 18, 24, 36, or 48 months. In some embodiments, the formulation exhibits less than about 0.20% accumulation of unspecified impurities when stored between 2° C. to 40° C. for at least about 18, 24, 36, or 48 months. In some embodiments, the formulation exhibits less than about 3.0% accumulation of total impurities when stored between 2° C. to 40° C. for at least about 18, 24, 36, or 48 months.

In a fifth aspect, the invention provides an aqueous pharmaceutical formulation as defined herein, for use in a method of treatment.

In a sixth aspect, the invention provides use of an aqueous pharmaceutical formulation as defined herein for the preparation of a medicament for use in a method of treatment.

In a seventh aspect, the invention provides a method of treatment comprising administering to a subject in need thereof, a therapeutically effective amount of an aqueous pharmaceutical formulation as defined herein.

In an eighth aspect, the invention provides a method for stabilising an aqueous pharmaceutical formulation comprising dexamethasone and a preservative, the method comprising packaging an aqueous pharmaceutical formulation as defined herein into a container with a headspace volume (ml) to dexamethasone content (mg) ratio of 0.007 or less.

The invention includes the combination of the aspects and preferred features described except where such a combination is clearly impermissible or expressly avoided.

BRIEF DESCRIPTION OF TABLES

TABLE 1 demonstrates that AVM0703 is below the values typically found in manufactured Dexamethasone Sodium Phosphate formulations in the industry concerning headspace volume [ml] to total API (Dexamethasone Phosphate equivalent) [mg] ratio, total Sulfite [mg] to total API (Dexamethasone Phosphate equivalent) [mg] ratio as well one of the lowest "(Sulfite/API)×Headspace Volume" value. Moreover, the comparison shows estimated/measured headspace volumes, API concentrations and contents, sulfite concentrations and contents as well as their calculated ratios of selected (commercially available) Dexamethasone Sodium Phosphate solutions (vials or ampouls) in the market compared to AVM0703.

TABLE 2 demonstrates the composition of the Target Point (Center Point) Formulation of the Design of Experiment in mg/ml.

TABLE 3 demonstrates the composition of the Target Point Formulation of the Design of Experiment in weight percent.

TABLE 4 demonstrates the composition of 10 of the 16 formulations that were monitored for long-term storage (25° C./60% RH). These formulations were part of the first Design of Experiment study.

TABLE 5 demonstrates six formulations with varying levels of Sodium Sulfite (Anhydrous) and Headspace Oxygen which were tested for maintaining the assay at 18 months (25° C./60% RH). Aside from F15 (atmospheric Oxygen level of 20.9%), all 5 other formulations (F2, 4, 9, 10 and 11) were within the required API assay or impurity thresholds. Those six were selected from 16 formulations that were manufactured for the DoE study to assess those 2 factors: 14 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml Sodium Sulfite (Anhydrous), respectively.

TABLE 6 demonstrates nine formulations with varying levels of Sodium Sulfite (Anhydrous) and Headspace Oxygen which were tested for stability at 24 months. Aside from F15 (atmospheric Oxygen level of 20.9%), all other 8 formulations (F2, 4, 6, 8, 9, 10, 11 and 12) were within the required API assay or impurity thresholds. Those nine were selected from 15 formulations that were manufactured for the DoE study to assess those 2 factors: 13 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml Sodium Sulfite (Anhydrous), respectively.

TABLE 7 demonstrates nine formulations with varying levels of Sodium Sulfite (Anhydrous) and Headspace Oxygen which were tested for stability at 29 months. Aside from F15 (atmospheric Oxygen level of 20.9%), all other 8 formulations (F2, 4, 6, 8, 9, 10, 11 and 12) were within the required API assay or impurity thresholds. Those nine were selected from 15 formulations that were manufactured for the DoE study to assess those 2 factors: 13 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml Sodium Sulfite (Anhydrous), respectively.

TABLE 8 demonstrates the composition of ten formulations used in a design of experiment series (up to 6 months at 40° C./75% RH) to assess the stability of the formulation without the presence of either sodium sulfite or EDTA at increasing levels of headspace oxygen (═HO: 0%, 5%, 10% and 15%): Ten formulations with the specifications shown in the table were manufactured (GLP grade) and tested for stability. 26.23 mg/ml DSP equals 24 mg/ml Dexamethasone Phosphate.

TABLE 9 demonstrates 10 additonally manufactured formulations for an extended DoE study which were conducted to assess the shelf-life of the formulation in the absence of Sodium Sulfite (Anhydrous) and/or Disodium Edetate at different levels of headspace oxygen (0, 5, 10, 15%). Storage conditions are 40° C./75% RH (inverted vial position) with sampling carried out at 0, 1, 3 and 6 months.

Table 10 demonstrates four additionally manufactured formulations with 2 varying levels of DSP (10 and 30 mg/ml) for an extended DoE study which was conducted to assess the shelf-life of the formulation with increasing DSP concentration in the presence or absence of Disodium Edetate (0.5 mg/ml). All four formulations contained 5% headspace oxygen (95% nitrogen) and lacked sulfite. Storage conditions are 40° C./75% RH (inverted vial position) with sampling carried out at 0, 1, 3 and 6 months.

Table 11 demonstrates two additionally manufactured formulations with 45 mg/ml DSP for an extended DoE study which was conducted to assess the shelf-life of the formulation with increasing DSP concentration in the presence or absence of Disodium Edetate (0.5 mg/ml). Both formulations contained 5% headspace oxygen (95% nitrogen) and lacked sulfite. Storage conditions are 40° C./75% RH (inverted vial position) with sampling carried out at 0, 1, 3 and 6 months.

Table 12 demonstrates the results of the additional design of experiment for increasing concentrations of Dexamethasone Sodium Phosphate (DSP). The six formulations (shown in Tables 10 and 11) with 3 varying levels of DSP (10, 30 and 45 mg/ml, equivalent to 9.15, 27.45 and 41.17 Dexamethsone Phosphate (DP)) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. The results demonstrates that the formulations with an increasing DSP concentration form less total impurities over time.

SUPPLEMENTARY TABLE A demonstrates the excipient profile, strength and vial volumes of commercially available Dexamethasone Sodium Phosphate injectables for human use in the U.S.

SUPPLEMENTARY TABLE B demonstrates examples of Dexamethasone Sodium Phosphate formulations including their excipient profile (U.S. market).

SUPPLEMENTARY TABLE C demonstrates examples of Dexamethasone Sodium Phosphate formulations including their excipient profile (U.S. veterinary market).

SUPPLEMENTARY TABLE D demonstrates examples of high-dose Dexamethasone Sodium Phosphate formulations (injectables) including their excipient profile (international market).

SUPPLEMENTARY TABLE E demonstrates examples of previous patents disclosing Dexamethasone formulations with a much higher sulfite content.

SUPPLEMENTARY TABLE F demonstrates examples of Dexamethasone formulations including their shelf-life as disclosed by the manufacturers.

BRIEF DESCRIPTION OF THE DRAWINGS

Embodiments and experiments illustrating the principles of the invention will now be discussed with reference to the accompanying figures in which:

FIG. 5 demonstrates that the target point formulations 2 and 4 (F2, F4: 0.035 mg/ml Sodium Sulfite Anhydrous, 5.4% Oxygen headspace) are expected to have an assay above 95% for the Dexamethasone Sodium Phosphate content for 48 months (projection with 6 measured data points; up to 29 months, 25° C./60% RH).

FIG. 27 demonstrates the identity and structure of known impurities (Impurity A, B, C, D, E, F, G) derived from Dexamethasone Sodium Phosphate (Dexamethasone sodium phosphate (DSP; 9-fluoro-11b,17,21-trihydroxy-16a-methylpregna-1,4-diene-3,20-dione 21-(dihydrogen phosphate) Disodium Salt) solutions during storage. Impurity A: (9-fluoro-11β3,17,21-trihydroxy-16α-methylpregna-3,20-dione (dexamethasone); Impurity B: (9-fluoro-11β,17-dihydroxy-16β-methyl-3,20-dioxopregna-1,4-dien-21-yl dihydrogen phosphate (betamethasone phosphate); Impurity C, D, E, F: for each impurity, one or more diastereoisomer(s) of (9-fluoro-11β,17α-dihydroxy-16-methyl-3,17-dioxo-D-homo-androsta-1,4-dien-17a-yl)methyl dihydrogen phosphate (undefined stereochemistry at C-16 and C-17a), or (9-fluoro-11β,17-dihydroxy-16α-methyl-3,17a-dioxo-D-homo-androsta-1,4-dien-17-yl)methyl dihydrogen phosphate (undefined stereochemistry at C-17); Impurity G: 9-fluoro-11β,17-dihydroxy-16α-methyl-3-oxoandrosta-1,4-diene-17β-carboxylic acid. Equivalent USP impurity names are outlined.

FIG. 28 demonstrates ten formulations were tested for DSP assay (up to 6 months at 40° C./75% RH; 26.23 mg/ml DSP=24 mg/ml DP) to assess the stability of the formulation without the presence of either sodium sulfite or EDTA at increasing levels of headspace oxygen (=HO: 0%, 5%, 10% and 15%): All ten formulations contained 26.23 mg/ml DSP, which is equivalent to 24 mg/ml Dexamethasone Phosphate (DP). While all ten formulations passed the description at 3 months, only the following formulations passed the description as a clear solution at the 6 months stability time point:

Figure 1:
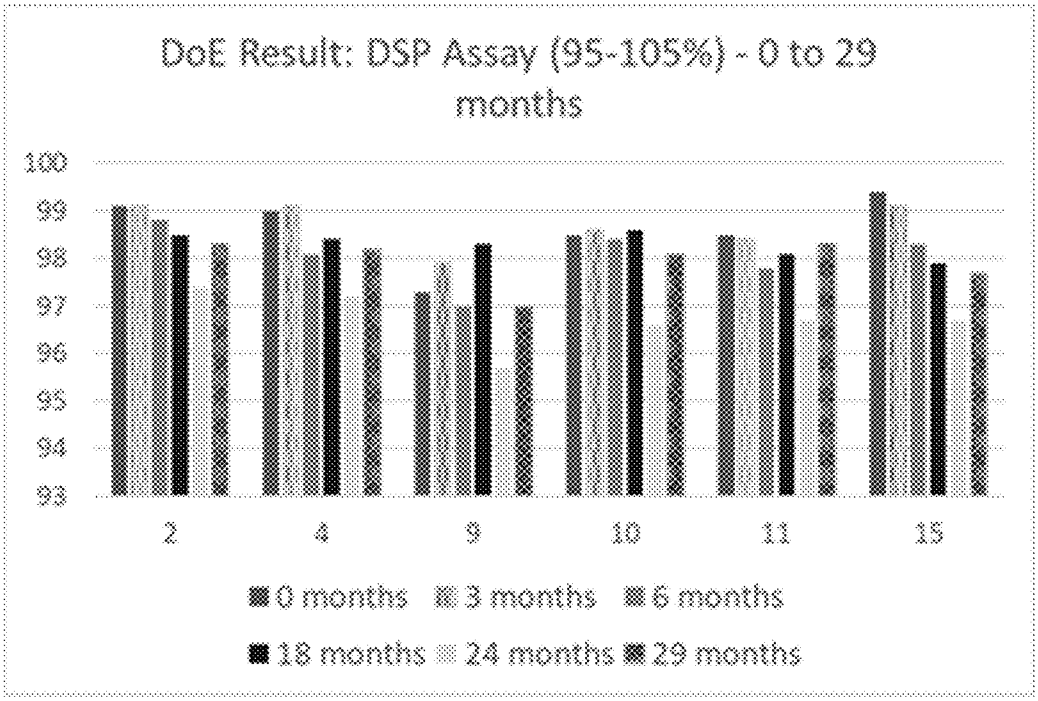
FIG. 1 demonstrates six formulations with varying levels of Sodium Sulfite (Anhydrous) and Headspace Oxygen which were tested for maintaining the assay at 25° C./60% RH (29 months). Formulation 2 and 4 (F2, 4) are target point formulations with 0.035 mg/ml Sodium Sulfite (Anhydrous) and 5% Headspace oxygen (95% nitrogen). The result demonstrates that the formulations are within a range of 95-105% DSP content for the tested values of Sodium Sulfite (Anhydrous) of 0 (F10), 0.035 (F2, 4, 11, 15) and 0.07 mg/ml (F9) at 5% (F2, 4, 9, 10), 10% (F11) and 20.90% (F15) headspace Oxygen, not dropping below 95% for any formulation tested.

(batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that formulation 2-1 shows the least degradation of all formulations at the 6 months time point while still passing description (no precipitation).

FIG. 29 demonstrates the additional design of experiment result for impurity A (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that formulation 2-1 showed the lowest accumulation of impurity A (Dexamethasone) of all formulations at the 6 months time point.

FIG. 30 demonstrates the additional design of experiment result for impurity B (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). Impurity B was not increasing for any of the formulations.

FIG. 31 demonstrates the additional design of experiment result for impurity C (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that the formulations with the highest headspace oxygen value showed the lowest accumulation of impurity C of all formulations at the 6 months time point.

FIG. 32 demonstrates the additional design of experiment result for impurity D (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. Impurity D increased the most from the 3 month time point to the 6 month time point for all formulations. Formulation 3-1 with sulfite and EDTA present at 0% headspace oxygen (HO) had the lowest value at 6 months of those 3 formulations that passed the description without a precipitate.

FIG. 33 demonstrates the additional design of experiment result for impurity F (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that none of the formulations increase for impurity F beyond the 0.2% threshold.

FIG. 34 demonstrates the additional design of experiment result for impurity G (up to 6 months at 40° C./75% RH; 26.23 mg/ml DSP=24 mg/ml DP) for the formulations without the presence of either sodium sulfite and/or EDTA at increasing levels of headspace oxygen (═HO: 0%, 5%, 10% and 15%): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that for impurity G, formulation 2-1 showed the lowest accumulation of all formulations at the 6 months time point.

FIG. 35 demonstrates the additional Design of experiment result for unidentified impurity (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The result shows that the two sulfite formulations (of all three without precipitation at 6 months) lacking EDTA (2-1, 2-2) show the lowest values of the highest unidentified impurity.

FIG. 36 demonstrates the additional Design of experiment result for total impurities (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The total impurities are the sum total of all previous impurities (A, B, C, D, F, G, highest unidentified impurity) as well as additionally all other unidentified impurities (with different retention times) that are of lower value. The result shows that the two sulfite formulations (of all three without precipitation at 6 months) lacking EDTA (2-1, 2-2) show the lowest values lowest amount of total impurities. Therefore, for this formulation no EDTA is needed at a storage condition of 40° C./75% RH at 0 or 5% headspace oxygen FIG. 37 demonstrates the DSP result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Dexamethasone Sodium Phosphate content is expected to be at 95% for 12 months (40° C./75% RH) for the formulation 2-1, while 2-2 and 3-1 are expected to be at a level of about 93% and 93.5% respectively. The result shows that EDTA is not necessary to achieve a better stability for the formulation.

Figure 38:
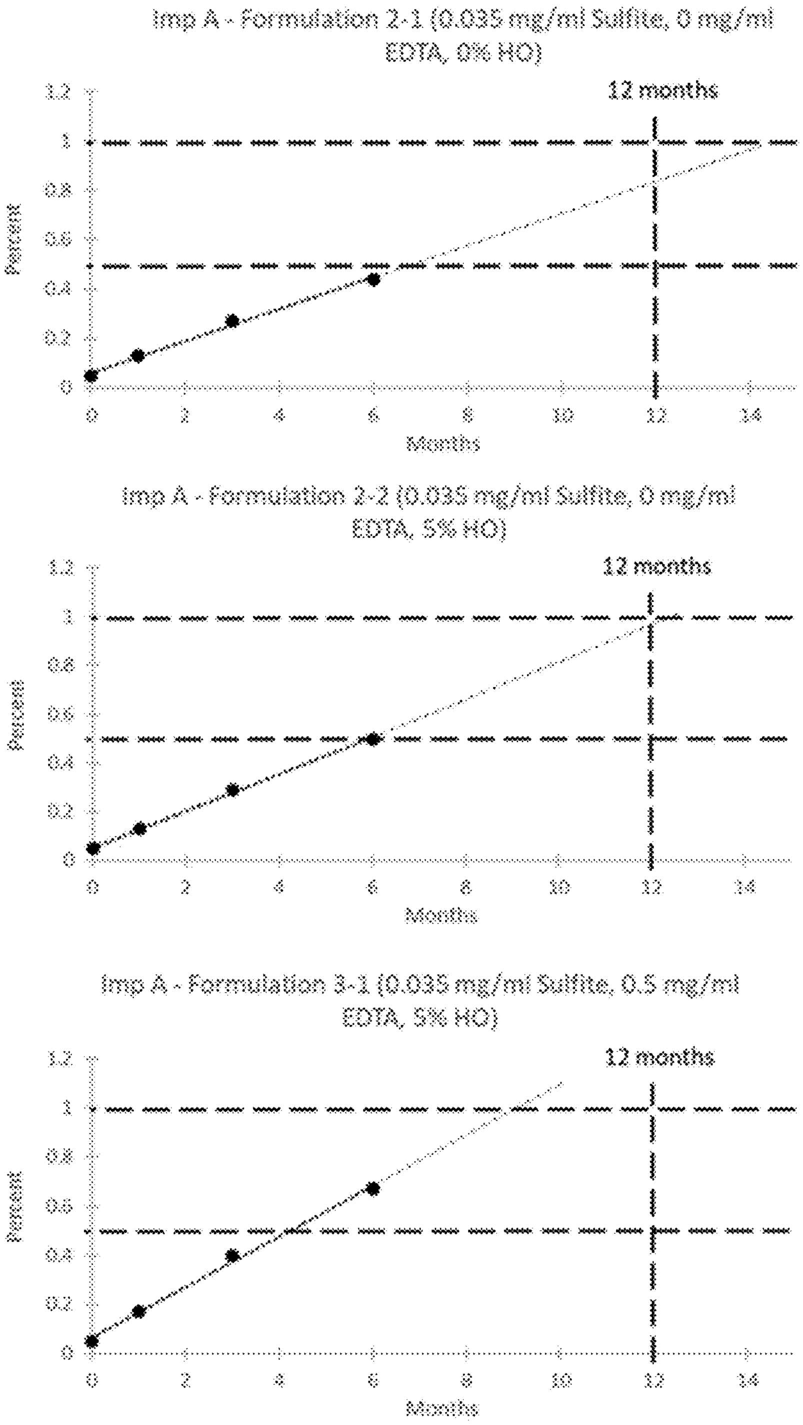

FIG. 38 demonstrates the Impurity A result and projection of the additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Impurity A level is expected to be below 1% for 12 months (40° C./75% RH) for the formulation 2-1 and 2-2, while for formulation 3-1 it is expected to reach 1% at about 9 months. The result shows that EDTA is not necessary to achieve a better stability for the formulation.

Figure 39:
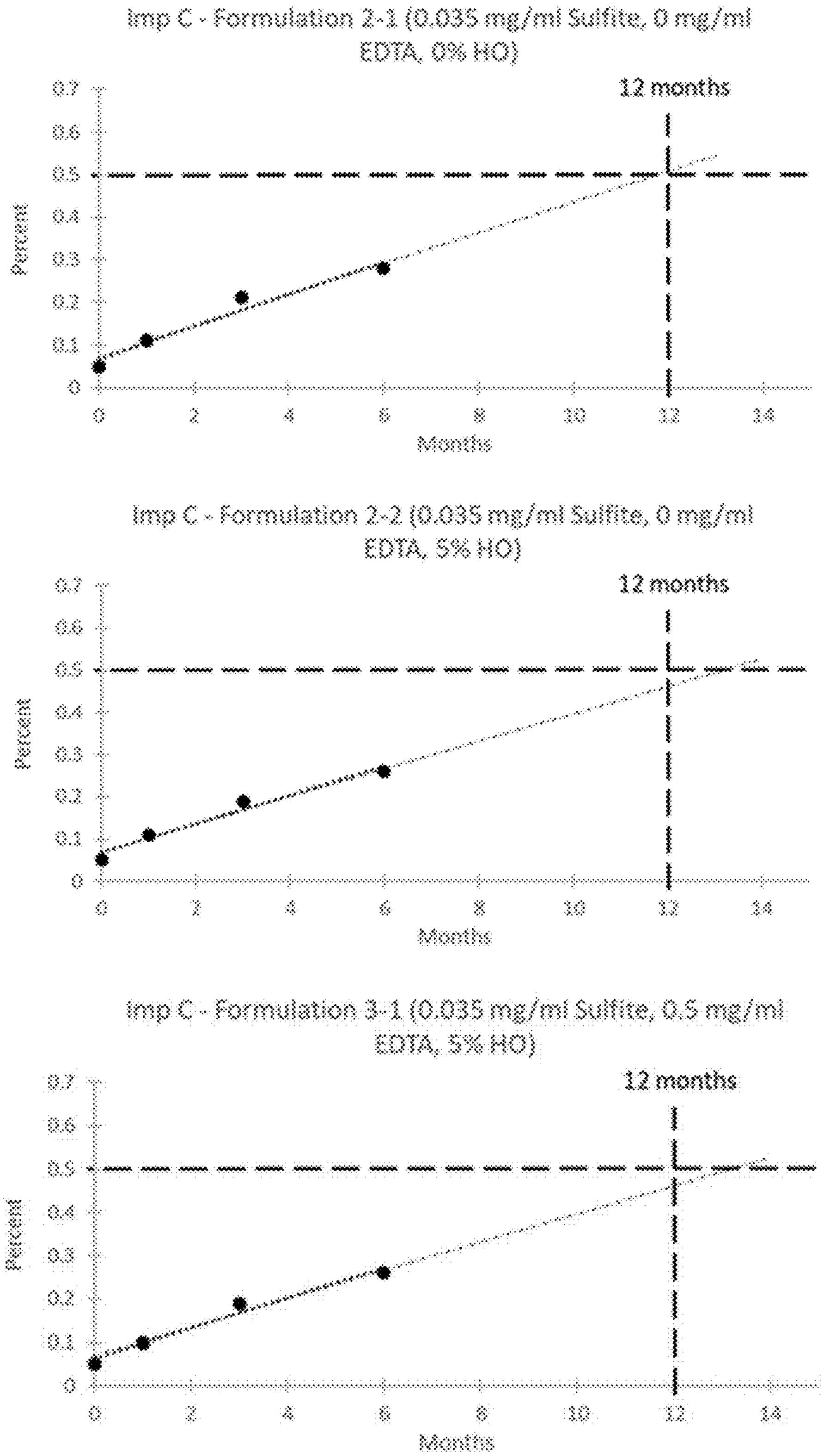

FIG. 39 demonstrates the Impurity C result and projection of the additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Impurity C level is expected to be at 0.5% for 12 months (40° C./75% RH) for the formulation 2-1, while being slightly below 0.5% for formulation 2-2 and 3-1 at this time point.

Figure 40:
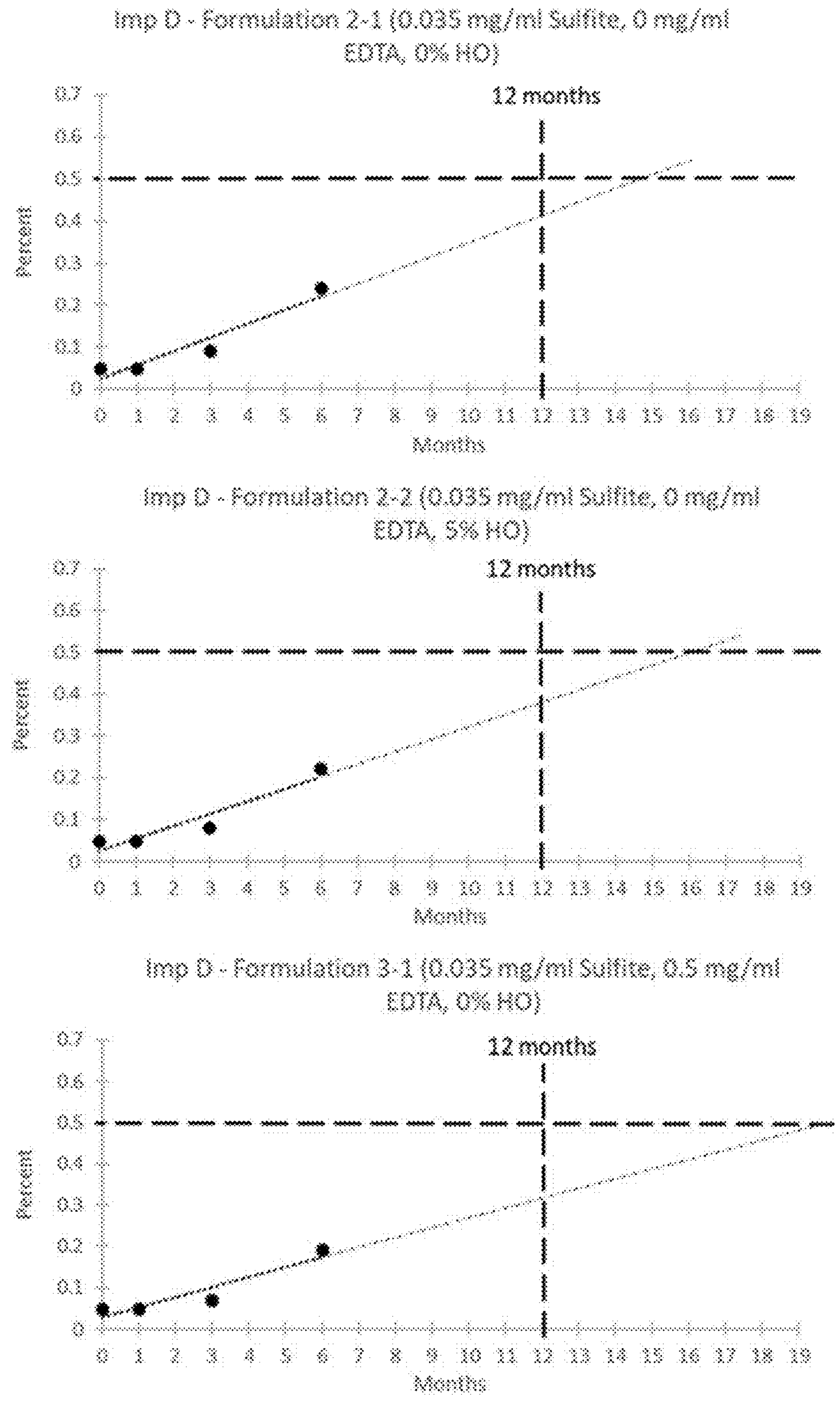

FIG. 40 demonstrates the Impurity D result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity D level is expected to be below 0.5% at 12 months (40° C./75% RH) for all 3 formulations.

Figure 41:
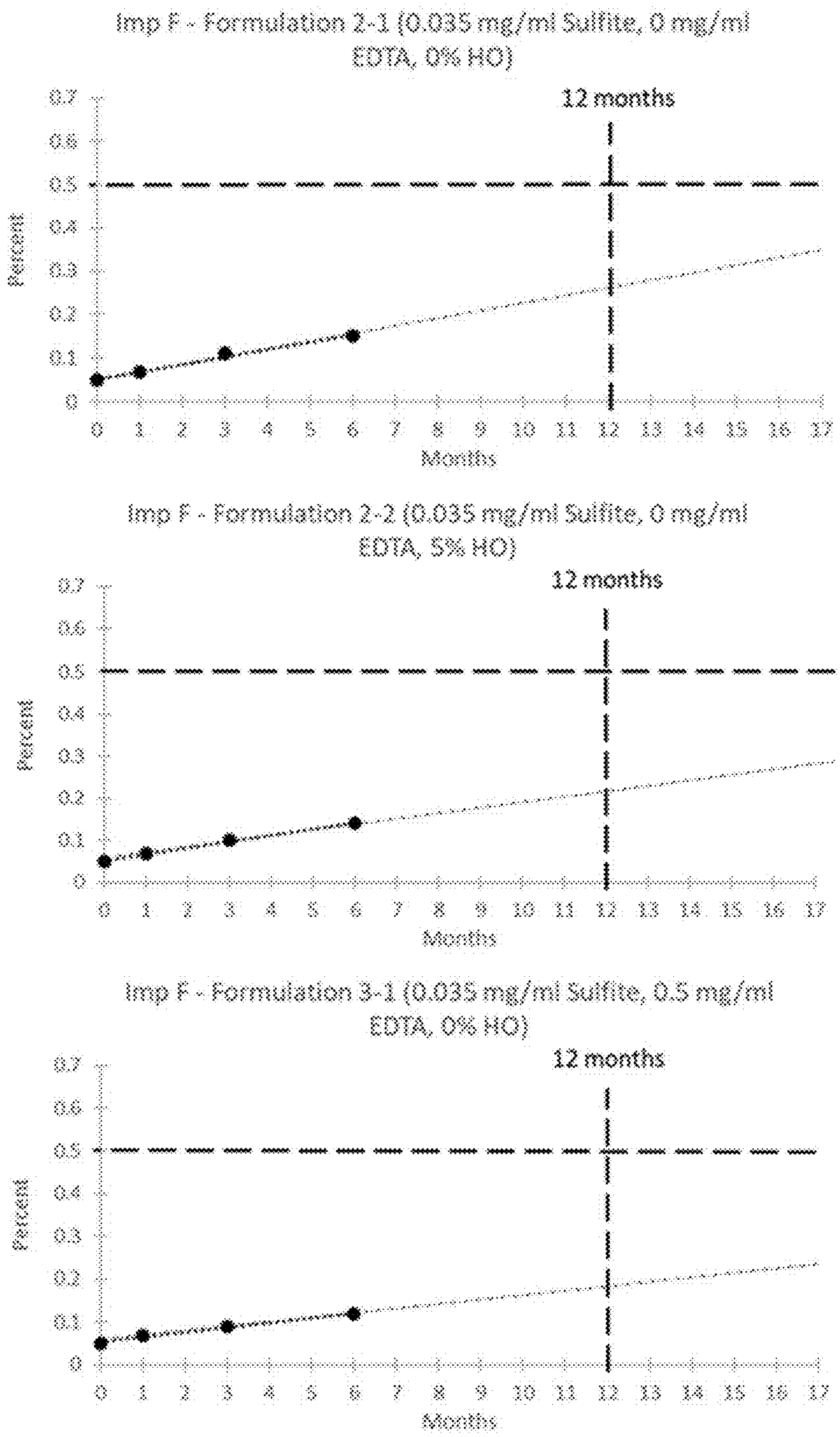

FIG. 41 demonstrates the Impurity F result and projection of the additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity F level is expected to be below 0.5% at 12 months (40° C./75% RH) for all 3 formulations.

Figure 42:
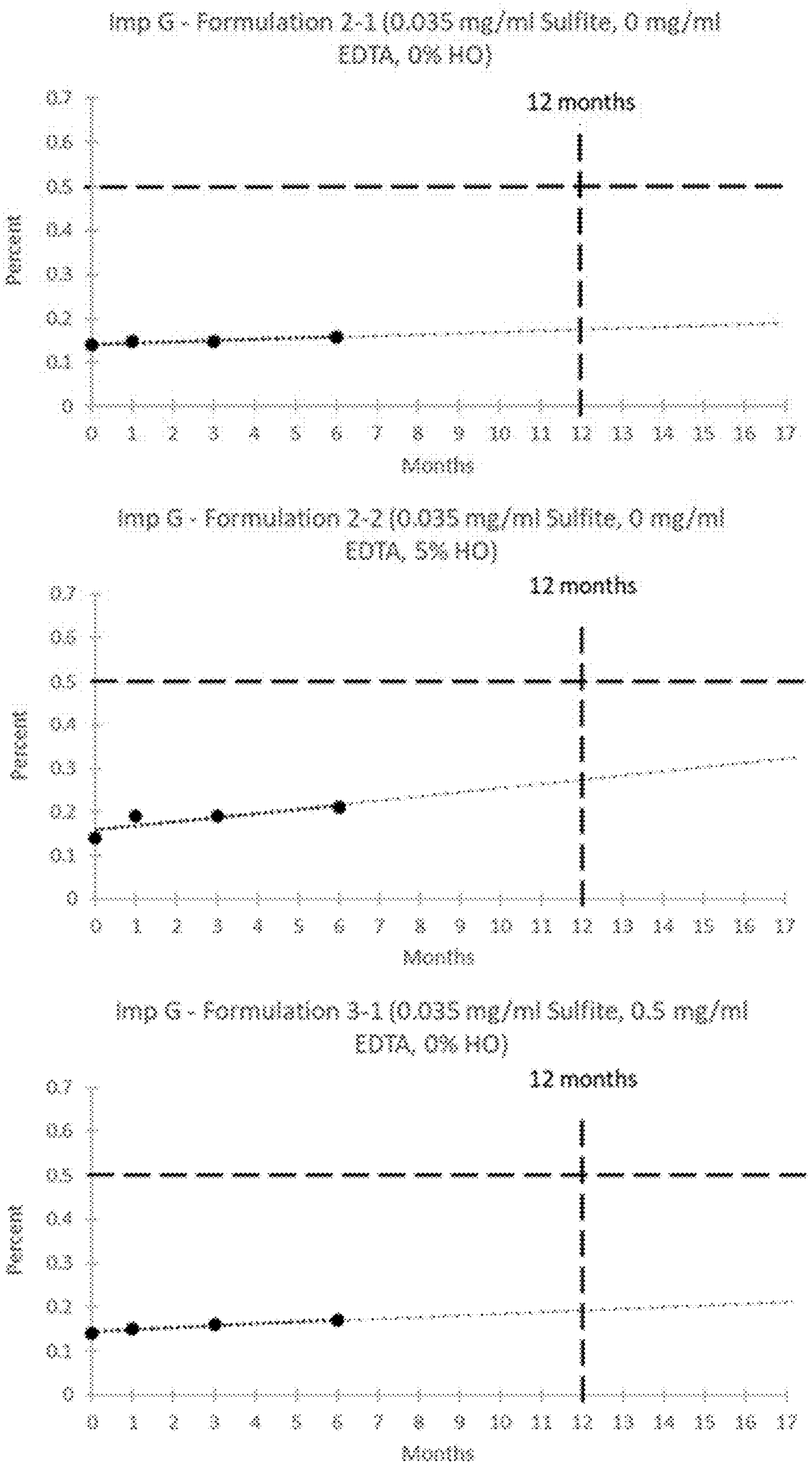

FIG. 42 demonstrates the Impurity G result and projection of the additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity G level is expected to be below 0.5% at 12 months (40° C./75% RH) for all 3 formulations.

FIG. 43 demonstrates the Unidentified Impurity result and projection of the additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the level of the Unidentified Impurity is expected to be below 0.5% at 12 months (40° C./75% RH) for all 3 formulations. Moreover, the two formulations lacking EDTA (2-1 and 2-2) show an expected level even below 0.2% at 12 months.

Figure 44:
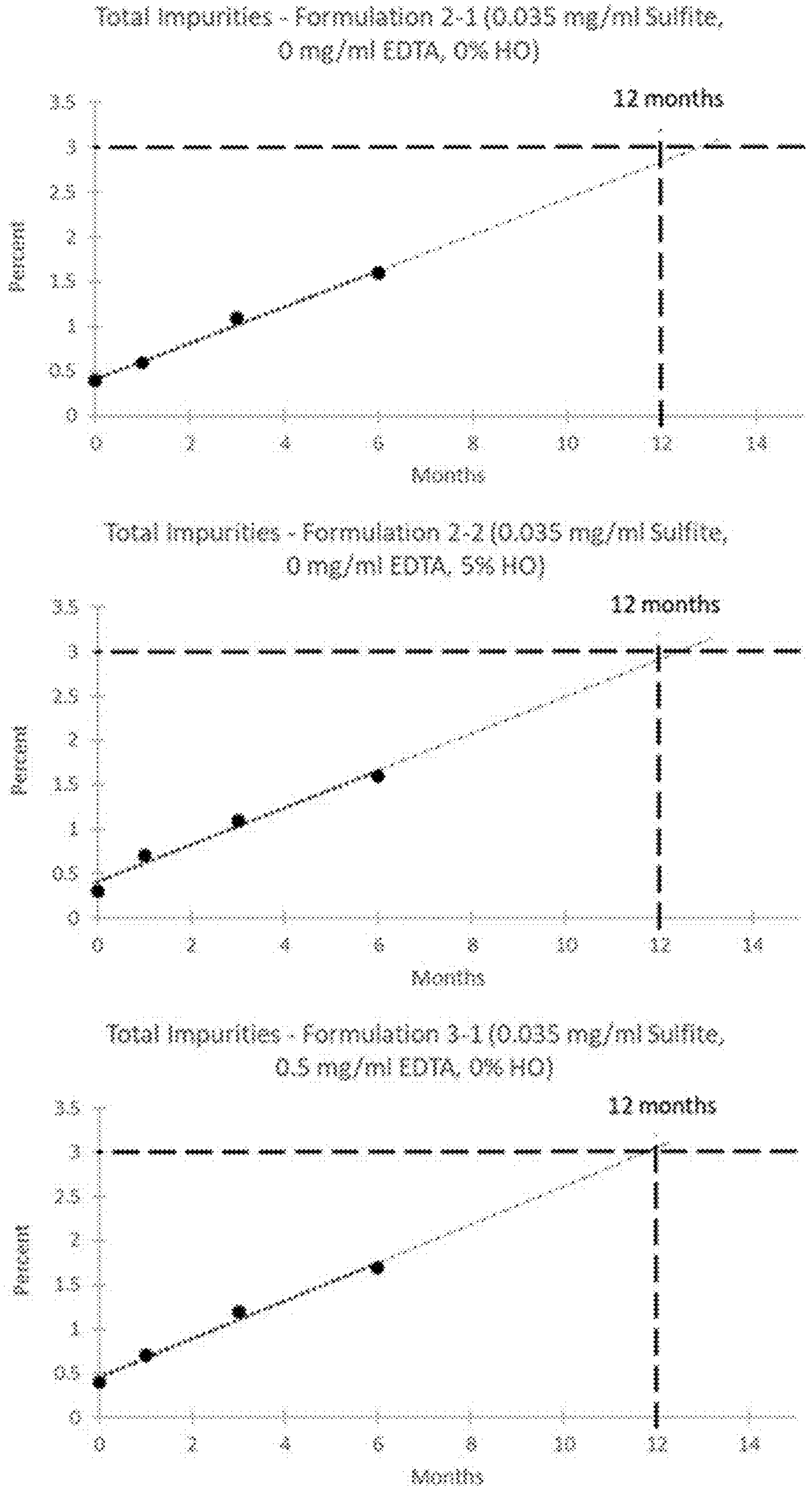

FIG. 44 demonstrates the Total Impurites result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the level of the Total Impurites is expected to be below 3% at 12 months (40° C./75% RH) for the two formulations lacking the EDTA (2-1, 2-2), while reaching 3% for the formulation 3-1 with sulfite and EDTA present. The result demonstrates that EDTA is not necessary to increase the stability of the formulation.

FIG. 45 demonstrates the results for the impurities A and C of the additional design of experiment for increasing concentrations of Dexamethasone Sodium Phosphate (DSP). Six formulations with 3 varying levels of DSP (10, 30 and 45 mg/ml) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. While there is a clear decrease of impurity C for all formulations over 6 months, there seems to be no clear trend for impurity A in the formulations including EDTA. For impurity A in the formulation lacking EDTA there is an initital increase visible that eventually stagnates, FIG. 46 demonstrates the results for the impurities D and G of the additional design of experiment for increasing concentrations of Dexamethasone Sodium Phosphate (DSP). Six formulations with 3 varying levels of DSP (10, 30 and 45 mg/ml) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. While there is a clear decrease of impurity G for all formulations over 6 months, there seems to be no clear trend for impurity D in the formulations lacking EDTA. For impurity D in the formulations including EDTA there is a visible increase over time up to ~0.2%.

FIG. 47 demonstrates the results for the Total Impurities of the additional design of experiment for increasing concentrations of Dexamethasone Sodium Phosphate (DSP).

Six formulations with 3 varying levels of DSP (10, 30 and 45 mg/ml) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. The formulations with the highest DSP content of 45 mg/ml still passed the description at 3 months, while all other failed and showed a precipitate. The result demonstrates that the formulations with an increasing DSP concentration form less total impurities over time, independent of the presence or absence of EDTA.

DETAILED DESCRIPTION

The present disclosure is directed to high concentration glucocorticoid containing pharmaceutical compositions comprising reduced levels of antioxidant acting preservatives. The present disclosure is based on the finding that use of a defined headspace volume to API ratio during distribution of the composition into packaging receptacles results in increased stability of the compositions in the presence of reduced levels of antioxidant preservatives. The pharmaceutical compositions of the present invention have several advantages over existing formulations. Given that antioxidant preservatives have been found to be associated with patient sensitivity and toxicity, pharmaceutical compositions comprising lower levels of such preservatives, while retaining stability of the composition at 2° C. to 40° C., is highly desirable.

That is, the present disclosure is directed to aqueous pharmaceutical formulations comprising a glucocorticoid. The aqueous pharmaceutical formulations comprise reduced levels of preservative, which may be antioxidant acting preservatives. The aqueous pharmaceutical formulations of the present invention have several advantages over existing formulations. Given that preservatives have been found to be associated with patient sensitivity and toxicity, pharmaceutical formulations comprising lower levels of such preservatives, while retaining stability of the formulation, are highly desirable.

The present invention is based in part on the finding that use of a defined headspace volume (ml) to glucocorticoid (mg) ratio during packaging of the formulation into containers results in increased stability of the formulation, even with reduced or no amount of preservative. Accordingly, in some embodiments of the aqueous pharmaceutical formulations comprising a glucocorticoid, the formulation is packaged in a container with a headspace volume (ml) to total glucocorticoid content (mg) ratio of 0.007 or less. In some embodiments the headspace volume (ml) to total glucocorticoid content (mg) ratio may be 0.0065 or less, 0.0060 or less, 0.00588 or less, 0.0055 or less, 0.0050 or less, 0.0045 or less, 0.0040 or less, 0.0035 or less, 0.0030 or less, 0.0025 or less, 0.0020 or less, 0.0015 or less, or 0.0010 or less. In some preferred embodiments, the headspace volume (ml) to total glucocorticoid content (mg) ratio may be 0.00588 or less.

In some embodiments of the aqueous pharmaceutical formulations comprising a glucocorticoid, the formulation is packaged in a container with a headspace volume (ml) to total glucocorticoid content (mg) ratio of between about 0.0046 to about 0.0099. In some embodiments the headspace volume (ml) to total glucocorticoid content (mg) ratio may be between about 0.003 and 0.007, or between about 0.004 and 0.006. In some embodiments the headspace volume (ml) to total glucocorticoid content (mg) ratio may be between about 0.001 and 0.00588.

Those skilled in the art can easily calculate equivalent concentrations of dexamethasone for a given glucocorticoid, as outlined in detail below. Accordingly, in some cases the headspace volume (ml) to total glucocorticoid content (mg) ratio may be expressed as a ratio of the headspace volume (ml) to glucocorticoid content (mg), wherein the glucocorticoid content is expressed as an equivalent content of dexamethasone (mg). That is, in some embodiments, the headspace volume (ml) to total glucocorticoid content (mg) ratio may be, or may be expressed as, a headspace volume (ml) to dexamethasone content (mg) ratio.

Means for determining headspace volume in a container are well known to those skilled in the art. For example, during packaging the headspace volume can be measured by the following calculation: (vial brim volume-stopper volume-fluid fill volume); or, by adding a liquid and measuring the volume when all gas has been replaced.

In some embodiments of the aqueous pharmaceutical formulations comprising a glucocorticoid, the formulation may be packaged in a container with a total sulfite content (mg) to total glucocorticoid content (mg) ratio of 0.0040 or less, 0.0035 or less, 0.0030 or less, 0.0025 or less, 0.0020 or less, 0.0015 or less, 0.00146 or less, or 0.0010 or less. In some preferred embodiments, the formulation may be packaged in a container with a total sulfite content (mg) to total glucocorticoid content (mg) ratio of 0.00150 or less. In some particularly preferred embodiments, the formulation may be packaged in a container with a total sulfite content (mg) to total glucocorticoid content (mg) ratio of 0.00146 or less.

In some embodiments of the aqueous pharmaceutical formulations comprising a glucocorticoid, the formulation may be packaged in a container with a sulfite content (mg):glucocorticoid content (mg):headspace volume (mg) ratio of 0.000203 or less.

In some embodiments of the aqueous pharmaceutical formulations comprising a glucocorticoid, the formulation may be packaged in a container with a ((sulfite (mg): glucocorticoid content (mg))×headspace volume (mg)) value of 0.01050 or less.

In some embodiments the headspace volume may be about 20, 19, 18, 17, 16, 15, 14, 13, 12, 11, 10, 9, 8, 7, 6, 5, 4, 3, 2, or 1 ml. In some embodiments the headspace volume may be less than about 20, 19, 18, 17, 16, 15, 14, 13, 12, 11, 10, 9, 8, 7, 6, 5, 4, 3, 2, or 1 ml. In some preferred embodiments the headspace volume may be or may be less than about 8 ml. In other preferred embodiments the headspace volume may be or may be less than about 7.2 ml.

In some embodiments, the headspace volume may be about 16, 15, 14, 13, 12, 11, 10, 9, 8, 7, 6, 5, 4, 3, 2, or 1% of the total container volume. In some embodiments, the headspace volume may be less than about 16, 15, 14, 13, 12, 11, 10, 9, 8, 7, 6, 5, 4, 3, 2, or 1% of the total container volume.

In some embodiments the headspace volume may comprise about 21, 20, 19, 18, 17, 16, 15, 14, 13, 12, 11, 10, 9, 8, 7, 6, 5, 4, 3, 2, or 1% oxygen. In some embodiments the headspace volume may comprise less than about 21, 20, 19, 18, 17, 16, 15, 14, 13, 12, 11, 10, 9, 8, 7, 6, 5, 4, 3, 2, or 1% oxygen. In some preferred embodiments the headspace volume may comprise about 5% oxygen or may comprise less than about 5% oxygen. In other preferred embodiments the headspace volume may comprise about 0% oxygen.

Means for determining headspace oxygen levels in a given headspace volume are well known to those skilled in the art. For example, headspace oxygen levels may be measured by conventional destructive techniques, such as electrochemical methods or gas chromatography, or by non-destructive methods such as laser-based Frequency Modulation Spectroscopy (Pharmaceutical Technology, July 2002; Lighthouse Instruments Application Note 102).

The aqueous pharmaceutical formulations of the invention advantageously comprise lower amounts of preservative (such as an antioxidant or antimicrobial) than known glucocorticoid formulations. Accordingly, in some embodiments, the formulation may (or may not) comprise a pharmaceutically acceptable preservative. In some embodiments, the formulation may comprise a sulfite preservative present in a concentration of less than about 1 mg/ml; a paraben preservative present in a concentration of less than about 0.2 mg/ml; creatinine present in a concentration of less than about 8 mg/ml; and/or benzethonium chloride present in a concentration of less than about 0.1 mg/ml. In some preferred embodiments, the total concentration of preservative in the formulation may be less than about 0.1 mg/ml.

In some embodiments, the concentration of preservative may be about 0.09 mg/ml, about 0.08 mg/ml, about 0.07 mg/ml, about 0.06 mg/ml, about 0.05 mg/ml, about 0.04 mg/ml, about 0.035 mg/ml, about 0.03 mg/ml, about 0.02 mg/ml, or about 0.01 mg/ml. In some embodiments, the concentration of preservative may be less than about 0.09 mg/ml, less than about 0.08 mg/ml, less than about 0.07 mg/ml, less than about 0.06 mg/ml, less than about 0.05 mg/ml, less than about 0.04 mg/ml, less than about 0.035 mg/ml, less than about 0.03 mg/ml, less than about 0.02 mg/ml, or less than about 0.01 mg/ml. In some preferred embodiments, the concentration of preservative may be about 0.07 mg/ml, or may be less than about 0.07 mg/ml. In other preferred embodiments, the concentration of preservative may be about 0.035 mg/ml, or may be less than about 0.035 mg/ml.

In some particularly preferred embodiments the concentration of preservative may be 0 mg/ml. That is, in some particularly preferred embodiments the formulation does not comprise a preservative.

As outlined above, the pharmaceutical formulations of the invention may (or may not) comprise a pharmaceutically acceptable preservative (such as an antioxidant or antimicrobial) additive to maintain the stability of the formulation. Antioxidants are added in amounts that are reduced as compared to levels typically employed in known glucocorticoid containing formulations—thereby reducing the toxicity and adverse side effects associated with use of such antioxidant preservatives.

As used herein, antioxidants (antioxidant preservatives) are those excipients known to those skilled in the art to delay or inhibit the oxidation process of molecules, thereby increasing the stability of the composition. Such antioxidants include, but are not limited to, ascorbic acid, acetylcysteine, butylhydroxyanisol, cysteine hydrochloride, dithionite sodium, gentisic acid, glutamate monosodium, glutathione, formaldehyde sulfoxylate sodium, methionine, monothioglycerol, propyl gallate, sulfites, sodium thioglycolate, α-thioglycerol, tocopherol alpha, alpha tocopherol hydrogen succinate, vitamin A, vitamin C, vitamin E, beta-carotene, lycopene, lutein, selenium, manganese, zeaxanthin, flavonoids, flavones, catechins, polyphenols, and phytoestrogens, and thioglycolate sodium. In some cases the antioxidant (antioxidant preservative) is a sulfite. Such sulfites relate to, but are not limited to, sodium sulfite (anhydrous) ($Na_2SO_3$), sodium bisulfite ($NaHSO_3$), potassium bisulfite ($KHSO_3$), potassium metabisulfite ($K_2S_2O_5$) and sodium metabisulfite ($Na_2S_2O_5$).

Thus, in some embodiments of the pharmaceutical formulations of the invention, the preservative may be a sulfite, a paraben, benzyl alcohol, benzethonium chloride, propylene glycol, and/or creatinine. In some embodiments, the sulfite may be sodium sulfite (anhydrous), sodium bisulfite, sodium metabisulfite, potassium bisulfite, and/or potassium metabisulfite. In some embodiments, the paraben may be methylparaben, propylparaben, ethylparaben, butylparaben, isopropylparaben and/or isobutylparaben. In some embodiments, the paraben may be methylparaben and/or propylparaben.

In some embodiments, the concentration of sulfite preservative may be about 1 mg/ml or less than about 1 mg/ml. In some embodiments, the concentration of sulfite preservative may be about 0.9 mg/ml, about 0.8 mg/ml, about 0.7 mg/ml, about 0.6 mg/ml, about 0.5 mg/ml, about 0.4 mg/ml, about 0.3 mg/ml, about 0.2 mg/ml, or about 0.1 mg/ml. In some embodiments, the concentration of sulfite preservative may be less than about 0.9 mg/ml, less than about 0.8 mg/ml, less than about 0.7 mg/ml, less than about 0.6 mg/ml, less than about 0.5 mg/ml, less than about 0.4 mg/ml, less than about 0.3 mg/ml, less than about 0.2 mg/ml, or less than about 0.1 mg/ml. In some embodiments, the concentration of sulfite preservative may be about 0.09 mg/ml, about 0.08 mg/ml, about 0.07 mg/ml, about 0.06 mg/ml, about 0.05 mg/ml, about 0.04 mg/ml, about 0.03 mg/ml, about 0.02 mg/ml, or about 0.01 mg/ml. In some embodiments, the concentration of sulfite preservative may be less than about 0.09 mg/ml, less than about 0.08 mg/ml, less than about 0.07 mg/ml, less than about 0.06 mg/ml, less than about 0.05 mg/ml, less than about 0.04 mg/ml, less than about 0.03 mg/ml, less than about 0.02 mg/ml, or less than about 0.01 mg/ml. In some preferred embodiments the concentration of sulfite preservative may be 0 mg/ml. That is, in some preferred embodiments the formulation does not comprise a sulfite preservative.

In some embodiments, the concentration of paraben preservative may be about 0.2 mg/ml or less than about 0.2 mg/ml. In some embodiments, the concentration of paraben preservative may be about 0.1 mg/ml or less than about 0.1 mg/ml. In some embodiments, the concentration of paraben preservative may be about 0.09 mg/ml, about 0.08 mg/ml, about 0.07 mg/ml, about 0.06 mg/ml, about 0.05 mg/ml, about 0.04 mg/ml, about 0.03 mg/ml, about 0.02 mg/ml, or about 0.01 mg/ml. In some embodiments, the concentration of paraben preservative may be less than about 0.09 mg/ml, less than about 0.08 mg/ml, less than about 0.07 mg/ml, less than about 0.06 mg/ml, less than about 0.05 mg/ml, less than about 0.04 mg/ml, less than about 0.03 mg/ml, less than about 0.02 mg/ml, or less than about 0.01 mg/ml. In some preferred embodiments the concentration of paraben preservative may be 0 mg/ml. That is, in some preferred embodiments the formulation does not comprise a paraben preservative.

In some embodiments, the concentration of creatinine may be about 8 mg/ml, or may be less than about 8 mg/ml. In some embodiments, the concentration of creatinine may be about 7 mg/ml, about 6 mg/ml, about 5 mg/ml, about 4 mg/ml, about 3 mg/ml, about 2 mg/ml, or about 1 mg/ml. In some embodiments, the concentration of creatinine may be less than about 7 mg/ml, less than about 6 mg/ml, less than about 5 mg/ml, less than about 4 mg/ml, less than about 3 mg/ml, less than about 2 mg/ml, or less than about 1 mg/ml. In some embodiments, the concentration of creatinine may be about 0.9 mg/ml, about 0.8 mg/ml, about 0.7 mg/ml, about 0.6 mg/ml, about 0.5 mg/ml, about 0.4 mg/ml, about 0.3 mg/ml, about 0.2 mg/ml, or about 0.1 mg/ml. In some embodiments, the concentration of creatinine may be less than about 0.9 mg/ml, less than about 0.8 mg/ml, less than about 0.7 mg/ml, less than about 0.6 mg/ml, less than about 0.5 mg/ml, less than about 0.4 mg/ml, less than about 0.3 mg/ml, less than about 0.2 mg/ml, or less than about 0.1 mg/ml. In some embodiments, the concentration of creatinine may be about 0.09 mg/ml, about 0.08 mg/ml, about 0.07 mg/ml, about 0.06 mg/ml, about 0.05 mg/ml, about 0.04 mg/ml, about 0.03 mg/ml, about 0.02 mg/ml, or about 0.01 mg/ml. In some embodiments, the concentration of creatinine may be less than about 0.09 mg/ml, less than about 0.08 mg/ml, less than about 0.07 mg/ml, less than about 0.06 mg/ml, less than about 0.05 mg/ml, less than about 0.04 mg/ml, less than about 0.03 mg/ml, less than about 0.02 mg/ml, or less than about 0.01 mg/ml. In some preferred embodiments the concentration of creatinine may be 0 mg/ml. That is, in some preferred embodiments the formulation does not comprise creatinine.

In some embodiments, the concentration of benzethonium chloride may be about 0.1 mg/ml or less than about 0.1 mg/ml. In some embodiments, the concentration of benzethonium chloride may be about 0.09 mg/ml, about 0.08 mg/ml, about 0.07 mg/ml, about 0.06 mg/ml, about 0.05 mg/ml, about 0.04 mg/ml, about 0.03 mg/ml, about 0.02 mg/ml, or about 0.01 mg/ml. In some embodiments, the concentration of benzethonium chloride may be less than about 0.09 mg/ml, less than about 0.08 mg/ml, less than about 0.07 mg/ml, less than about 0.06 mg/ml, less than about 0.05 mg/ml, less than about 0.04 mg/ml, less than about 0.03 mg/ml, less than about 0.02 mg/ml, or less than about 0.01 mg/ml. In some preferred embodiments the concentration of benzethonium chloride may be 0 mg/ml. That is, in some preferred embodiments the formulation does not comprise benzethonium chloride.

The aqueous pharmaceutical formulations of the invention may advantageously comprise lower amounts of a chelating agent than known glucocorticoid formulations. Chelating agents are commonly included in pharmaceutical formulations to sequester and decrease the reactivity of metal ions that may be present in the formulation.

Accordingly, in some embodiments, the formulations of the invention may (or may not) comprise a chelating agent. In some embodiments, the formulation may comprise a chelating agent, wherein the concentration of chelating agent is or is less than about 0.50 mg/ml. In some embodiments the concentration of chelating agent may be about 0.45 mg/ml, about 0.40 mg/ml, about 0.35 mg/ml, about 0.30 mg/ml, about 0.25 mg/ml, about 0.20 mg/ml, about 0.15 mg/ml, about 0.10 mg/ml, or about 0.05 mg/ml. In some embodiments the concentration of chelating agent may be less than about 0.45 mg/ml, less than about 0.40 mg/ml, less than about 0.35 mg/ml, less than about 0.30 mg/ml, less than about 0.25 mg/ml, less than about 0.20 mg/ml, less than about 0.15 mg/ml, less than about 0.10 mg/ml, or less than about 0.05 mg/ml. In some preferred embodiments the concentration of chelating agent may be 0 mg/ml. That is, in some preferred embodiments the formulation does not comprise a chelating agent. In some preferred embodiments the formulation does not comprise disodium edetate (disodium EDTA).

Possible chelating agents include, but are not limited to, calcium disodium EDTA 0.01-0.1% (EDTA=Ethylenediaminetetra acetic acid or Edetate), Disodium EDTA 0.01-0.11%, Sodium EDTA 0.20%, Calcium Versetamide Sodium 2.84%, Calteridol 0.023%, and DTPA 0.04-1.2% (Diethylenetriaminepenta acetic acid). Other chelating agents include, but are not limited to, acetic acid, citric acid, ascorbic acid, lactic acid, edetic acid, nitriloacetic acid, dipicolinic acid, gadoteric acid, pentetic acid, gluconic acid, L-tartaric acid, thiosulfuric acid, emeramide, poliglusam, acteoside, thenoyltrifluoroacetone, tagatose, tetrathiomolybdate, alanosine, dimercaprol, triethyltetramine, deferiprone, calcium acetate, succimer, sevelamer, deferoxamine, penicillamine, tolevamer, deferasirox, 1,10-phenanthroline, and ditiocarb. In some embodiments, the chelating agent may be one or more of these. In some embodiments, the chelating agent may be ethylenediamine, ethylenediaminetetraacetic acid (EDTA), sodium edetate, disodium edetate, tetrasodium edetate, calcium disodium edetate, calcium versetamide sodium, calteridol, and/or diethylenetriaminepenta acetic acid (DPTA). In some preferred embodiments, the chelating agent may be disodium edetate (disodium EDTA).

As used herein, the term glucocorticoid includes glucocorticoid receptor agonists and any compound that binds to the glucocorticoid receptor. Such compounds relate to, but are not limited to, dexamethasone, dexamethasone containing agents, hydrocortisone, methylprednisolone, prednisone, prednisolone, prednylidene, cortisone, budesonide, betamethasone and beclomethasone. Other glucocorticoids include mometasone furoate, Triamcinolone Acetonide and methylprednisone. Glucocorticoids further include glucocorticoid receptor modulating agonists. Additionally, selective glucocorticoid receptor agonists or modulators may be used in the pharmaceutical formulations disclosed herein. Such agonists or modulators include for example, selective glucocorticoid receptor modulators (SEGRMs) and selective glucocorticoid receptor agonists (SEGRAs). Glucocorticoids, glucocorticoid receptor modulators and selective glucocorticoid receptor agonists (SEGRAs) that may be utilized in the herein disclosed formulations and methods are well known to those skilled in the art.

The term glucocorticoid-receptor modulating agents as used herein non-exclusively relates to glucocorticoid receptor agonists or glucocorticoid receptor modulators including but not limited to: compound A [CpdA; (2-((4-acetophenyl)-2-chloro-N-methyl)ethylammoniumchloride)] and N-(4-methyl-1-oxo-1H-2,3-benzoxazine-6-yl)-4-(2,3-dihydrobenzofuran-7-yl)-2-hydroxy-2 (trifluoromethyl)-4-methylpentanamide (ZK216348), AL-438, Mapracorat, LGD-5552, RU 24858, Fosdagrocorat, PF-802, Compound 10, MK5932, C108297, LGD5552, and ORG 214007-0.

Glucocorticoids and glucocorticoid-receptor (GR) modulating agents exert their effects through both membrane glucocorticoid receptors and cytoplasmic GRs which activate or repress gene expression. Some of the desirable lymphodepletion effects of the glucocorticoids and GR modulating agents appear to be mediated via membrane GRs or other non-genomic effects in addition to their genomic effects. Interestingly, co-treatment with dexamethasone has been shown to be able to reduce glucocorticoid resistance (Serafin et al., 2017).

In some embodiments of the aqueous pharmaceutical formulations comprising a glucocorticoid, the glucocorticoid is selected from the group consisting of dexamethasone, hydrocortisone, methylprednisolone, prednisone, prednisolone, prednylidene, cortisone, budesonide, betamethasone and beclomethasone. In some preferred embodiments the glucocorticoid comprises dexamethasone, which may be selected from the group consisting of dexamethasone base, dexamethasone sodium phosphate, dexamethasone hemisuccinate, dexamethasone sodium succinate, dexamethasone succinate, and dexamethasone acetate. In some preferred embodiments the glucocorticoid is dexamethasone sodium phosphate. In some preferred embodiments the glucocorticoid is dexamethasone having the following formula (dexamethasone phosphate (as sodium)):

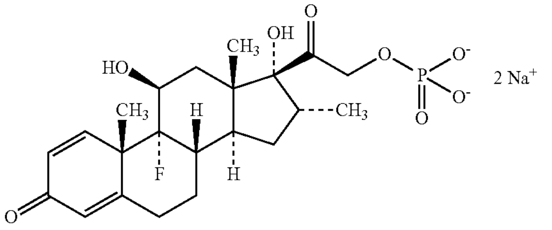

Dexamethasone phosphate (as sodium) is a white or slightly yellow, very hygroscopic, crystalline powder. It is odourless or has a slight odour of alcohol. Dexamethasone phosphate (as sodium) is soluble 1 in 2 in water, slightly soluble in alcohol, practically insoluble in chloroform and ether, and very slightly soluble in dioxan.

The present invention is based in part on the finding that the glucocorticoid Dexamethasone Sodium Phosphate (DSP), when present in high concentrations in an aqueous formulation, is increasingly self-protective against degradative processes like hydrolyzation and oxidization. Accordingly, in some embodiments of the aqueous pharmaceutical formulations comprising a glucocorticoid, the concentration of glucocorticoid may be about 10, 11, 12, 13, 14, 15, 16, 17, 18, 19, 20, 21, 22, 23, 24, 25, 26, 26.23, 27, 28, 29, 30, 31, 32, 33, 34, 35, 36, 37, 38, 39, 40, 41, 42, 43, 44, or 45 mg/ml. In some embodiments, the concentration of glucocorticoid may be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 mg/ml. In some particularly preferred embodiments the concentration of glucocorticoid may be about 24 mg/ml, or may be at least about 24 mg/ml. In other preferred embodiments the concentration of glucocorticoid may be about 26.23 mg/ml, or may be at least about 26.23 mg/ml. In other preferred embodiments the concentration of glucocorticoid may be about 30 mg/ml, or may be at least about 30 mg/ml. In other preferred embodiments the concentration of glucocorticoid may be about 45 mg/ml, or may be at least about 45 mg/ml.

In some embodiments of the aqueous pharmaceutical formulations comprising a glucocorticoid, the concentration of glucocorticoid may be less than about 500, 457, 450, 400, 350, 300, 250, 200, 150, or 100 mg/ml. In some preferred embodiments, the concentration of glucocorticoid may be less than about 457 mg/ml. In other preferred embodiments, the concentration of glucocorticoid may be less than about 250 mg/ml.

Those skilled in the art can easily calculate equivalent concentrations of glucocorticoids or glucocorticoid receptor modulating agents, for example using publicly available corticoid conversion algorithms. Those skilled in the art know, for example, that 10, 26.23, 30 and 45 mg/ml of dexamethasone sodium phosphate (DSP) is equivalent to 9.15, 24, 27.45 and 41.17 mg/ml respectively of dexamethsone phosphate (DP). Similarly, 26.23 and 45 mg/ml of dexamethasone sodium phosphate (DSP) is equivalent to 19.94 and 34.2 mg/ml respectively of dexamethasone. Thus, in some cases, the concentration of a glucocorticoid may be expressed as a concentration equivalent to a given concentration of another glucocorticoid—e.g., "a concentration equivalent to a given concentration of dexamethasone". For example, 9.15 mg/ml of dexamethsone phosphate may be alternatively expressed as "a concentration of dexamethsone phosphate equivalent to 10 mg/ml of dexamethasone sodium phosphate" and vice versa. As another example, 34.2 mg/ml of dexamethasone may be alternatively expressed as "a concentration of dexamethsone equivalent to 45 mg/ml of dexamethasone sodium phosphate".

In some embodiments, the concentration of glucocorticoid may be between about 4.4 mg/ml to about 1000 mg/ml. In some embodiments the glucocorticoid is dexamethasone phosphate in a concentration between about 4.4 mg/ml and about 457 mg/ml DP (dexamethasone phosphate), more preferably between about 24 mg/ml and about 457 mg/ml DP). In some embodiments the glucocorticoid is dexamethasone phosphate in a concentration between about 24 mg/ml and about 450 mg/ml DP, between about 24 mg/ml and about 400 mg/ml DP, between about 24 mg/ml and about 350 mg/ml DP, between about 24 mg/ml and about 300 mg/ml DP, more preferably between about 24 mg/ml and about 250 mg/ml DP.

In some embodiments, the pH of the formulation may be between about 7.0 to about 8.2, about 7.2 to about 8.0, about 7.3 to about 7.9, or between about 7.4 to about 7.8, In some preferred embodiments, the pH of the formulation may be between about 7.4 to about 7.8. In some preferred embodiments, the pH of the formulation may be about 7.6.

In addition to the glucocorticoid, preservative (which may be an antioxidant preservative), and chelating agent outlined above, additional components well known to those of skill in the art may be included in the pharmaceutical formulations of the invention. Pharmaceutical formulations may be prepared using a pharmaceutically acceptable "carrier" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In some embodiments, this term refers to molecular entities and compositions approved by a regulatory agency of the US federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

The term "carrier" relates to, but is not limited to, diluents, binders, lubricants, and disintegrants. Those with skill in the art are familiar with such pharmaceutical carriers and methods of compounding pharmaceutical compositions and formulations using such carriers.

The pharmaceutical formulations of the invention may (or may not) include one or more excipients, e.g., solvents, solubility enhancers, suspending agents, buffering agents, isotonicity agents, stabilizers, and antioxidants or antimicrobial preservatives. The IID lists the highest amount of the excipient per unit dose in each dosage form in which it is used. The amounts shown for maximum potency do not reflect the maximum daily intake (MDI) of the excipient unless the maximum daily dose of the product that is the basis for the listing is only a single unit. When used, the excipients of the compositions will not adversely affect the stability, bioavailability, safety, and/or efficacy of the active ingredients, i.e., glucocorticoids, used in the formulation. Thus, formulations are provided wherein there is no incompatibility between any of the components of the dosage form. Excipients may be selected from the group consisting of buffering agents, solubilizing agents, tonicity agents, chelating agents, antioxidants, antimicrobial agents, and preservatives. In some embodiments, the pharmaceutical formulations may comprise a buffer (buffering agent). In some embodiments, the buffer may be sodium citrate. In some preferred embodiments, the concentration of buffer may be about 10 mg/ml.

The present disclosure is based in part on the finding that use of a defined headspace volume (ml) to glucocorticoid (mg) ratio during the packaging of the formulation into a container results in a maintained stability of the formulation close to its state directly after manufacture. In some embodiments the container may be a vial, ampoule, solvent reservoir, storage bottle, medical bottle, syringe, or bottle.

Those skilled in the art will appreciate that formulations packaged in smaller volumes are easier to stabilize, and therefore require less preservative. For example, formulations packaged in smaller volumes are easier to stabilize against oxygen (oxidative degradation). Surprisingly, use of the defined headspace volume (ml) to glucocorticoid (mg) ratio of the present invention results in increased stability of aqueous formulations, with reduced or no amount of preservative, even in large volume containers. Accordingly, in some embodiments, the volume of the container may be about 1, 2, 3, 4, 5, 6, 7, 8, 9, 10, 15, 20, 25, 30, 35, 40, 45, 50, 51, 55, 60, 65, 70, 75, 80, 85, 90, 95, or 100 ml. In some embodiments, the volume of the container may be at least about 1, 2, 3, 4, 5, 6, 7, 8, 9, 10, 15, 20, 25, 30, 35, 40, 45, 50, 51, 55, 60, 65, 70, 75, 80, 85, 90, 95, or 100 ml. In some preferred embodiments, the volume of the container may be about 59 ml, or may be at least about 59 ml. In some preferred embodiments, the volume of the container may be about 51 ml, or may be at least about 51 ml. In other preferred embodiments, the volume of the container may be about 50 ml, or may be at least about 50 ml. In some embodiments the volume of pharmaceutical formulation packaged in the container may be at least about 1, 2, 3, 4, 5, 6, 7, 8, 9, 10, 15, 20, 25, 30, 35, 40, 45, 50, 55, 60, 65, 70, 75, 80, 85, 90, 95, or 100 ml. In some preferred embodiments the volume of pharmaceutical formulation packaged in the container may be about 43 ml, or may be at least about 43 ml. In some preferred embodiments the volume of pharmaceutical formulation packaged in the container may be about 50 ml, or may be at least about 50 ml. In some preferred embodiments the volume of pharmaceutical formulation packaged in the container may be about 51 ml, or may be at least about 51 ml.

The aqueous pharmaceutical formulations of the invention advantageously comprise low or no amounts of preservative and/or chelating agent while retaining comparable stability to known preservative-containing glucocorticoid formulations.

Accordingly, in some embodiments the aqueous pharmaceutical formulations of the invention remain stable for at least about 18, 24, 36, or 48 months following manufacture. In some embodiments the aqueous pharmaceutical formulations remain stable for at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months following manufacture. Accordingly, stability of the formulation may be assessed at 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months after manufacture. In some preferred embodiments, stability of the formulation may be assessed at 18, 24, 36, or 48 months after manufacture.

In some embodiments the aqueous pharmaceutical formulations have a shelf-life of at least about 18, 24, 36, or 48 months following manufacture. In some embodiments the aqueous pharmaceutical formulations have a shelf-life of at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months following manufacture.

Means for determining stability and shelf-life of aqueous pharmaceutical formulations comprising a glucocorticoid are well known to those skilled in the art. For example, stability and shelf-life of a formulation may be determined by assaying quantitative chemical attributes of the formulation such as levels of the glucocorticoid API or its degradation products.

In some embodiments, stability is determined following storage of the formulation between 2° C. to 40° C. In some embodiments, stability is determined following storage of the formulation between 15° C. to 40° C. In some preferred embodiments, stability is determined following storage of the formulation between 20° C. to 40° C. In some preferred embodiments, stability is determined following storage of the formulation between 15° C. to 20° C. In some preferred embodiments, stability is determined following storage of the formulation at room temperature. In some preferred embodiments, stability is determined following storage of the formulation at 25° C. In some preferred embodiments, stability is determined following storage of the formulation at 40° C.

In some embodiments, stability is determined following storage of the formulation between 40 to 80% relative humidity (RH). In some embodiments, stability is determined following storage of the formulation between 50 to 70% RH. In some preferred embodiments, stability is determined following storage of the formulation at 60% RH. In some preferred embodiments, stability is determined following storage of the formulation at 75% RH. In some preferred embodiments, stability is determined following storage of the formulation at 25° C., 60% RH. In some preferred embodiments, stability is determined following storage of the formulation at 40° C., 75% RH.

In some embodiments, stability is determined by determining the degree of degradation of the glucocorticoid API in the formulation. Means for determining the amount of glucocorticoid API in a formulation are well known to those skilled in the art—for example, high performance liquid chromatography coupled to UV spectrometry (HPLC-UV) methods, or ultra performance liquid chromatography (UPLC) methods. In some embodiments, the formulation exhibits less than about 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0% degradation of the glucocorticoid API. In some preferred embodiments, the formulation exhibits less than about 5.0% degradation of the glucocorticoid API.

In some embodiments, the amount of glucocorticoid in the formulation is maintained above about 95.0, 95.2, 95.4, 95.6, 96.0, 96.2, 96.4, 96.6, 96.8, 97.0, 97.2, 97.4, 97.6, 98.0, 98.2, 98.4, 98.6, 98.8, 99.0, 99.1, 99.2, 99.3, 99.4, 99.5, 99.6, 99.7, 99.8, or 99.9% as compared to the date of manufacture. In some preferred embodiments, the amount of glucocorticoid in the formulation is maintained above about 95.0% as compared to the date of manufacture.

In some embodiments, the amount of glucocorticoid in the formulation is maintained between about ±1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% as compared to the date of manufacture. In some preferred embodiments, the amount of glucocorticoid in the formulation is maintained between about ±5.0% as compared to the date of manufacture.

In some embodiments, stability is determined by determining the degree of change in pH of the formulation.

Means for determining the pH of a formulation are well known to those skilled in the art. In some embodiments, the formulation exhibits less than about ±0.1, 0.2, 0.3, 0.4, 0.5, 0.6, 0.7, 0.8, 0.9, 1.0, 1.2, 1.4, 1.6, 1.8, or 2.0 change in pH. In some preferred embodiments, the formulation exhibits less than about ±0.5 change in pH. In some preferred embodiments, the formulation exhibits less than about ±0.2 change in pH.

In some embodiments, the glucocorticoid is dexamethasone sodium phosphate and stability is determined by determining the degree of accumulation of impurity A (9-fluoro-11β,17,21-trihydroxy-16α-methylpregna-1,4-3,20-dione (dexamethasone)) in the formulation. Means for determining the amount of impurity A in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity A. In some preferred embodiments, the formulation exhibits less than about 0.50% accumulation of impurity A. In other preferred embodiments, the formulation exhibits less than about 1.0% accumulation of impurity A.

In some embodiments, the glucocorticoid is dexamethasone sodium phosphate and stability is determined by determining the degree of accumulation of impurity B (9-fluoro-11β,17-dihydroxy-16β-methyl-3,20-dioxopregna-1,4-dien-21-yl dihydrogen phosphate (betamethasone phosphate)) in the formulation. Means for determining the amount of impurity B in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity B. In some preferred embodiments, the formulation exhibits less than about 0.50% accumulation of impurity B.

In some embodiments, the glucocorticoid is dexamethasone sodium phosphate and stability is determined by determining the degree of accumulation of impurity C in the formulation. Means for determining the amount of impurity C in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity C. In some preferred embodiments, the formulation exhibits less than about 0.50% accumulation of impurity C.

In some embodiments, the glucocorticoid is dexamethasone sodium phosphate and stability is determined by determining the degree of accumulation of impurity D in the formulation. Means for determining the amount of impurity D in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity D. In some preferred embodiments, the formulation exhibits less than about 0.50% accumulation of impurity D.

In some embodiments, the glucocorticoid is dexamethasone sodium phosphate and stability is determined by determining the degree of accumulation of impurity E in the formulation. Means for determining the amount of impurity E in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity E. In some preferred embodiments, the formulation exhibits less than about 0.50% accumulation of impurity E.

In some embodiments, the glucocorticoid is dexamethasone sodium phosphate and stability is determined by determining the degree of accumulation of impurity F in the formulation. Means for determining the amount of impurity F in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity F. In some preferred embodiments, the formulation exhibits less than about 0.50% accumulation of impurity F.

In some embodiments, the glucocorticoid is dexamethasone sodium phosphate and stability is determined by determining the degree of accumulation of impurity G in the formulation. Means for determining the amount of impurity G (9-fluoro-11β,17-dihydroxy-16α-methyl-3-oxoandrosta-1,4-diene-17β-carboxylic acid) in a formulation are well known to those skilled in the art. In some embodiments, the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity G. In some preferred embodiments, the formulation exhibits less than about 0.50% accumulation of impurity G.

In some embodiments, stability is determined by determining the degree of accumulation of unspecified impurities in the formulation. Means for determining the amount of unspecified impurities in a formulation are well known to those skilled in the art. In some embodiments, the formulation exhibits less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19 0.20, 0.21, 0.22, 0.23, 0.24, 0.25, 0.26, 0.27, 0.28, 0.29, or 0.30% accumulation of unspecified impurities. In some preferred embodiments, the formulation exhibits less than about 0.20% accumulation of unspecified impurities.

In some embodiments, stability is determined by determining the degree of accumulation of total impurities in the formulation. Means for determining the amount of total impurities in a formulation are well known to those skilled in the art. In some embodiments, the formulation exhibits less than about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% accumulation of total impurities. In some preferred embodiments, the formulation exhibits less than about 3.0% accumulation of total impurities.

Some specific embodiments of the aqueous pharmaceutical formulations of the invention are as follows.

In some embodiments, the stability achieved by the composition may be such that the DSP assay is maintained at 94% or higher, preferably 97% or higher, after storage at 25 degree Celsius and 60% RH for 24 months, or for 29 months. In some embodiments, the stability achieved by the composition may be such that the DSP assay is maintained at 94% or higher, preferably 96% or higher, more preferably 97% or higher, after storage at 40 degree Celsius and 75% RH for 6 months. In some embodiments, the stability achieved by the composition may be such that the level of Impurity A remains not more than 0.35%, preferably below 0.25%, more preferably below 0.20% after storage at 25 degree Celsius and 60% RH for 24 months, or for 29 months.

In some embodiments, the stability achieved by the composition may be such that the level of Impurity A (impurity A (dexamethasone)) remains no greater than 2.0% and below 1.5%, preferably below 0.9%, more preferably below 0.8%, after storage at 40 degree Celsius and 75% RH for 6 months.

In some embodiments, the stability achieved by the composition may be such that the level of Impurity B (betamethasone sodium phosphate) remains not more than 0.3%, preferably below 0.2%, more preferably below 0.1% after storage at 25 degree Celsius and 60% RH for 24 months, or 29 months. In some embodiments, the stability achieved by the composition may be such that the level of Impurity B remains not more than 0.3%, preferably below 0.2%, more preferably below 0.07% after storage at 40 degree Celsius and 75% RH for 6 months.

In some embodiments, the stability achieved by the composition may be such that the level of Impurity C remains not more than 0.3%, preferably below 0.2%, more preferably below 0.11% after storage at 25 degree Celsius and 60% RH for 24 months, or 29 months. In some embodiments, the stability achieved by the composition may be such that the level of Impurity C remains not more than 0.3%, preferably below 0.26%, more preferably below 0.25% after storage at 40 degree Celsius and 75% RH for 6 months.

In some embodiments, the stability achieved by the composition may be such that the level of Impurity D remains not more than 0.2%, preferably below 0.1%, more preferably below 0.05% after storage at 25 degree Celsius and 60% RH for 24 months, or 29 months. In some embodiments, the stability achieved by the composition may be such that the level of Impurity D remains below 0.3%, preferably below 0.2%, more preferably below 0.18% after storage at 40 degree Celsius and 75% RH for 6 months.

In some embodiments, the stability achieved by the composition may be such that the level of Impurity F remains below 0.3%, preferably below 0.11%, more preferably below 0.05% after storage at 25 degree Celsius and 60% RH for 24 months, or 29 months. In some embodiments, the stability achieved by the composition may be such that the level of Impurity F remains below 0.3%, preferably below 0.11%, more preferably below 0.05% after storage at 40 degree Celsius and 75% RH for 6 months.

In some embodiments, the stability achieved by the composition may be such that the level of Impurity G remains below 0.3%, preferably below 0.11%, more preferably below 0.05% after storage at 25 degree Celsius and 60% RH for 24 months, or 29 months. In some embodiments, the stability achieved by the composition may be such that the level of Impurity G remains below 0.3%, preferably below 0.11%, more preferably below 0.05% after storage at 40 degree Celsius and 75% RH for 6 months.

In some embodiments, the stability achieved by the composition may be such that the level of the Sulphite Adduct remains below 0.21%, preferably below 0.1%, more preferably below 0.05% after storage at 25 degree Celsius and 60% RH for 24 months, or 29 months. In some embodiments, the stability achieved by the composition may be such that the level of Sulphite Adduct remains below 0.21%, preferably below 0.1%, more preferably below 0.05% after storage at 40 degree Celsius and 75% RH for 6 months.

In some embodiments, the stability achieved by the composition may be such that the level of the Unspecified Impurity remains below 0.21%, preferably below 0.17%, more preferably below 0.14% after storage at 25 degree Celsius and 60% RH for 24 months, or 29 months. In some embodiments, the stability achieved by the composition may be such that the level of the Unspecified Impurity remains below 0.21%, preferably below 0.16%, more preferably below 0.11% after storage at 40 degree Celsius and 75% RH for 6 months.

In some embodiments, the stability achieved by the composition may be such that the level of the Total Impurities remains below 2.9%, preferably below 1%, more preferably below 0.6% after storage at 25 degree Celsius and 60% RH for 24 months, or 29 months. In some embodiments, the stability achieved by the composition may be such that the level of the Total Impurities remains below 2.9%, preferably below 2%, more preferably below 1.7% after storage at 40 degree Celsius and 75% RH for 6 months.

In some embodiments, the stability achieved by the composition may be such that the level of the pH remains within a range of 7.4-7.8, preferably within a range of 7.5-7.7 after storage at 25 degree Celsius and 60% RH for 24 months, or 29 months. In some embodiments, the stability achieved by the composition may be such that the level of the pH remains within a range of 7.4-7.8, preferably within a range of 7.5-7.7 after storage at 40 degree Celsius and 75% RH for 6 months.

In some embodiments, where sodium sulfite is the antioxidant preservative, the concentration is between 0-70 ppm Sodium Sulfite (Anhydrous). In a specific embodiment of the invention, the formulation referred to as Formulation 10 (F10) containing 0 mg/ml Sodium Sulfite Anhydrous, 5.1% headspace Oxygen, and about 6 to 9 ml headspace volume showed an stable assay profile (for 29 months with a projection out to 48 months) in terms of Dexamethasone Phosphate equivalent content between about 906 and 1306 mg, and an acceptable impurity profile even in the absence of any sodium sulfite.

The present disclosure is directed to glucocorticoid containing pharmaceutical compositions having reduced levels of antioxidants. The ability to reduce the levels of antioxidants, which leads to a reduction in the toxic side effects associated with the use of such antioxidants, is a result of decreasing the headspace volume to total API ratio beyond what is typically used in the industry (Table 1). Accordingly, in a specific aspect of the invention, the ratio of headspace volume [ml] to total API (Dexamethasone Phosphate equivalent) [mg] ratio is between 0 to about 0.00588. In a preferred embodiment, the "(Sulfite:API)×headspace volume"—value is between 0 to about 0.05. In the most preferred embodiment, the "(Sulfite:API)×headspace volume"—value is between 0 to about 0.02.

At an accelerated storage condition of 40° C. (75% relative humidity-RH) elimination of Disodium Edetate at two different headspace oxygen levels (0%, 5%), with headspace volume between about 6-9 ml still maintains stability out to about 12 months (measured for 6 months with a projection out to 12 months) with the reduced headspace volume to API ratio of between about 0.0046 to about 0.0099. The latter constitutes a formulation made solely of GRAS excipients. Elimination of both Sodium Sulfite (Anhydrous) and Disodium Edetate is also possible with maintained stability out to 3 months with a headspace volume to API ratio of between about 0.0046 to about 0.0099 at an accelerated storage condition (40° C./75% RH). The result of F10 (at 25° C./60% RH) demonstrates that a shelf-life of at least 29 months or longer can be achieved without any antioxidants present. Moreover, at ICH-defined accelerated storage condition of 40° C./75% RH (tested up to 6 months), while lacking Disodium Edetate, increasing concentrations of Dexamethasone Sodium Phosphate (10-40 mg/ml or 10-200 mg/ml) lead to a decrease in total impurities. The ability to employ reduced levels of antioxidants, as disclosed in detail herein, results from a decrease in the headspace volume to API ratio when the compositions are distributed into packaging receptacles as well as due to the finding that Dexamethasone Sodium Phosphate becomes increasingly self-protective (against degradation) in higher concentration in a solution.

The present disclosure is also directed to use of the pharmaceutical compositions disclosed herein for treatment of patients in need of glucocorticoid drugs. Such treatment includes administration of the compositions to patients in need of anti-inflammatory, immunosuppression, lymphoablation, germinal center elimination, IL-2, IL-7, IL-12 and/or IL-15 elevation, mesenchymal stem cell elevation, G-CSF increase, neutrophil increase, tumor/cancer killing or lymphodepletion (preconditioning) before cell-based therapy, for example.

Accordingly, the present invention also provides the aqueous pharmaceutical formulations as disclosed herein for use in a method of treatment.

The present invention also provides the use of the aqueous pharmaceutical formulations as disclosed herein for the preparation of a medicament for use in a method of treatment.

The present invention also provides a method of treatment comprising administering to a subject in need thereof, a therapeutically effective amount of the aqueous pharmaceutical formulations as disclosed herein.

In some embodiments, the method is a method of reducing stem cell accumulation in the spleen in a subject, the method comprising administering the formulation to the subject prior to stem cell treatment. Such methods are disclosed, for example, in WO 2012/024519. In some embodiments, the method is a method of enhancing adoptive cellular therapy (ACT) in a subject, the method comprising administering the formulation to the subject prior to adoptive cellular therapy. Such methods are disclosed, for example, in WO 2018/183927. In some embodiments the method is a method of treatment of a lymphocyte mediated disease in a subject, the method comprising administering the formulation to the subject. Such methods are disclosed, for example, in PCT/US2019/054395.

As used herein, "patient in need thereof" and "subject in need thereof" may include individuals, e.g., mammals such as humans, canines, felines, porcines, etc., that have been diagnosed with inflammatory, immunosuppressive or cancer disorders. "Treating", "treatment" or "treat" can refer to the following: alleviating or delaying the appearance of clinical symptoms of a disease or condition in a patient that may be afflicted with or predisposed to the disease or condition, but does not yet experience or display clinical or subclinical symptoms of the disease or condition.

In certain embodiments, "treating", "treat" or "treatment" may refer to preventing the appearance of clinical symptoms of a disease or condition in a patient that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a patient to be treated may be statistically significant, mathematically significant, or at least perceptible to the patient and/or the physician. Nonetheless, prophylactic (preventive) treatment and therapeutic (curative) treatment are two separate embodiments of the disclosure herein.

Other uses of the compositions include use of a stem cell preparation and a therapeutic agent that inhibits binding of the stem cells to germinal centers within lymphoid tissue, in the manufacture of a medicament for regenerating a damaged tissue or organ in a subject who does not require hematological recovery due to cancer therapy, non-myeloablative therapy or myeloablative therapy, including chemotherapy, radiation, and combination treatments, wherein the therapeutic agent does not block the binding of the stem cells to damaged organ or tissue, thereby augmenting the numbers of circulating stem cells that can be attracted to target tissue or organ to regenerate the damaged organ or tissue.

Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically.

The term 'site of injection' as used herein non-exclusively relates to intra-tumor, or intra-organ such as the kidney or liver or pancreas or heart or lung or brain or spleen or eye, intra-muscular, intro-ocular, intra-striatal, intradermal, by dermal patch, by skin patch, by patch, into the cerebrospinal fluid, into the brain, among others.

The present disclosure is also related to methods for production of high concentration glucocorticoid containing pharmaceutical compositions comprising reduced levels of antioxidant preservatives. Such methods comprise the step of mixing the components of the composition and packaging said composition in an environment wherein the headspace volume to API ratio is decreased.

In a specific aspect of the invention, the headspace volume to API ratio is 0-0.00588. In such instances, the utilization of such a ratio during packaging permits one to use decreased concentrations of preservatives, such as for example, decreased levels of sulfites. In one aspect, the concentration of a sulfite is 0-70 ppm. For packaging, the headspace volume can be measured by calculation (vial brim volume-stopper volume-fluid fill volume) or by adding a liquid and measuring the volume when all gas has been replaced.

Also disclosed is a method for stabilising an aqueous pharmaceutical formulation comprising a glucocorticoid, the method comprising packaging an aqueous pharmaceutical formulation as disclosed herein into a container with a headspace volume (ml) to total glucocorticoid content (mg) ratio of 0.007 or less. In some preferred embodiments, the headspace volume (ml) to total glucocorticoid content (mg) ratio is 0.00588 or less.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Definitions

As used herein, "maintaining the assay" means maintaining quantitative chemical attributes of a formulation within acceptable limits as compared to values at the time of manufacture. This can be deteremined, for example, by assaying quantitative chemical attributes of a formulation and comparing these with the same attributes measured at the time of manufacture. In specific cases this refers to assaying levels/amounts of the active pharmaceutical ingredient (API) in the formulation and comparing this to the level/amount at the time of manufacture. In other cases this may also refer to assaying levels/amounts of degradation products of the active pharmaceutical ingredient (API), or the levels/amounts of unknown impurities in the formulation. In other cases this may also refer to assaying levels/amounts of total impurities in the formulation.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; Band C; A (alone); B (alone); and C (alone).

The use of the alternative (e.g., "or") should be understood to mean either one, both, or any combination thereof of the alternatives. As used herein, the indefinite articles "a" or "an" should be understood to refer to "one or more" of any recited or enumerated component.

As described herein, any concentration range, percentage range, ratio range or integer range is to be understood to include the value of any integer within the recited range and, when appropriate, fractions thereof (such as one-tenth and one-hundredth of an integer), unless otherwise indicated.

The term "about" when referring to a measurable value such as an amount or a temporal duration and the like refers to variations of +/−20% or +/−10% or +/−5%. That is, the term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 20% (i.e., ±20%). For example, about 3 mg can include any number between 2.3 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition such as one-tenth.

In the present disclosure concentrations may be expressed as e.g. grams per litre (g/l) or milligrams per milliliter (mg/ml). Concentrations may also be expressed as parts per million (ppm). One gram in 1000 ml (1 g/l) is equivalent to 1000 ppm. Thus, one milligram in 1000 ml (1 mg/1) is one ppm, and one milligram in 1 ml (1 mg/ml) is 1000 ppm. Similarly, 0.1 mg/ml is 100 ppm, 0.07 mg/ml is 70 ppm, and 0.01 mg/ml is 10 ppm. Those skilled in the art can readily convert between concentrations expressed in mg/ml and ppm.

The following examples are presented to further illustrate selected embodiments of the present invention.

EXAMPLES

Example Method

Assay and Related Substances (UPLC) for Dexamethasone Phosphate Injection. Details of a UPLC method for the determination of dexamethasone phosphate and related substances in a pharmaceutical formulation.

| Method Requirement | Description |
|---|---|
| Technique | Ultra Performance Liquid Chromatography (UPLC) |
| Reagents | WFI (Water for Injection) |
| | Ammonium Acetate, ACS reagent grade or equivalent |
| | Acetic Acid, ACS reagent |
| | Methanol, HPLC Grade or equivalent |
| UPLC System | Column: C8 |
| | Detector: UV |
| | Total Run Time: 10 minutes |
| | Elution Method: Gradient elution |
| Mobile phase | Mobile Phase A (Example Preparation) |
| | Dissolve 3.5 g of ammonium acetate in 1000 mL of WFI. |
| | Adjust the pH of the ammonium acetate buffer to 3.8 with glacial acetic acid. |
| | Mobile Phase B |
| | 100% Methanol |
| Diluent | Example Preparation |
| | Methanol and Mobile phase A, mixed thoroughly. |
| Standard | 1 mg/ml in Dexamethasone Phosphate in diluent |
| Sample preparation for assay and related substances | 1 mg/ml in Dexamethasone Phosphate in diluent |

Example 1

Table 1 shows a comparison of selected Dexamethasone Sodium Phosphate solutions (vials or ampouls) in the market to AVM0703 in terms of estimated/measured headspace volume, API concentration and content, sulfite concentration and content as well as chosen, calculated ratios: AVM0703 is below the values typically found in manufactured Dexamethasone Sodium Phosphate formulations in the industry concerning headspace volume [ml] to total API (Dexamethasone Phosphate equivalent) [mg] ratio, total Sulfite [mg] to total API (Dexamethasone Phosphate equivalent) [mg] ratio as well as one of the lowest regarding the "(Sulfite/API)×Headspace Volume" value.

TABLE 1

| Company name | Product name | NDC (or foreign drug code) | Estimated headspace (ml) | API conc. (as DP in mg/ml) | Vial (or Ampoule) volume (ml) | Total API (as DP in mg) | Sulfite conc. (mg/ml) | Total sulfite (mg) | Real headspace (liquid injected, vol. measured) (ml) |
|---|---|---|---|---|---|---|---|---|---|
| AVM Biotechnology | AVM0703 | | 8.00 | 24 | 51 | 1224 | 0.035 | 1.785 | 7.2 |
| Hameln pharmaceuticals | Dexamethasone | 01502/0079 | 0.75 | 10 | 10 | 100 | | | |
| Merck | Decadron, withdrawn | 0006-7646-03 | 0.90 | 24 | 5 | 120 | 1 | 5 | |
| Hospira | DBL ™ (Dexamethasone Sodium Phosphate) | n/a | 0.90 | 24 | 5 | 120 | | | |
| Fuji Pharma (Japan) | Solcort | 22000AMX00346000 | 0.90 | 24 | 5 | 120 | | | |
| Physicians Total Care, Inc. | Dexamethasone Sodium Phosphate | 54868-6099-0 | 1.92 | 10 | 10 | 100 | 1 | 10 | |
| West-Ward Pharmaceuticals Corp. | Dexamethasone Sodium Phosphate | 0641-0367-25 | 0.20 | 10 | 1 | 10 | 1.5 | 1.5 | |
| Mylan | Dexamethasone Sodium Phosphate | 67457-420-00 | 1.92 | 10 | 10 | 100 | | | 2 |
| Fresenius (pres. free) | Dexamethasone Sodium Phosphate | 63323-506-01 | 0.20 | 10 | 1 | 10 | | | |
| West-Ward Pharmaceuticals Corp. | Dexamethasone Sodium Phosphate | 0641-6146-01 | 0.75 | 4 | 5 | 20 | 1 | 5 | |
| Fresenius (preserved) | Dexamethasone Sodium Phosphate | 63323-516-10 | 3.64 | 10 | 10 | 100 | | | 4.04 |
| Henry Schein Animal Health | Dexaject SP* | 11695-40131 | 18.00 | 3.66 | 100 | 366 | 2 | 200 | |
| Hospira | Dexamethasone | 04515/0019 | 0.40 | 4 | 2 | 8 | 0.07 | 0.14 | |

| Company name | Product name | Headspace volume (ml) to total API (as DP in mg) ratio | Sulfite (mg) to total API (as DP in mg) ratio | Sulfite:API:Headspace ratio | (Sulfite:API) × Headspace value |
|---|---|---|---|---|---|
| AVM Biotechnology | AVM0703 | 0.00588 | 0.00146 | 0.000203 | 0.01050 |
| Hameln pharmaceuticals | Dexamethasone | 0.00750 | | | |
| Merck | Decadron, withdrawn | 0.00750 | 0.04167 | 0.046296 | 0.03750 |
| Hospira | DBL ™ (Dexamethasone Sodium Phosphate) | 0.00750 | | | |
| Fuji Pharma (Japan) | Solcort | 0.00750 | | | |
| Physicians Total Care, Inc. | Dexamethasone Sodium Phosphate | 0.01920 | 0.10000 | 0.052083 | 0.19200 |
| West-Ward Pharmaceuticals Corp. | Dexamethasone Sodium Phosphate | 0.02000 | 0.15000 | 0.750000 | 0.03000 |
| Mylan | Dexamethasone Sodium Phosphate | 0.0200 | | | |
| Fresenius (pres. free) | Dexamethasone Sodium Phosphate | 0.0200 | | | |
| West-Ward Pharmaceuticals Corp. | Dexamethasone Sodium Phosphate | 0.03750 | 0.25000 | 0.333333 | 0.18750 |
| Fresenius (preserved) | Dexamethasone Sodium Phosphate | 0.04040 | | | |
| Henry Schein Animal Health | Dexaject SP* | 0.04918 | 0.54645 | 0.030358 | 9.83607 |
| Hospira | Dexamethasone | 0.05000 | 0.01750 | 0.043750 | 0.00700 |

*all products for human use except Dexaject SP (horse)

Example 2

Composition of the Target Point Formulation of the DoE experiment in mg/ml.

TABLE 2

| AVM0703 Target Point Formulation, Design of Experiment | | |
|---|---|---|
| Component | Amount/value | |
| Dexamethasone Phosphate | 24 mg | Equivalent to Dexamethasone Sodium Phosphate: 26.23 mg; Equivalent to Dexamethasone: 19.94 mg |
| Sodium Citrate | 10 mg | GRAS excipient |
| Disodium EDTA | 0.5 mg | |
| Sodium Sulfite Anhydrous | 0.035 mg | GRAS excipient |
| Water for injection | q.s. to 1.00 ml | |
| pH (NaOH/HCl 0.1/1N) | 7.6 | |
| Oxygen headspace | 5% | |

Composition of the Target Point (center point) Formulation of the DoE experiment in weight percent (concentration).

TABLE 3

| Component | Concentration (%) | Type |
|---|---|---|
| Dexamethasone Sodium Phosphate | 2.53 | Active |
| Sodium Citrate | 0.96 | Buffer |
| Disodium Edetate | 0.048 | Chelator |
| Sodium Sulfite (Anhydrous) | 0.0034 | Antioxidant |
| Water for injection | 96.45 | Solvent |

Design of Experiment study formulations: 10 of the 16 formulations were monitored for long-term storage (25° C./60% RH). As part of the Design of Experiment study that was monitored for 29 months at 25° C./60% RH, 16 formulations were prepared. Table 4 shows specifications/composition of 10 out of the 16 formulations. Formulation 14 experienced atmospheric exposure by accident and was not used for the study. All formulations were described as clear, yellowish solutions. All formulations contained 26.23 mg/ml DSP, which is equivalent to 24 mg/ml dexamethasone phosphate (DP) as well as 0.05 mg/ml Disodium EDTA and 10 mg/ml Sodium Citrate. All formulations were packaged using the AVM0703 headspace volume (ml) to dexamethasone content (mg) ratio outlined in Table 1 (24 mg/ml dexamethasone phosphate; 51 ml vial; 7.2 ml headspace volume; headspace volume (ml) to dexamethasone content (mg) ratio of about 0.00588).

TABLE 4

| Formulation No. | DSP (mg/ml) | Sodium Citrate (mg/ml) | Disodium Edetate (mg/ml) | Sodium Sulfite (mg/ml) | Headspace Oxygen (%), set point | Headspace Oxygen (%), actual |
|---|---|---|---|---|---|---|
| 2 | 26.23 | 10 | 0.5 | 0.035 | 5.00 | 5.4 |
| 4 | | | | 0.035 | 5.00 | 5.4 |
| 6 | | | | 0.035 | 5.00 | 5.2 |
| 8 | | | | 0.035 | 5.00 | 5.1 |
| 9 | | | | 0.070 | 5.00 | 5.1 |
| 10 | | | | 0.000 | 5.00 | 5.1 |
| 11 | | | | 0.035 | 10.00 | 10.4 |
| 12 | | | | 0.035 | 5.00 | 5.1 |
| 15 | | | | 0.035 | 20.90 | n/a |
| 16 | | | | 0.070 | 20.90 | n/a |

AVM0703—Design of Experiment—six formulations were monitored for over 18 months (25° C./60% RH). Six formulations with varying levels of Sodium Sulfite (Anhydrous) and Headspace Oxygen which were tested for stability at 18 months. Aside from F15 (atmospheric Oxygen level of 20.9%), all 5 other formulations (F2, 4, 9, 10 and 11) were within the required API assay or impurity thresholds. Those six were selected from 15 formulations that were manufactured for the DoE study to assess those 2 factors: 13 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml, respectively. Results are shown in Table 5.

TABLE 5

| 18 months stability | | | | | | |
|---|---|---|---|---|---|---|
| | Target point | | | No sulfite | | |
| Formulation # | 2 | 4 | 9 | 10 | 11 | 15 |
| Assay % (95.0-105.0%) | 98.5 | 98.4 | 98.3 | 98.6 | 98.1 | 97.9 |

TABLE 5-continued

| 18 months stability | | | | | | |
|---|---|---|---|---|---|---|
| | Target point | | | No sulfite | | |
| Formulation # | 2 | 4 | 9 | 10 | 11 | 15 |
| Impurity A (%) (NMT 0.5%) | 0.20 | 0.20 | 0.20 | 0.20 | 0.20 | 0.40 |
| Impurity B (%) (NMT 0.5%) | 0.10 | 0.10 | 0.10 | 0.10 | 0.10 | 0.10 |
| Impurity C (%) (NMT 0.5%) | 0.10 | 0.10 | 0.10 | 0.10 | 0.10 | 0.10 |
| Impurity D (%) (NMT 0.5%) | <0.05 | <0.05 | <0.05 | <0.05 | <0.05 | <0.05 |
| Impurity F (%) (NMT 0.5%) | <0.05 | <0.05 | <0.05 | <0.05 | <0.05 | <0.05 |
| Impurity G (%) (NMT 0.5%) | <0.05 | <0.05 | <0.05 | 0.10 | 0.10 | 0.10 |
| Sulphite adduct (NMT 0.2%) | *n/a | *n/a | *n/a | *n/a | *n/a | *n/a |
| Any unspecified impurity (%) (NMT 0.2%) | 0.17 | 0.16 | 0.17 | 0.15 | 0.17 | 0.37 |
| Total impurities (%) (NMT 3.0%) | 0.4 | 0.4 | 0.5 | 0.4 | 0.5 | 1.0 |
| pH (7.4-7.8) | 7.6 | 7.7 | 7.7 | 7.6 | 7.6 | 7.5 |
| Sodium Sulfite (mg/ml) | 0.035 | 0.035 | 0.070 | 0.000 | 0.035 | 0.035 |
| Headspace Oxygen (%), set point | 5.00 | 5.00 | 5.00 | 5.00 | 10.00 | 20.90 |
| Headspace Oxygen (%), actual | 5.4 | 5.4 | 5.1 | 5.1 | 10.4 | n/a |

NMT = not more than (threshold)

AVM0703—Design of Experiment—nine formulations were monitored for over 24 months (25° C./60% RH). Nine formulations with varying levels of Sodium Sulfite (Anhydrous) and Headspace Oxygen which were tested for stability at 24 months. Aside from F15 (atmospheric Oxygen level of 20.9%), all other 8 formulations (F2, 4, 6, 8, 9, 10, 11 and 12) were within the required API assay or impurity thresholds. Those nine were selected from 15 formulations that were manufactured for the DoE study to assess those 2 factors: 13 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml, respectively. Results are shown in Table 6.

TABLE 6

| 24 months stability | | | | | | | | | |
|---|---|---|---|---|---|---|---|---|---|
| | Target point (TP) | | | | | No sulfite | | TP | |
| Formulation # | 2 | 4 | 6 | 8 | 9 | 10 | 11 | 12 | 15 |
| Assay % (95.0-105.0%) | 97.4 | 97.2 | 96.7 | 96.8 | 95.7 | 96.9 | 96.7 | 98.1 | 96.7 |
| Impurity A (%) (NMT 0.5%) | 0.2 | 0.2 | 0.2 | 0.2 | 0.2 | 0.2 | 0.2 | 0.2 | 0.5 |
| Impurity B (%) (NMT 0.5%) | 0.1 | 0.1 | 0.1 | 0.1 | 0.1 | 0.1 | 0.1 | 0.1 | 0.1 |
| Impurity C (%) (NMT 0.5%) | 0.1 | 0.1 | 0.1 | 0.1 | 0.1 | 0.1 | 0.1 | 0.1 | 0.1 |
| Impurity D (%) (NMT 0.5%) | <0.05 | <0.05 | <0.05 | <0.05 | <0.05 | <0.05 | <0.05 | <0.05 | 0.1 |
| Impurity F (%) (NMT 0.5%) | <0.05 | 0.1 | 0.1 | <0.05 | <0.05 | <0.05 | <0.05 | <0.05 | <0.05 |
| Impurity G (%) (NMT 0.5%) | <0.05 | <0.05 | <0.05 | <0.05 | <0.05 | <0.05 | 0.10 | <0.05 | 0.10 |
| Sulphite adduct (NMT 0.2%) | *n/a | *n/a | *n/a | *n/a | *n/a | *n/a | *n/a | *n/a | *n/a |
| Any unspecified impurity (%) (NMT 0.2%) | 0.13 | 0.16 | 0.13 | 0.14 | 0.13 | 0.15 | 0.16 | 0.13 | 0.41 |
| Total impurities (%) (NMT 3.0%) | 0.5 | 0.5 | 0.5 | 0.5 | 0.5 | 0.5 | 0.6 | 0.5 | 1.2 |
| pH (7.4-7.8) | 7.7 | 7.7 | 7.7 | 7.6 | 7.7 | 7.7 | 7.6 | 7.6 | 7.5 |
| Sodium Sulfite (mg/ml) | 0.035 | 0.035 | 0.035 | 0.035 | 0.070 | 0.000 | 0.035 | 0.035 | 0.035 |

TABLE 6-continued

| 24 months stability | | | | | | | | | |
|---|---|---|---|---|---|---|---|---|---|
| | Target point (TP) | | | | | No sulfite | | TP | |
| Formulation # | 2 | 4 | 6 | 8 | 9 | 10 | 11 | 12 | 15 |
| Headspace Oxygen (%), set point | 5.00 | 5.00 | 5.00 | 5.00 | 5.00 | 5.00 | 10.00 | 5.00 | 20.90 |
| Headspace Oxygen (%), actual | 5.4 | 5.4 | 5.2 | 5.1 | 5.1 | 5.1 | 10.4 | 5.1 | n/a |

NMT = not more than (threshold)

AVM0703—Design of Experiment—nine formulations were monitored for over 29 months (25° C./60% RH). Nine formulations with varying levels of Sodium Sulfite (Anhydrous) and Headspace Oxygen which were tested for stability at 29 months. Aside from F15 (atmospheric Oxygen level of 20.9%), all other 8 formulations (F2, 4, 6, 8, 9, 10, 11 and 12) were within the required API assay or impurity thresholds. Those nine were selected from 15 formulations that were manufactured for the DoE study to assess those 2 factors: 13 formulations (F1-F13) to assess Sodium Sulfite (Anhydrous) in a range of 0 to 0.07 mg/mL and Headspace Oxygen in a range of 0 to 10%, while 2 additional formulations (F15, F16) were manufactured to assess stability at atmospheric Oxygen (20.9%) using 0.035 or 0.07 mg/ml Sodium Sulfite (Anhydrous), respectively. Results are shown in Table 7.

TABLE 7

| 29 months stability | | | | | | | | | |
|---|---|---|---|---|---|---|---|---|---|
| | Target point (TP) | | | | | No sulfite | | TP | |
| Formulation # | 2 | 4 | 6 | 8 | 9 | 10 | 11 | 12 | 15 |
| Assay % (95.0-105.0%) | 98.3 | 98.2 | 97.9 | 97.5 | 97.0 | 98.1 | 98.3 | 99.0 | 97.7 |
| Impurity A (%) (NMT 0.5%) | 0.3 | 0.2 | 0.3 | 0.3 | 0.2 | 0.3 | 0.3 | 0.3 | 0.6 |
| Impurity B (%) (NMT 0.5%) | 0.1 | 0.1 | 0.1 | 0.1 | 0.1 | 0.1 | 0.1 | 0.1 | 0.1 |
| Impurity C (%) (NMT 0.5%) | 0.1 | 0.1 | 0.1 | 0.1 | 0.1 | 0.1 | 0.1 | 0.1 | 0.1 |
| Impurity D (%) (NMT 0.5%) | 0.1 | 0.1 | 0.1 | 0.1 | 0.1 | 0.1 | 0.1 | 0.1 | 0.1 |
| Impurity F (%) (NMT 0.5%) | <0.05 | <0.05 | <0.05 | <0.05 | <0.05 | <0.05 | <0.05 | <0.05 | <0.05 |
| Impurity G (%) (NMT 0.5%) | <0.05 | <0.05 | <0.05 | <0.05 | <0.05 | 0.10 | <0.05 | <0.05 | 0.10 |
| Sulphite adduct (NMT 0.2%) | *n/a | *n/a | *n/a | *n/a | *n/a | *n/a | *n/a | *n/a | *n/a |
| Any unspecified impurity (%) (NMT 0.2%) | 0.20 | 0.20 | 0.19 | 0.20 | 0.19 | 0.19 | 0.19 | 0.20 | 0.48 |
| Total impurities (%) (NMT 3.0%) | 0.7 | 0.7 | 0.7 | 0.7 | 0.7 | 0.7 | 0.7 | 0.7 | 1.4 |
| pH (7.4-7.8) | 7.6 | 7.7 | 7.6 | 7.6 | 7.7 | 7.6 | 7.6 | 7.6 | 7.5 |
| Sodium Sulfite (mg/ml) | 0.035 | 0.035 | 0.035 | 0.035 | 0.070 | 0.000 | 0.035 | 0.035 | 0.035 |
| Headspace Oxygen (%), set point | 5.00 | 5.00 | 5.00 | 5.00 | 5.00 | 5.00 | 10.00 | 5.00 | 20.90 |
| Headspace Oxygen (%), actual | 5.4 | 5.4 | 5.2 | 5.1 | 5.1 | 5.1 | 10.4 | 5.1 | n/a |

NMT = not more than (threshold)

Design of experiment result for 29 months for the active pharmaceutical ingredient API in the AVM0703 formulation. (FIG. 1) Dexamethasone Sodium Phosphate (DSP). Six formulations with varying levels of Sodium Sulfite (Anhydrous) and Headspace Oxygen are tested for stability. Formulation 2 and 4 (F2, 4) are target point formulations with 0.035 mg/ml Sodium Sulfite (Anhydrous) and 5% Headspace Oxygen (95% nitrogen). The result demonstrates that the formulations are within a range of 95-105% DSP content for the tested values of Sodium Sulfite (Anhydrous) of 0 (F10), 0.035 (F2, 4, 11, 15) and 0.07 mg/ml (F9) at 5% (F2, 4, 9, 10), 10% (F11) and 20.90% (F15) headspace oxygen, not dropping below 95% for any formulation tested (25° C./60% RH).

Figure 2:
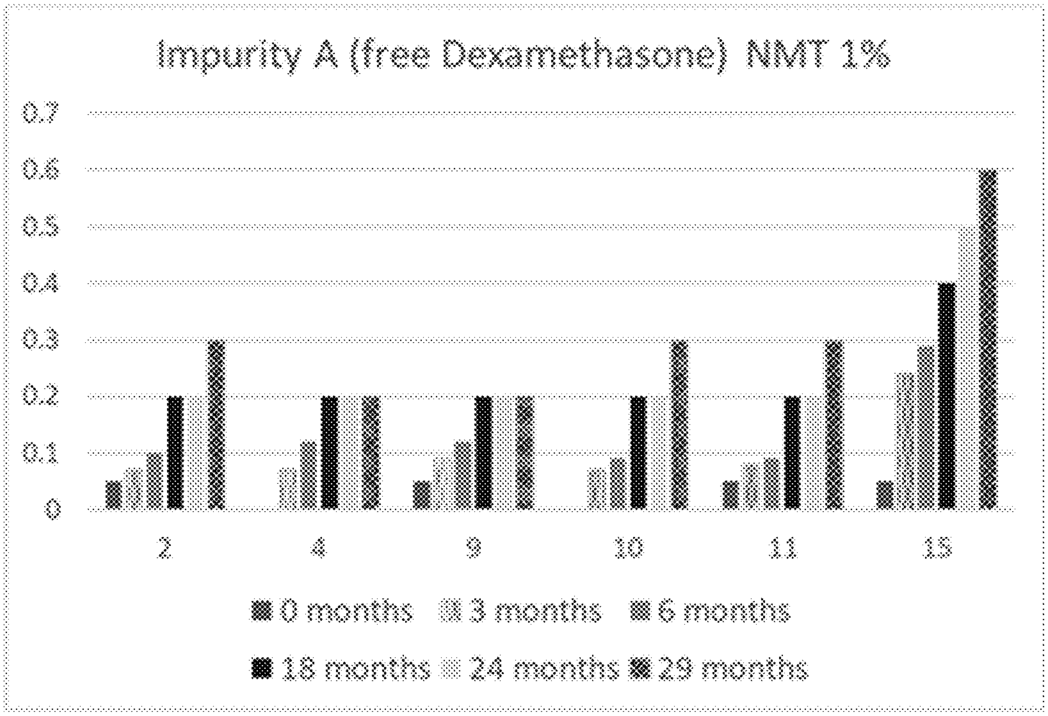
FIG. 2 demonstrates that all the tested formulations are within a range of initially NMT (not more than) 0.5% for free Dexamethasone (later change to 1%; Imp A) with the exception of formulation 15 (atmospheric headspace oxygen). Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace Oxygen. Free Dexamethasone accumulates due to acid hydrolysis from DSP (25° C./60% RH; 29 months).

Design of experiment result for 29 months for the "Impurity a" (free Dexamethasone) in the AVM0703 formulation. (FIG. 2) The result demonstrates that all the tested formulations are within a range of NMT (not more than) 1% (initially 0.5%, then increased to 1%) for free Dexamethasone (Imp A). Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace oxygen. Free Dexamethasone accumulates due to acid hydrolysis from DSP (25° C./60% RH).

Figure 3:
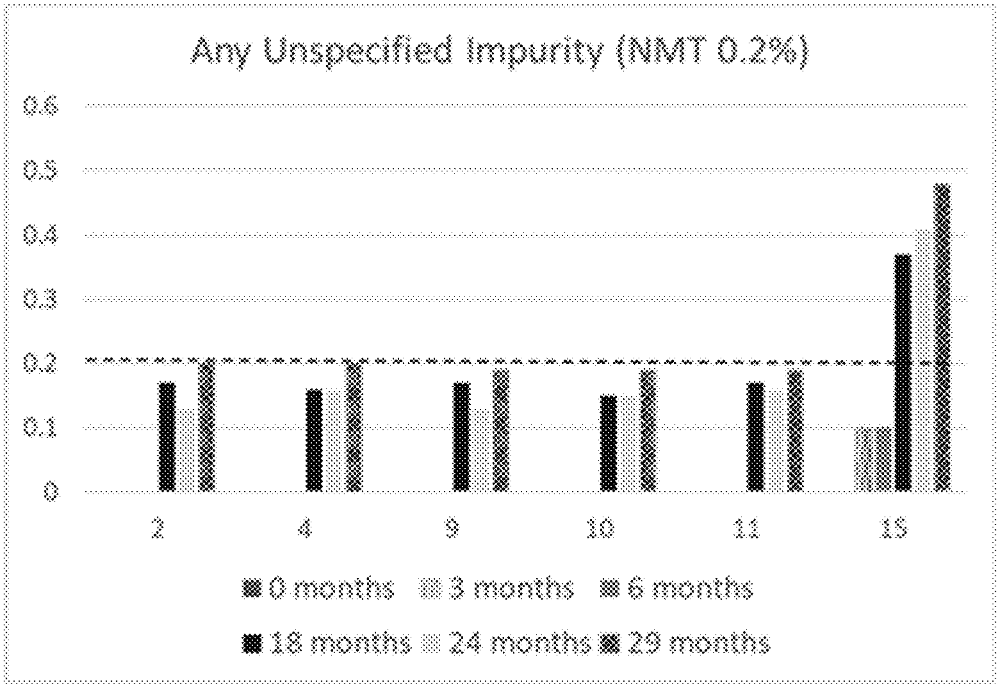
FIG. 3 demonstrates that all the tested formulations are within a range of NMT (not more than) 0.2% for not yet identified impurities. Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace Oxygen. Only formulation F15 (at atmospheric oxygen level) was above the threshold for the time point of 18 months and later (25° C./60% RH; 29 months).

Design of experiment result for 29 months for "any Unspecified Impurity" in the Avm0703 formulation. (FIG. 3) The result demonstrates that all the tested formulations are within a range of NMT (not more than) 0.2% for not yet identified impurities. Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace oxygen. Only formulation F15 (at atmospheric oxygen level) was above the threshold for the last time point (25° C./60% RH).

Figure 4:
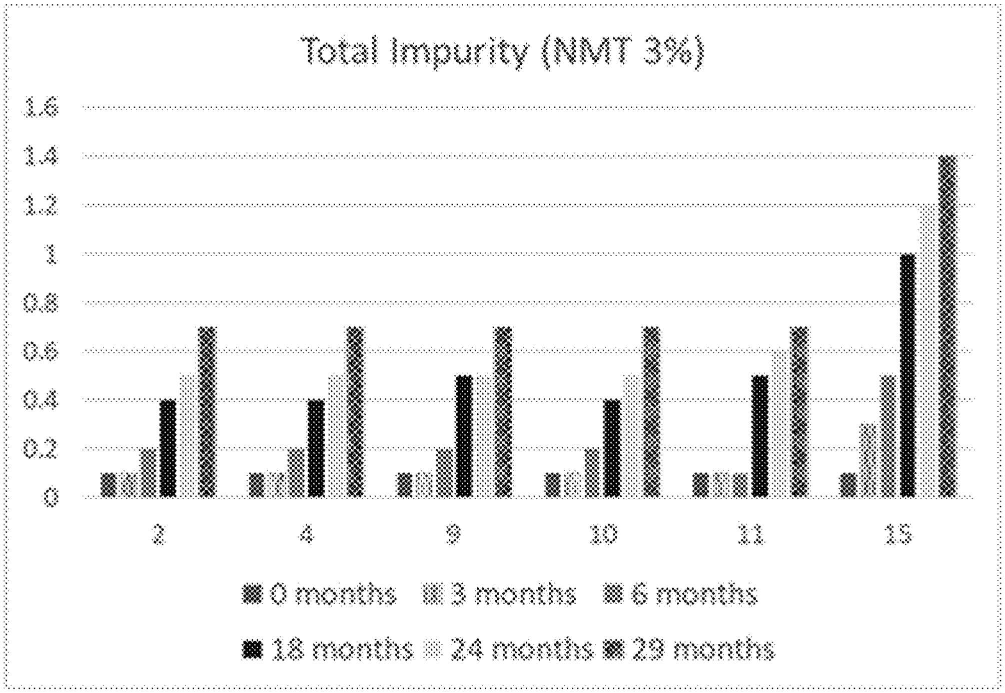
FIG. 4 demonstrates that all the tested formulations are within a range of NMT (not more than) 3% for Total Impurities (consistent with USP). Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace Oxygen (25° C./60% RH; 29 months).

Design of experiment result for 29 months for the "Total Impurity" in the AVM0703 formulation. (FIG. 4). The result demonstrates that all the tested formulations are within a range of NMT (not more than) 3%. Tested values of Sodium Sulfite (Anhydrous) were 0 (F10), 0.035 (F2, 4, 11, 15) and 0.07 mg/ml (F9) at 5% (F2, 4, 9, 10), 10% (F11) and 20.90% (F15) headspace oxygen (25° C./60% RH).

FIG. 5: Design of experiment target point formulations 2 and 4 (F2, F4): 0.035 mg/ml Sodium Sulfite Anhydrous, 5.4% headspace oxygen. The projection with 6 measured (up to 29 months) data points shows for both formulations that the Dexamethasone Sodium Phosphate content is expected to be above 95% for 48 months (25° C./60% RH).

Figure 6:
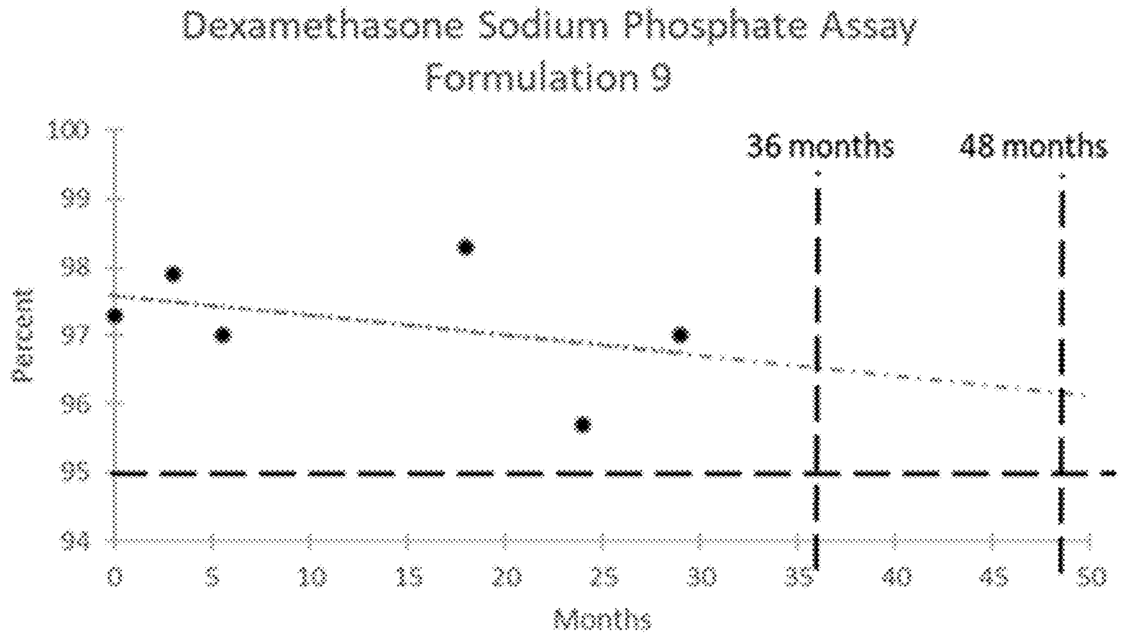
FIG. 6 demonstrates that formulation 9 (F9: 0.07 mg/ml Sodium Sulfite Anhydrous, 5.1% Oxygen headspace) is expected to have an assay above 95% for the Dexamethasone Sodium Phosphate content for 48 months (projection with 6 measured data points; up to 29 months, 25° C./60% RH).

FIG. 6: Design of Experiment formulation 9 (F9): 0.07 mg/ml Sodium Sulfite Anhydrous, 5.1% headspace oxygen. The projection with 6 measured (up to 29 months) data points shows for the formulation that the Dexamethasone Sodium Phosphate content is expected to be above 95% for 48 months (25° C./60% RH).

Figure 7:
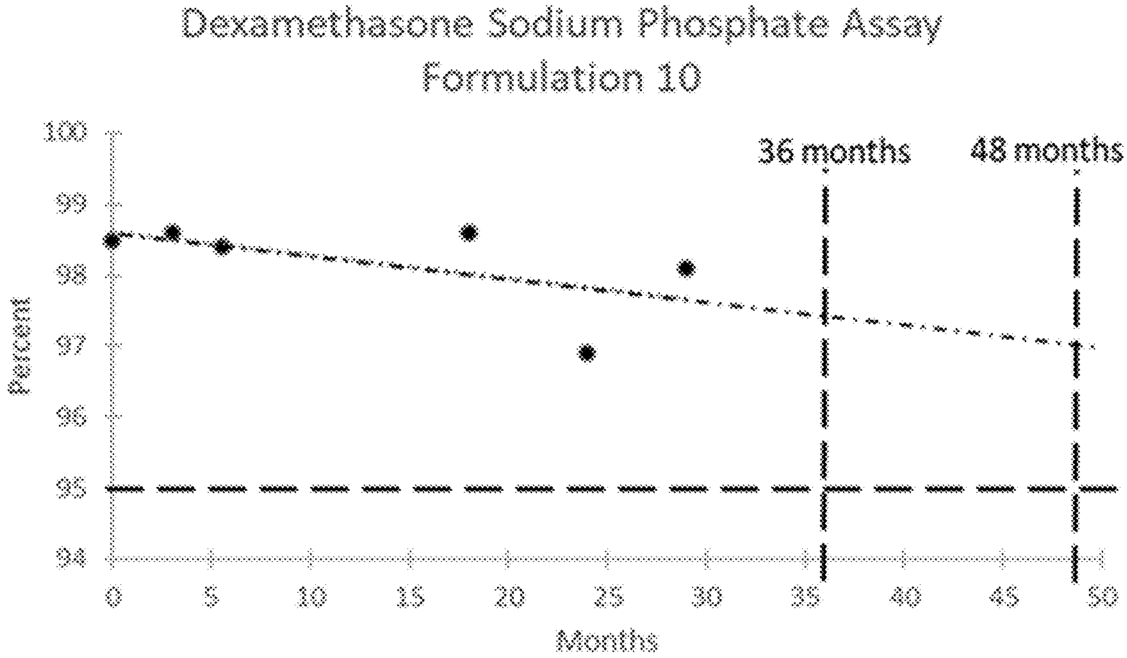
FIG. 7 demonstrates that formulation 10 (F10: 0 mg/ml Sodium Sulfite Anhydrous, 5.1% Oxygen headspace) is expected to have an assay above 95% for the Dexamethasone Sodium Phosphate content for 48 months (projection with 6 measured data points; up to 29 months, 25° C./60% RH).

FIG. 7: Design of Experiment formulation 10 (F10): 0 mg/ml Sodium Sulfite Anhydrous, 5.1% headspace oxygen. The projection with 6 measured data points (up to 29 months) shows for the formulation that the Dexamethasone Sodium Phosphate content is expected to be above 95% for 48 months (25° C./60% RH).

Figure 8:
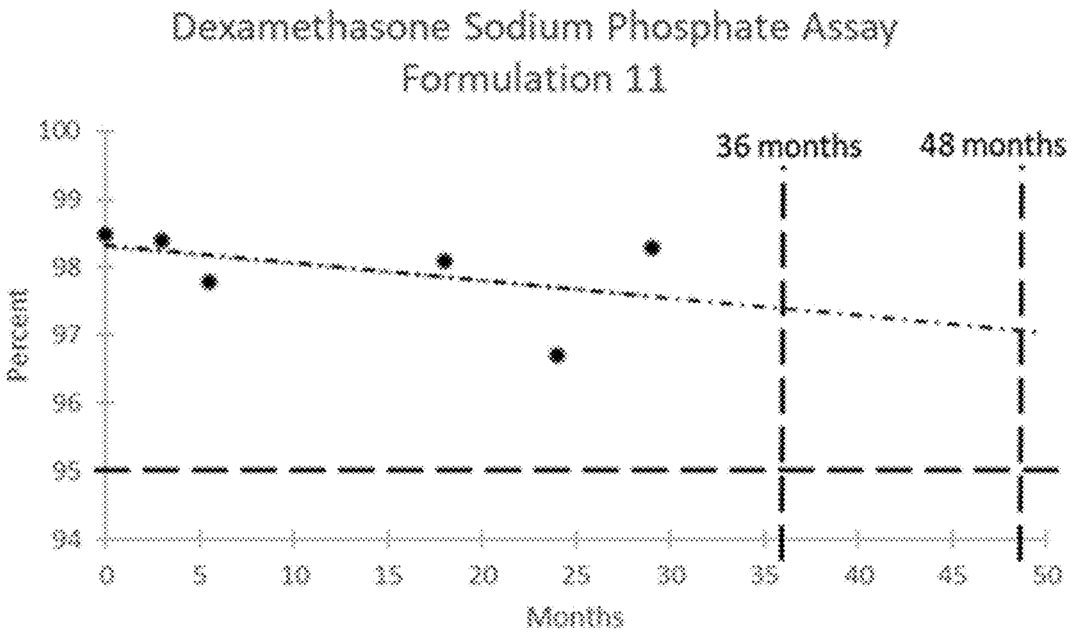
FIG. 8 demonstrates that formulation 11 (F11: 0.035 mg/ml Sodium Sulfite Anhydrous, 10.4% Oxygen headspace) is expected to have an assay above 95% for the Dexamethasone Sodium Phosphate content for 48 months (projection with 6 measured data points; up to 29 months, 25° C./60% RH).

FIG. 8: Design of Experiment formulation 11 (F11): 0.035 mg/ml Sodium Sulfite Anhydrous, 10.4% headspace oxygen. The projection with 6 measured data points (up to 29 months) shows for the formulation that the Dexamethasone Sodium Phosphate content is expected to be above 95% for 36 months (25° C./60% RH).

Figure 9:
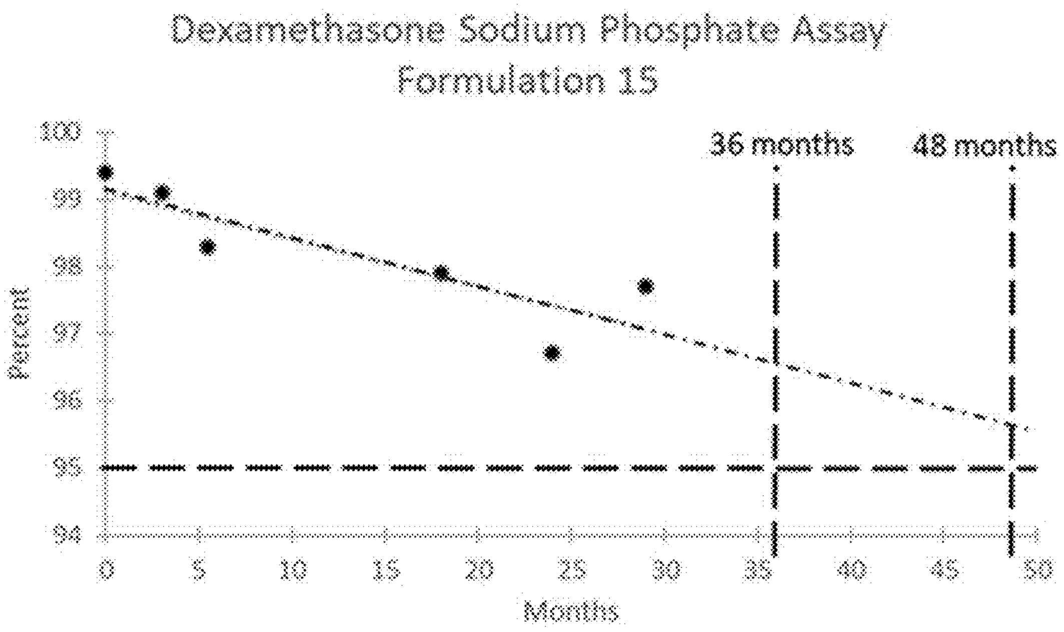
FIG. 9 demonstrates that formulation 15 (F15: 0.035 mg/ml Sodium Sulfite Anhydrous, 20.9% Oxygen headspace) is expected to have an assay above 95% for the Dexamethasone Sodium Phosphate content for 48 months (projection with 6 measured data points; up to 29 months, 25° C./60% RH).

FIG. 9: Design of Experiment formulation 15 (F15): 0.035 mg/ml Sodium Sulfite Anhydrous, 20.9% Headspace Oxygen. The projection with 6 measured data points (up to 29 months) shows for the formulation that the Dexamethasone Sodium Phosphate content is expected to be above 95% for 48 months (25° C./60% RH).

Figure 10:
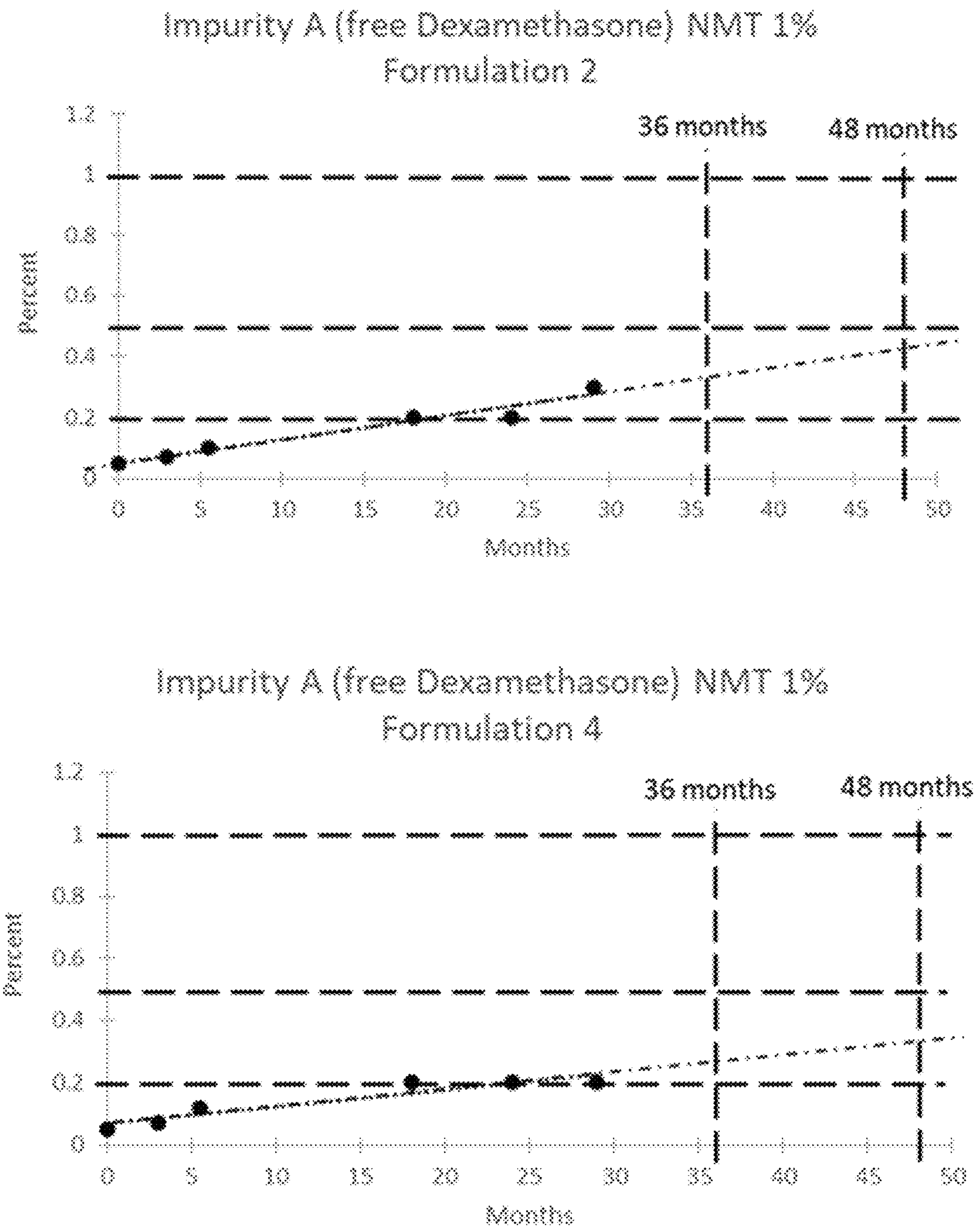
FIG. 10 demonstrates that formulations 2 and 4 (F2, F4: 0.035 mg/ml Sodium Sulfite Anhydrous, 5.4% Oxygen headspace) are expected to below 0.5% for Impurity A for 48 months (projection with 6 measured data points; up to 29 months, 25° C./60% RH).

FIG. 10: Design of Experiment target point formulations 2 and 4 (F2, F4): 0.035 mg/ml Sodium Sulfite Anhydrous, 5.4% headspace oxygen. The projection with 6 measured data points (up to 29 months) shows for both formulations that the Impurity A is expected to be below 0.5% for 48 months (25° C./60% RH).

Figure 11:
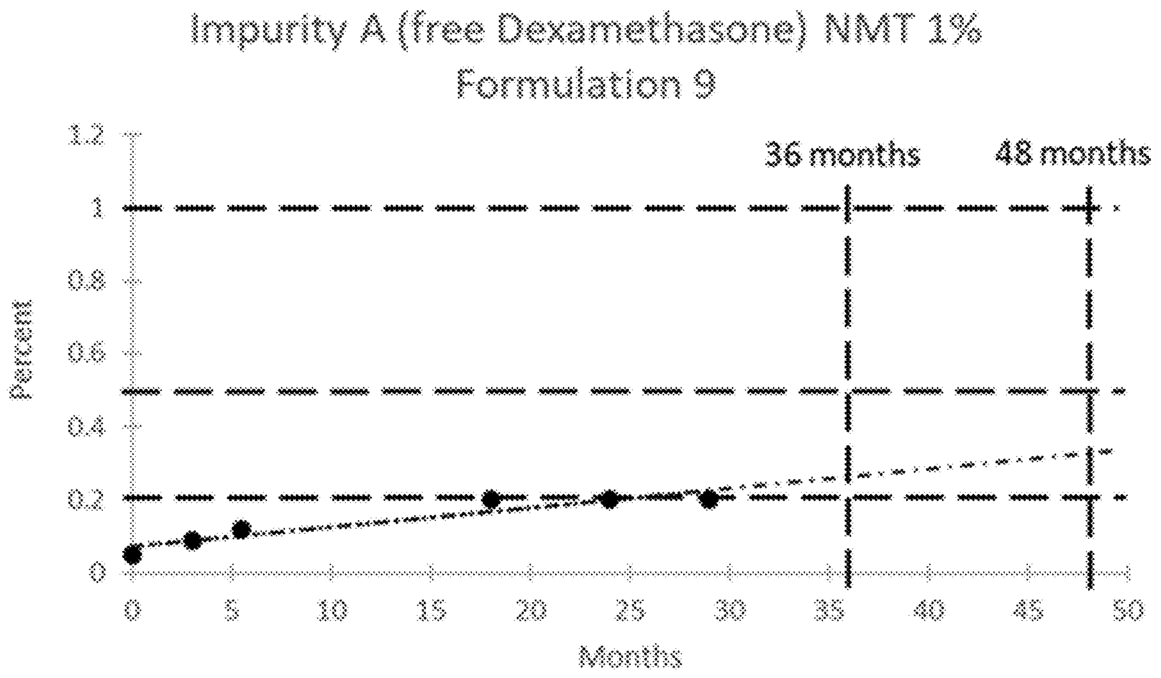
FIG. 11 demonstrates that formulation 9 (F9: 0.07 mg/ml Sodium Sulfite Anhydrous, 5.1% Oxygen headspace) is expected to be below 0.5% for Impurity A for 48 months (projection with 6 measured data points; up to 29 months, 25° C./60% RH).

FIG. 11: Design of Experiment formulation 9 (F9): 0.07 mg/ml Sodium Sulfite Anhydrous, 5.1% headspace oxygen. The projection with 6 measured data points (up to 29 months) shows for the formulation that the Impurity A is expected to be below 0.5% for 48 months (25° C./60% RH).

Figure 12:
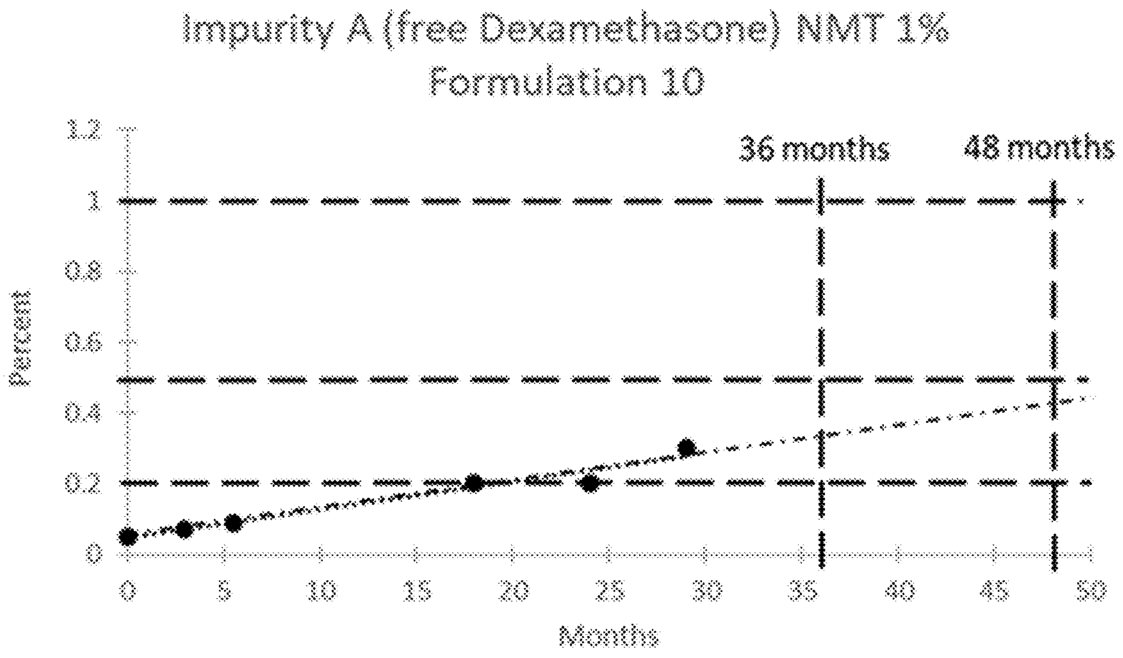
FIG. 12 demonstrates that formulation 10 (F10: 0 mg/ml Sodium Sulfite Anhydrous, 5.1% Oxygen headspace) is expected to be below 0.5% for Impurity A for 48 months (projection with 6 measured data points; up to 29 months, 25° C./60% RH).

FIG. 12: Design of Experiment formulation 10 (F10): 0 mg/ml Sodium Sulfite Anhydrous, 5.1% headspace oxygen. The projection with 6 measured data points (up to 29 months) shows for the formulation that the Impurity A is expected to be below 0.5% for 48 months (25° C./60% RH).

Figure 13:
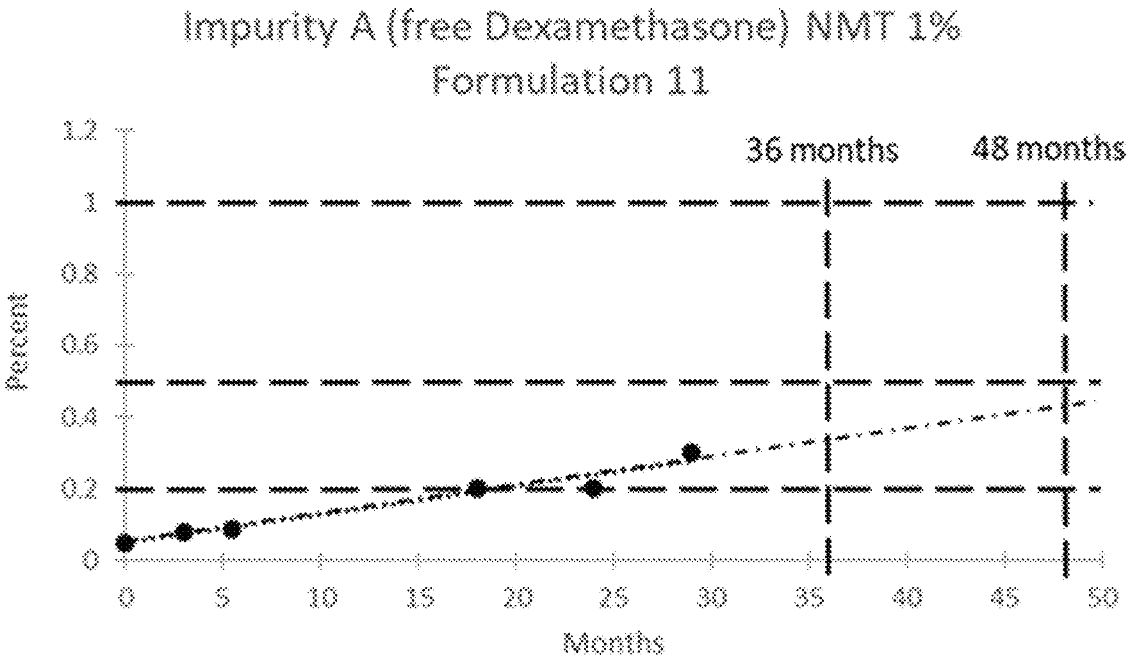
FIG. 13 demonstrates that formulation 11 (F11: 0.035 mg/ml Sodium Sulfite Anhydrous, 10.4% Oxygen headspace) is expected to be below 0.5% for Impurity A for 48 months (projection with 6 measured data points; up to 29 months, 25° C./60% RH).

FIG. 13: Design of Experiment formulation 11 (F11): 0.035 mg/ml Sodium Sulfite Anhydrous, 10.4% headspace oxygen. The projection with 6 measured data points (up to 29 months) shows for the formulation that the Impurity A is expected to be below 0.5% for 48 months (25° C./60% RH).

Figure 14:
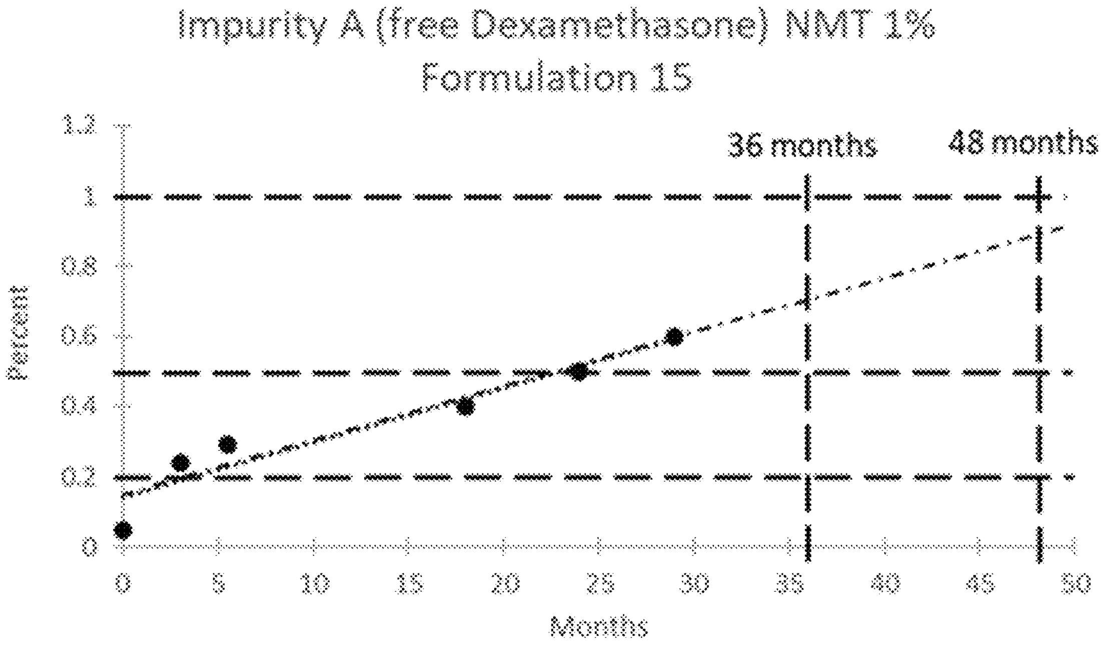
FIG. 14 demonstrates that formulation 15 (F15: 0.035 mg/ml Sodium Sulfite Anhydrous, 20.9% Oxygen headspace; atmospheric) crossed 0.5% for Impurity A at 24 months. The projection shows impurity A is expected to be below 1% for 48 months (projection with 6 measured data points; up to 29 months, 25° C./60% RH).

FIG. 14: Design of Experiment formulation 15 (F15): 0.035 mg/ml Sodium Sulfite Anhydrous, 20.9% headspace oxygen (atmospheric). The projection with 6 measured data points (up to 29 months) shows for the formulation that the Impurity A crossed 0.5% at 24 months, while the projection shows for this impurity to be expected less than 1% for 48 months (25° C./60% Rh).

Figure 15:
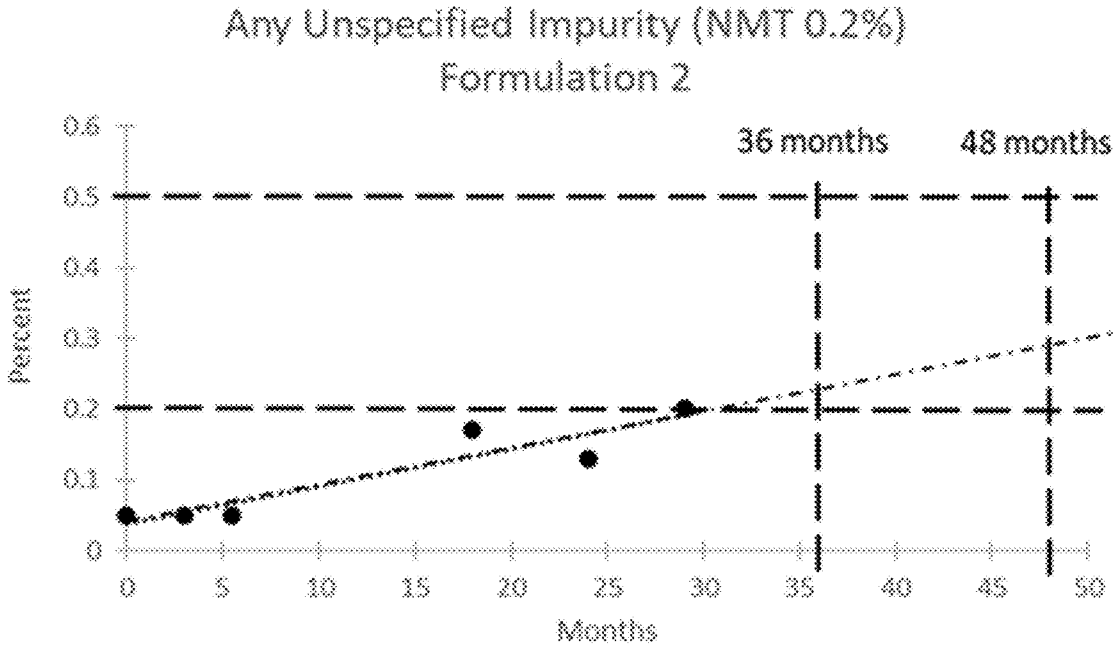
FIG. 15 demonstrates that formulation 2 (F2: 0.035 mg/ml Sodium Sulfite Anhydrous, 5.4% headspace oxygen) reached 0.2% for the Unspecified Impurity at 29 months, but is expected to be below 0.5% for 48 months (projection with 6 measured data points; up to 29 months, 25° C./60% RH).

FIG. 15: Design of Experiment formulation 2 (F2): 0.035 mg/ml Sodium Sulfite Anhydrous, 5.4% headspace oxygen. The projection with 6 measured data points (up to 29 months) shows for the formulation that the Unspecified Impurity reached 0.2% at 29 months, but is expected to be below 0.5% for 48 months (25° C./60% RH).

Figure 16:
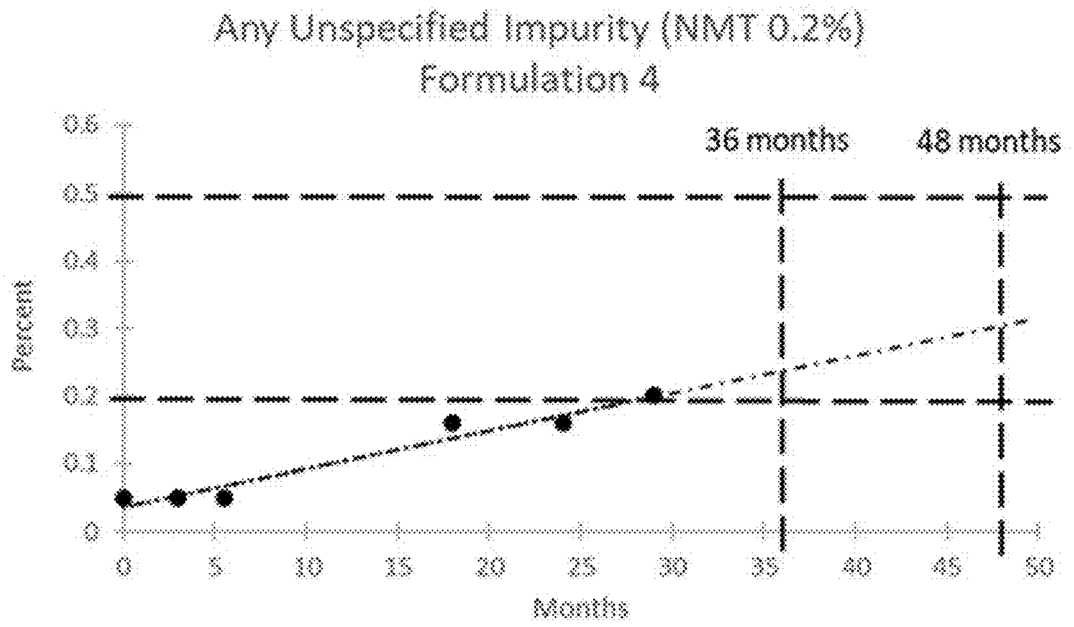
FIG. 16 demonstrates that formulation 4 (F4: 0.035 mg/ml Sodium Sulfite Anhydrous, 5.4% headspace oxygen) reached 0.2% at 29 months, but is expected to be below 0.5% for 48 months (projection with 6 measured data points; up to 29 months, 25° C./60% RH).

FIG. 16: Design of Experiment formulation 4 (F4): 0.035 mg/ml Sodium Sulfite Anhydrous, 5.4% headspace oxygen. The projection with 6 measured data points shows for the formulation that the Unspecified Impurity has reached 0.2% at 29 months, but is expected to be below 0.5% for 48 months (25° C./60% RH).

Figure 17:
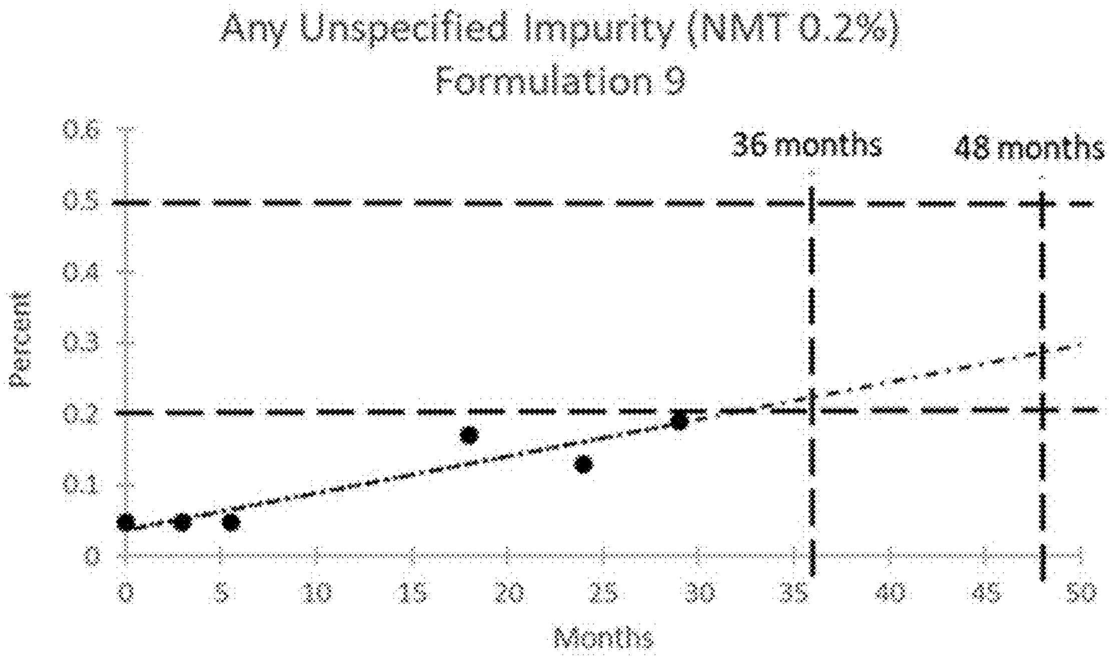
FIG. 17 demonstrates that formulation 9 (F9: 0.07 mg/ml Sodium Sulfite Anhydrous, 5.1% Oxygen headspace) is expected to cross 0.2% at about 32 months, but to be below 0.5% for 48 months (projection with 6 measured data points; up to 29 months, 25° C./60% RH).

FIG. 17: Design of Experiment formulation 9 (F9): 0.070 mg/ml Sodium Sulfite Anhydrous, 5.1% headspace oxygen. The projection with 6 measured data points shows for the formulation that the Unspecified Impurity is expected to cross 0.2% at about 32 months, but to be below 0.5% for 48 months (25° C./60% RH).

Figure 18:
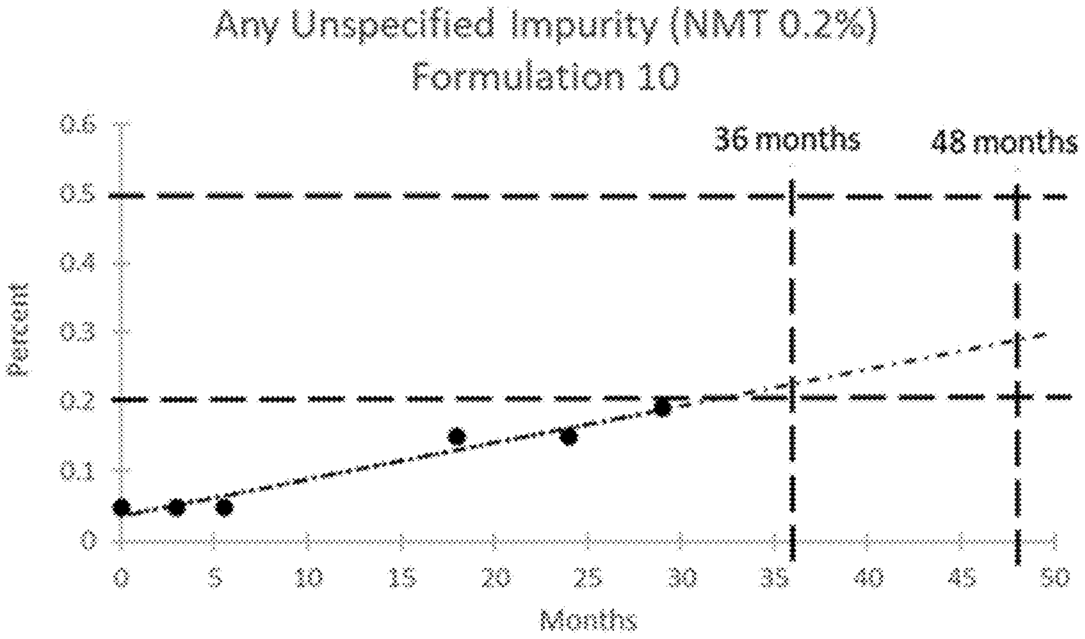
FIG. 18 demonstrates that formulation 10 (F10: 0 mg/ml Sodium Sulfite Anhydrous, 5.1% Oxygen headspace) is expected to cross 0.2% at about 32 months, but to be below 0.5% for 48 months (projection with 6 measured data points; up to 29 months, 25° C./60% RH).

FIG. 18: Design of Experiment Formulation 10 (F10): 0 mg/ml Sodium Sulfite Anhydrous, 5.1% headspace oxygen. The projection with 6 measured data points shows for the formulation that the Unspecified Impurity is expected to cross 0.2% at 32 months, but to be below 0.5% for 48 months (25° C./60% RH).

Figure 19:
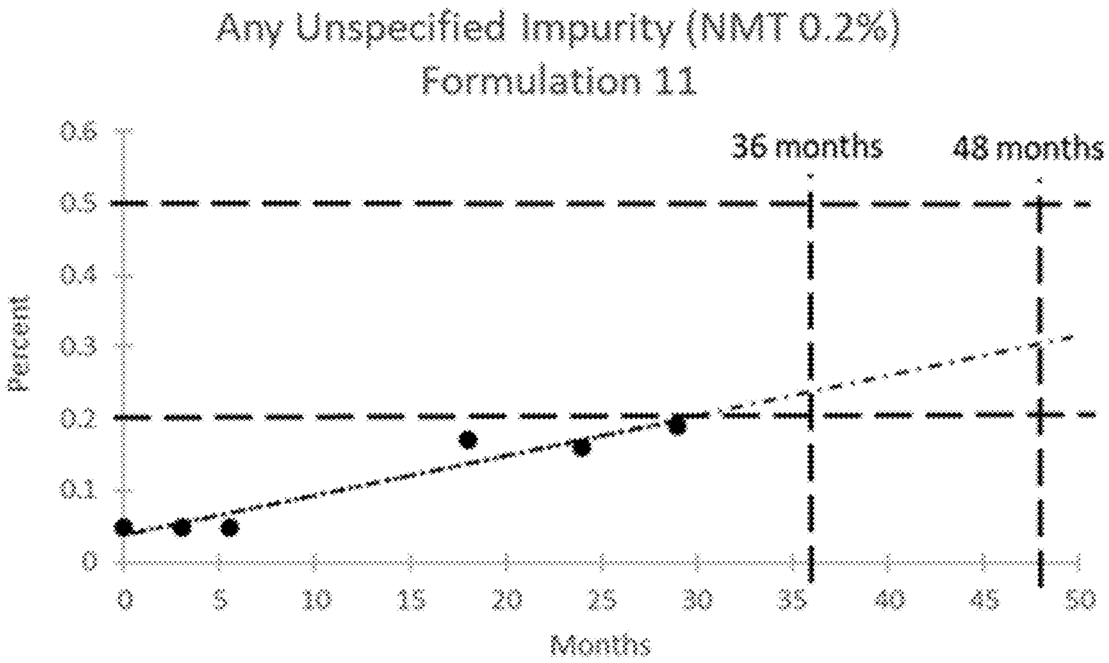
FIG. 19 demonstrates that formulation 11 (F11: 0.035 mg/ml Sodium Sulfite Anhydrous, 10.4% Oxygen headspace) is expected to cross 0.2% at about 31 months, but to be below 0.5% for 48 months (projection with 6 measured data points; up to 29 months, 25° C./60% RH).

FIG. 19: Design of Experiment formulation 11 (F11): 0.035 mg/ml Sodium Sulfite Anhydrous, 10.4% headspace oxygen. The projection with 6 measured data points shows for the formulation that the Unspecified Impurity is expected to cross 0.2% at about 31 months, but to be below 0.5% for 48 months (25° C./60% RH).

Figure 20:
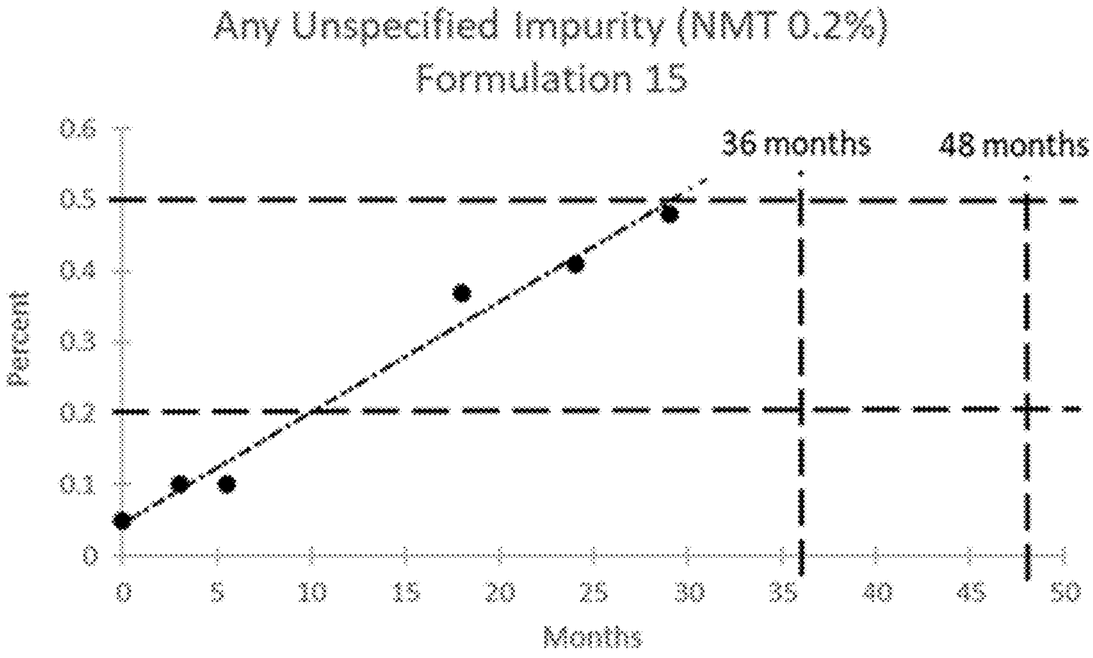
FIG. 20 demonstrates that formulation 15 (F15: 0.035 mg/ml Sodium Sulfite Anhydrous, 20.9% Oxygen headspace; atmospheric) crossed 0.2% at 10 months, and is expected to cross 0.5% at 30 months (6 measured data points; up to 29 months, 25° C./60% RH).

FIG. 20: Design of Experiment formulation 15 (F15): 0.035 mg/ml Sodium Sulfite Anhydrous, 20.9% headspace oxygen (atmospheric). The 6 measured data points shows for the formulation that the Unspecified Impurity crossed 0.2% at about 10 months, and is expected to cross 0.5% at about 30 months (25° C./60% RH).

Figure 21:
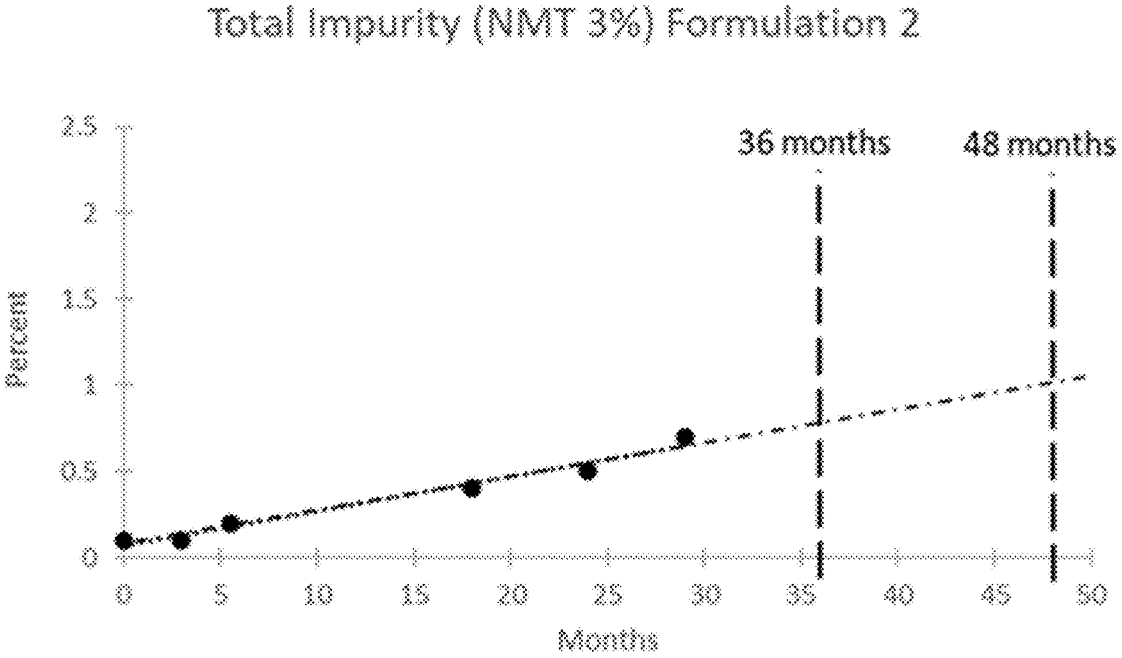
FIG. 21 demonstrates that formulation 2 (F2: 0.035 mg/ml Sodium Sulfite Anhydrous, 5.4% Oxygen headspace) is expected to be below 3% for Total Impurities for 48 months (projection with 6 measured data points; up to 29 months, 25° C./60% RH).

FIG. 21: Design of Experiment formulation 2 (F2): 0.035 mg/ml Sodium Sulfite Anhydrous, 5.4% headspace oxygen. The projection with 6 measured data points shows for the formulation that Total Impurities are expected to be below 3% for 48 months (25° C./60% RH).

Figure 22:
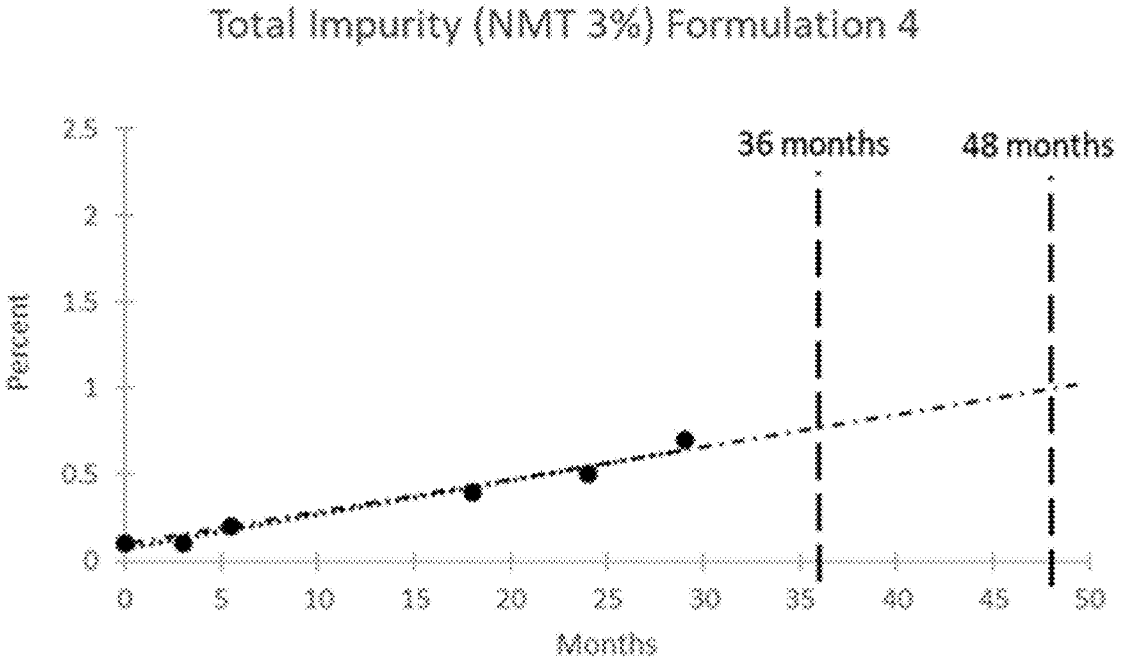
FIG. 22 demonstrates that formulation 4 (F4: 0.035 mg/ml Sodium Sulfite Anhydrous, 5.4% Oxygen headspace) is expected to be below 3% for Total Impurities for 48 months (projection with 6 measured data points; up to 29 months, 25° C./60% RH).

FIG. 22: Design of Experiment formulation 4 (F4): 0.035 mg/ml Sodium Sulfite Anhydrous, 5.4% headspace oxygen. The projection with 6 measured data points shows for the formulation that Total Impurities are expected to be below 3% for 48 months (25° C./60% RH).

Figure 23:
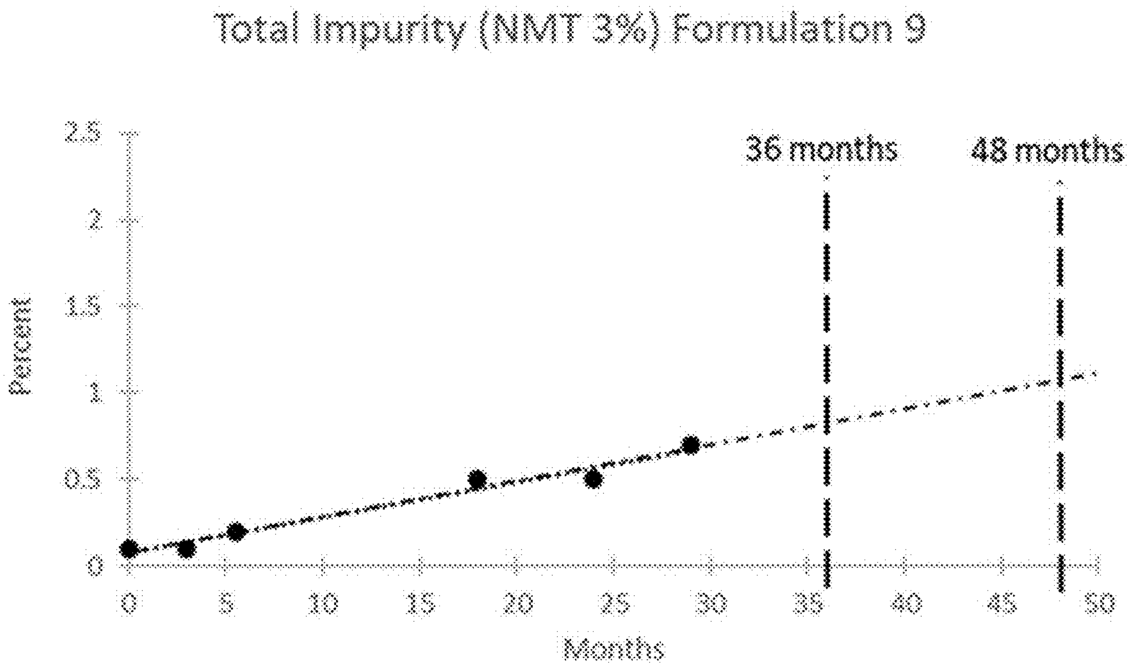
FIG. 23 demonstrates that formulation 9 (F9: 0.07 mg/ml Sodium Sulfite Anhydrous, 5.1% Oxygen headspace) is expected to be below 3% for Total Impurities for 48 months (projection with 6 measured data points; up to 29 months, 25° C./60% RH).

FIG. 23: Design of Experiment formulation 9 (F9): 0.07 mg/ml Sodium Sulfite Anhydrous, 5.1% headspace oxygen. The projection with 6 measured data points shows for the formulation that Total Impurities are expected to be below 3% for 48 months (25° C./60% RH).

Figure 24:
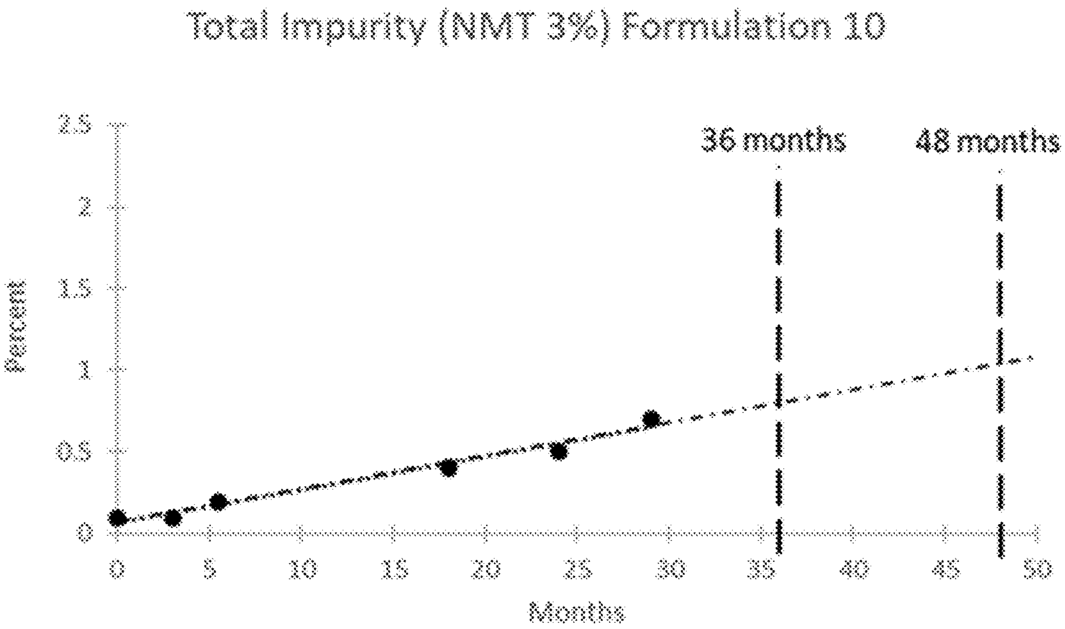
FIG. 24 demonstrates that formulation 10 (F10: 0 mg/ml Sodium Sulfite Anhydrous, 5.1% Oxygen headspace) is expected to be below 3% for Total Impurities for 48 months (projection with 6 measured data points; up to 29 months, 25° C./60% RH).

FIG. 24: Design of Experiment formulation 10 (F10): 0 mg/ml Sodium Sulfite Anhydrous, 5.1% headspace oxygen. The projection with 6 measured data points shows for the formulation that Total Impurities are expected to be below 3% for 48 months (25° C./60% RH).

Figure 25:
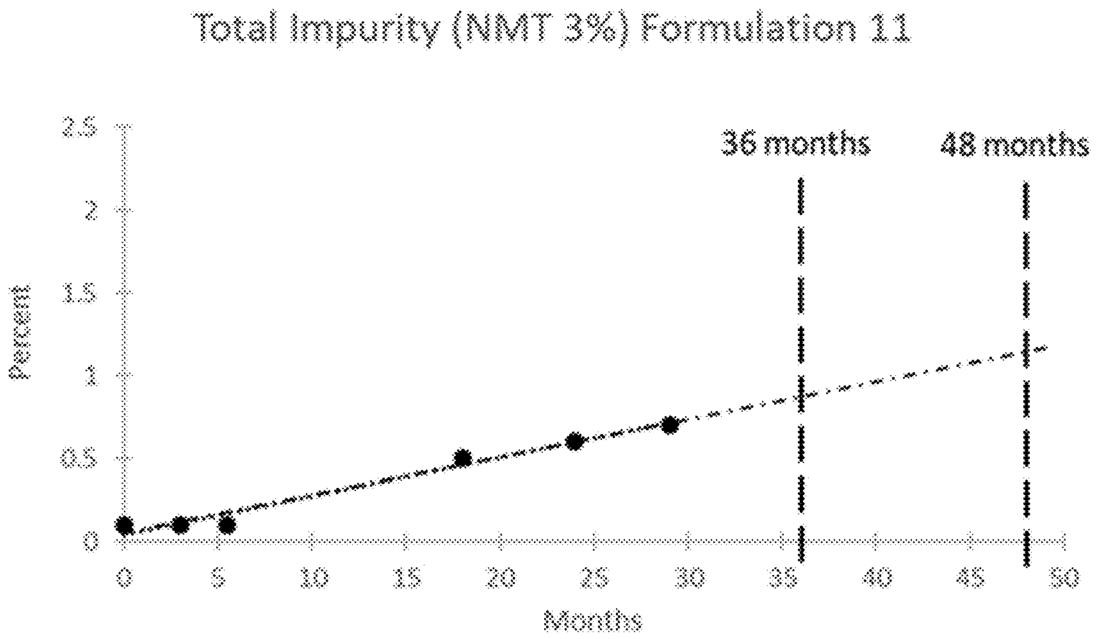
FIG. 25 demonstrates that formulation 11 (F11: 0.035 mg/ml Sodium Sulfite Anhydrous, 10.4% headspace oxygen) is expected to be below 3% for Total Impurities for 48 months (projection with 6 measured data points; up to 29 months, 25° C./60% RH).

FIG. 25: Design of Experiment formulation 11 (F11): 0.035 mg/ml Sodium Sulfite Anhydrous, 10.4% headspace oxygen. The projection with 6 measured data points shows for the formulation that Total Impurities are expected to be below 3% for 48 months (25° C./60% RH).

Figure 26:
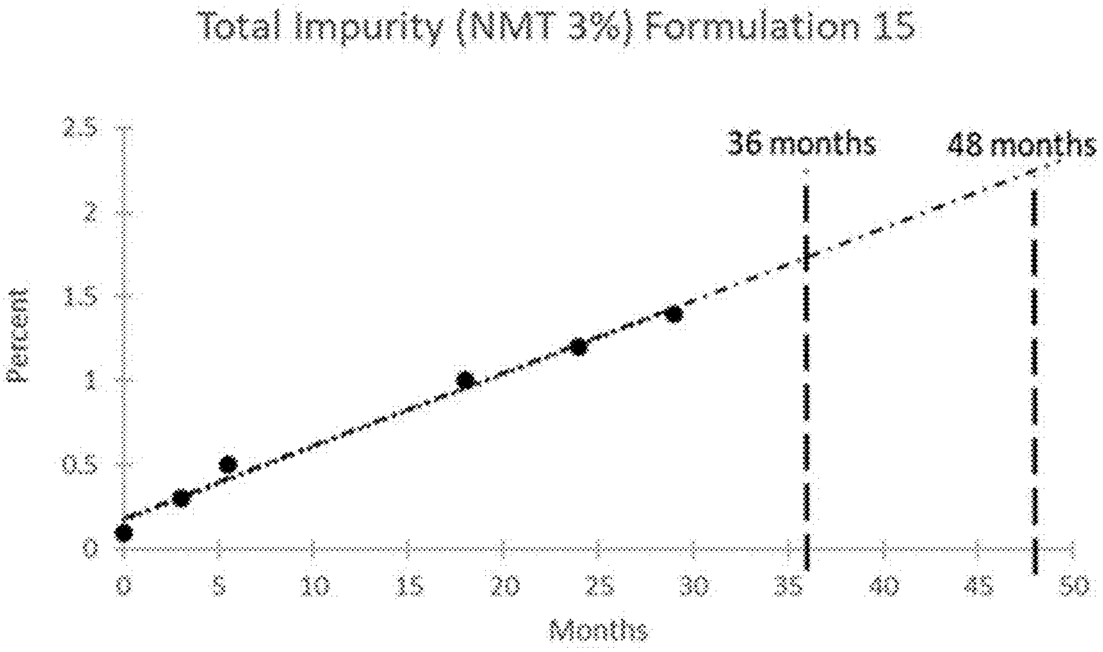
FIG. 26 demonstrates that formulation 15 (F15: 0.035 mg/ml Sodium Sulfite Anhydrous, 20.9% Oxygen headspace; atmospheric) is expected to be below 3% for Total Impurities for 48 months (projection with 6 measured data points; up to 29 months, 25° C./60% RH).

FIG. 26: Design of Experiment formulation 15 (F15): 0.035 mg/ml Sodium Sulfite Anhydrous, 20.9% headspace oxygen (atmospheric). The projection with 6 measured data points shows for the formulation that Total Impurities are expected to be below 3% for 48 months (25° C./60% RH).

Example 3

Extended DoE—Stability of formulations without Sodium Sulfite/Disodium Edetate. Design of experiment series (up to 6 months at 40° C./75% RH) to assess the stability of the formulation without the presence of either sodium sulfite or EDTA at increasing levels of headspace oxygen (O %, 5%, 10% and 15%): Ten formulations with the specifications shown in Table 8 were manufactured (GLP grade) and tested for stability. 26.23 mg/ml DSP equals 24 mg/ml Dexamethasone Phosphate. All formulations were packaged using the AVM0703 headspace volume (ml) to dexamethasone content (mg) ratio outlined in Table 1 (24 mg/ml dexamethasone phosphate; 51 ml vial; 7.2 ml headspace volume; headspace volume (ml) to dexamethasone content (mg) ratio of about 0.00588).

TABLE 8

| | | | Material | | | | |
|---|---|---|---|---|---|---|---|
| Storage Condition | Batch | Formulation | DSP (mg/ml) | Sodium Citrate (mg/ml) | Disodium Edetate (mg/ml) | Sodium Sulfite (Anhydrous) (mg/ml) | Headspace Oxygen (%) Target |
| 40° C. - Inverted | 1 | 1 | 26.23* | 10 | 0.50 | 0 | 0 |
| 40° C. - Inverted | 1 | 2 | | | | | 5 |
| 40° C. - Inverted | 1 | 3 | | | | | 10 |
| 40° C. - Inverted | 1 | 4 | | | | | 15 |
| 40° C. - Inverted | 2 | 1 | | | 0 | 0.035 | 0 |
| 40° C. - Inverted | 2 | 2 | | | | | 5 |
| 40° C. - Inverted | 2 | 3 | | | | | 10 |
| 40° C. - Inverted | 2 | 4 | | | | | 15 |
| 40° C. - Inverted | 3 | 1 | | | 0.50 | 0.035 | 0 |
| 40° C. - Inverted | 4 | 1 | | | 0 | 0 | 5 |

*Equivalent to 19.94 mg Dexamethasone and 24 mg Dexamethasone Phosphate

TABLE 9

1 month stability data (40° C./75% RH - inverted vial); All: Dexamethasone Phosphate 24 mg/ml, Sodium Citrate 10 mg/ml

| Formulation # | 1-1 | 1-2 | 1-3 | 1-4 | 2-1 | 2-2 | 2-3 | 2-4 | 3-1 | 4-1 |
|---|---|---|---|---|---|---|---|---|---|---|
| Disodium EDTA (mg/ml) | 0.5 | 0.5 | 0.5 | 0.5 | 0 | 0 | 0 | 0 | 0.5 | 0 |
| Sodium Sulfite (mg/ml) | 0 | 0 | 0 | 0 | 0.035 | 0.035 | 0.035 | 0.035 | 0.035 | 0 |
| Headspace Oxygen (%) | 0 | 5 | 10 | 15 | 0 | 5 | 10 | 15 | 0 | 5 |
| Description | Pass | Pass | Pass | Pass | Pass | Pass | Pass | Pass | Pass | Pass |
| pH | 7.7 | 7.7 | 7.6 | 7.6 | 7.8 | 7.8 | 7.8 | 7.7 | 7.7 | 7.7 |
| Assay (%) | 98.6 | 98.3 | 98.2 | 97.8 | 97.5 | 97.3 | 97.8 | 97.4 | 97.6 | 96.5 |

TABLE 9-continued

| 1 month stability data (40° C./75% RH - inverted vial); All: Dexamethasone Phosphate 24 mg/ml, Sodium Citrate 10 mg/ml | | | | | | | | | | |
|---|---|---|---|---|---|---|---|---|---|---|
| Formulation # | 1-1 | 1-2 | 1-3 | 1-4 | 2-1 | 2-2 | 2-3 | 2-4 | 3-1 | 4-1 |
| Impurity A (%) (NMT 1%) | 0.15 | 0.13 | 0.11 | 0.11 | 0.13 | 0.13 | 0.13 | 0.13 | 0.17 | 0.12 |
| Impurity B (%) (NMT 0.5%) | 0.07 | 0.07 | 0.07 | 0.07 | 0.07 | 0.07 | 0.07 | 0.07 | 0.07 | 0.07 |
| Impurity C (%) (NMT 0.5%) | 0.1 | 0.1 | 0.09 | 0.09 | 0.11 | 0.11 | 0.1 | 0.1 | 0.1 | 0.1 |
| Impurity D (%) (NMT 0.5%) | <0.05 | <0.0 | <0.05 | <0.05 | <0.05 | <0.05 | <0.05 | <0.05 | <0.05 | <0.05 |
| Impurity F (%) (NMT 0.5%) | 0.06 | 0.06 | 0.06 | 0.06 | 0.07 | 0.07 | 0.07 | 0.07 | 0.07 | 0.07 |
| Impurity G (%) (NMT 0.5%) | 0.16 | 0.18 | 0.19 | 0.19 | 0.15 | 0.19 | 0.2 | 0.21 | 0.15 | 0.18 |
| Any unspecified impurity (%) (NMT 0.2%) | 0.1 | 0.09 | 0.1 | 0.1 | 0.1 | 0.1 | 0.09 | 0.09 | 0.1 | 0.1 |
| Total impurities (%) (NMT 3.0%) | 0.6 | 0.7 | 0.7 | 0.7 | 0.6 | 0.7 | 0.7 | 0.7 | 0.7 | 0.7 |

Design of experiment (Extended DoE) result for 1 month, either lacking sodium sulfite or disodium edetate or both (Table 9). Ten (all: 24 mg/ml as Dexamethasone Phosphate equivalent which corresponds to 26.23 DSP mg/ml; 10 mg/ml sodium citrate) formulations with two different levels (0 or 0.035 mg/ml) of sodium sulfite (anhydrous), two different levels of disodium edetate (0 or 0.5 mg/ml) and four different levels of headspace oxygen (0, 5, 10, 15%) were tested for stability (40° C./75% RH). Formulations 1-1, 1-2, 1-3 and 1-4 lack sodium sulfite (anhydrous), contain 0.5 mg/ml disodium edetate and increasing amounts of headspace oxygen (1-1: 0%, 1-2: 5%, 1-3: 10%, 1-4: 15%). Formulations 2-1, 2-2, 2-3 and 2-4 lack disodium edetate, contain 0.035 mg/ml sodium sulfite (anhydrous) and increasing amounts of headspace oxygen (2-1: 0%, 2-2: 5%, 2-3: 10%, 2-4: 15%). Formulation 3-1 contains 0.035 mg/ml sodium sulfite (anhydrous) and 0.5 mg/ml disodium edetate, but lacks headspace oxygen. Formulation 4-1 lacks sodium sulfite (anhydrous) and disodium edetate and contains 5% headspace oxygen. The result demonstrates that all ten formulations are within a range of 95-105% for the DSP content as well as within the set thresholds for the known (A: not more than 1%; B, C, D, F and G: not more than 0.5%) and unknown impurities (not more than 0.2%), with 'Total Impurity' values far below the threshold of 3% (storage conditions are 40° C./75% RH, inverted).

Design of experiment (Extended DoE) result for 1, 3, and 6 months, either lacking sodium sulfite or disodium edetate or both (FIGS. 28-44). While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. Those three formulations (2-1, 2-2 and 3-1) were all within the acceptance criteria of the DSP assay (95-105%).

FIG. 28: Design of experiment result for the DSP assay (up to 6 months at 40° C./75% RH; 26.23 mg/ml DSP=24 mg/ml DP) to assess the stability of the formulation without the presence of either sodium sulfite or EDTA at increasing levels of headspace oxygen (=HO: 0%, 5%, 10% and 15%): All ten formulations contained 26.23 mg/ml DSP, which is equivalent to 24 mg/ml Dexamethasone Phosphate (DP). While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. The top chart shows the result of the DSP assay with the absolute values in percent, while the bottom chart depicts the difference in percent at 1, 3 and 6 months subtracted from the 0 months value (manufacture). The result shows that formulation 2-1 shows the least degradation of all formulations at the 6 months time point while still passing description (no precipitation).

FIGS. 29 & 30: Design of experiment result for the impurities A and B (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. FIG. 29 shows the result of impurity A, while FIG. 30 depicts impurity B. The result shows that formulation 2-1 showed the lowest accumulation of impurity A (Dexamethasone) of all formulations at the 6 months time point. Impurity B was not increasing for any of the formulations.

FIGS. 31 & 32: Design of experiment result for the impurites C and D (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. FIG. 31 shows the result of impurity C, while FIG. 32 depicts impurity D. The result shows that the formulations with the highest headspace oxygen value showed the lowest accumulation of impurity C of all formulations at the 6 months time point. Impurity D increased the most from the 3 month time point to the 6 month time point for all formulations. Formulation 3-1 with sulfite and EDTA present at 0% headspace oxygen (HO) had the lowest value at 6 months of those 3 formulations that passed the description without a precipitate.

FIGS. 33 & 34: Design of experiment result for the impurites F and G (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. FIG. 33 shows the result of impurity F, while FIG. 34 depicts impurity G. The result shows that none of the formulations increase for impurity F beyond the 0.2% threshold. Regarding impurity G, formulation 2-1 showed the lowest accumulation of all formulations at the 6 months time point.

FIGS. 35 & 36: Design of experiment result for the unidentified impurity with the highest value and the total impurities (up to 6 months at 40° C./75% RH; 26.23 mg/ml DSP=24 mg/ml DP): While all ten formulations passed the description at 3 months, only the following formulations passed the description as a clear solution at the 6 months stability time point: (batch #-formulation #) 2-1 (0.035 mg/ml sodium sulfite, 0 mg/ml EDTA, 0% headspace oxygen), 2-2 (0.035 mg/ml sodium sulfite, 0 mg/ml EDTA, 5% headspace oxygen) and 3-1 (0.035 mg/ml sodium sulfite, 0.5 mg/ml EDTA, 0% headspace oxygen). All others showed precipitation at 6 months. FIG. 35 shows the result for the unidentified impurity with the highest value, while FIG. 36 depicts total impurities, which are the sum total of all previous impurities (A, B, C, D, F, G, highest unidentified impurity) as well as additionally all other unidentified impurities (with different retention times) that are of lower value. The result shows that the two sulfite formulations (of all three without precipitation at 6 months) lacking EDTA (2-1, 2-2) show the lowest values of the highest unidentified impurity. Likewise, these same two formulations (2-1 and 2-2) are characterized by the lowest amount of total impurities. Therefore, for this formulation no EDTA is needed at a storage condition of 40° C./75% RH at 0 or 5% headspace oxygen.

Figure 37:
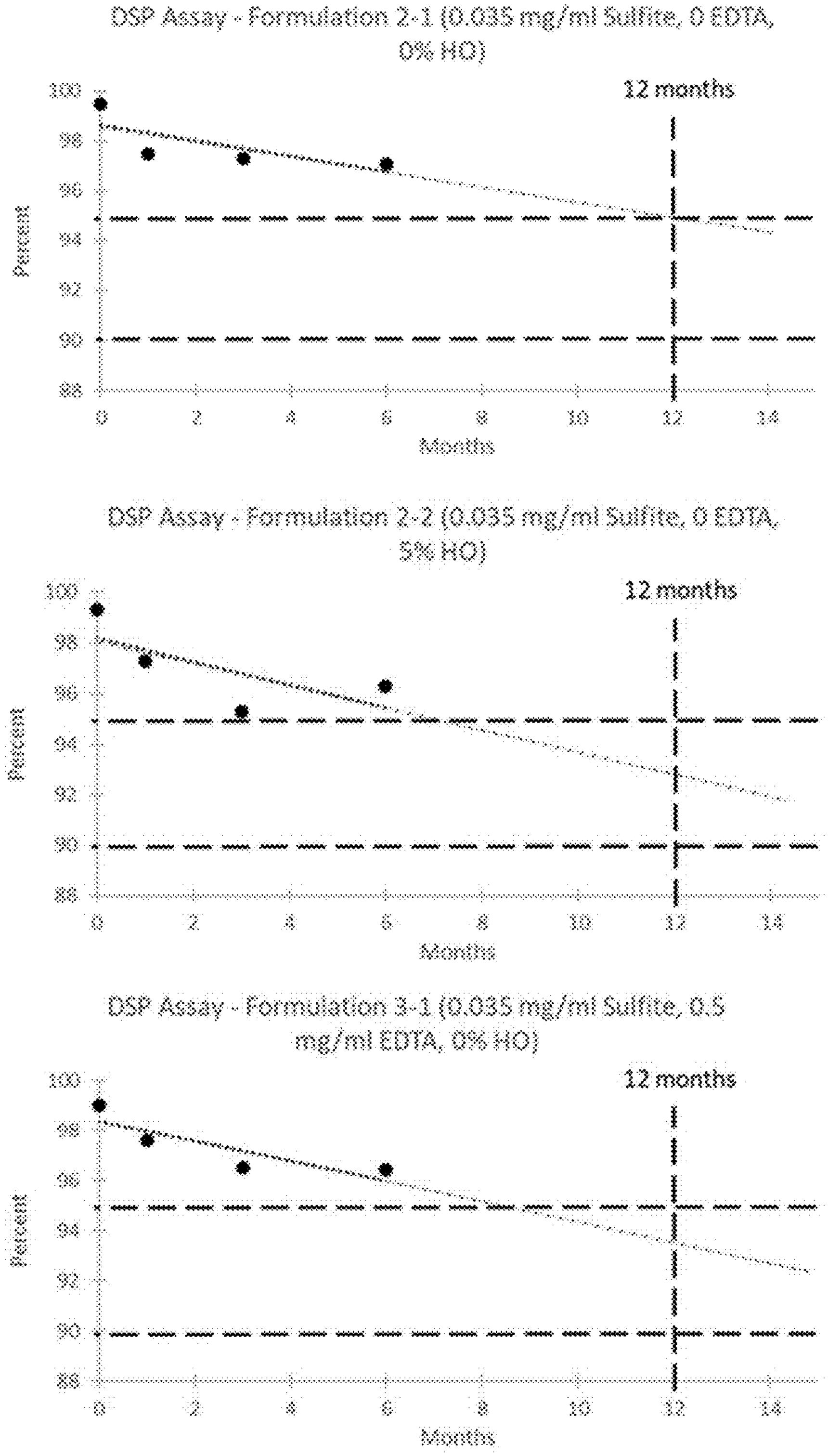

FIG. 37: DSP result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Dexamethasone Sodium Phosphate content is expected to be at 95% for 12 months (40° C./75% RH) for the formulation 2-1, while 2-2 and 3-1 are expected to be at a level of about 93% and 93.5% respectively. The result shows that EDTA is not necessary to achieve a better stability for the formulation.

FIG. 38: Impurity A result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Impurity A level is expected to be below 1% for 12 months (40° C./75% RH) for the formulation 2-1 and 2-2, while for formulation 3-1 it is expected to reach 1% at about 9 months. The result shows that EDTA is not necessary to achieve a better stability for the formulation.

FIG. 39: Impurity C result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows for the formulations that the Impurity C level is expected to be at 0.5% for 12 months (40° C./75% RH) for the formulation 2-1, while being slightly below 0.5% for formulation 2-2 and 3-1 at this time point.

FIG. 40: Impurity D result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity D level is expected to be below 0.5% at 12 months (40° C./75% RH) for all 3 formulations.

FIG. 41: Impurity F result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity F level is expected to be below 0.5% at 12 months (40° C./75% RH) for all 3 formulations.

FIG. 42: Impurity G result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the Impurity G level is expected to be below 0.5% at 12 months (40° C./75% RH) for all 3 formulations.

FIG. 43: Unidentified Impurity result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the level of the Unidentified Impurity is expected to be below 0.5% at 12 months (40° C./75% RH) for all 3 formulations. Moreover, the two formulations lacking EDTA (2-1 and 2-2) show an expected level even below 0.2% at 12 months.

FIG. 44: Total Impurities result and projection of additional Design of Experiment formulations 2-1 (0.035 mg/ml Sodium Sulfite Anhydrous, 0 mg/ml EDTA and 0% Oxygen headspace), 2-2 (0.035 mg/ml Sodium Sulfite Anhydrous, 0 mg/ml EDTA and 5% headspace oxygen) and 3-1 (0.035 mg/ml Sodium Sulfite Anhydrous, 0.5 mg/ml EDTA and 0% headspace oxygen). The projection with 4 measured (up to 6 months) data points shows that the level of the Total Impurities is expected to be below 3% at 12 months (40° C./75% RH) for the two formulations lacking the EDTA (2-1, 2-2), while reaching 3% for the formulation 3-1 with sulfite and EDTA present. The result demonstrates that EDTA is not necessary to increase the stability of the formulation.

Example 4

Six formulations with 3 varying levels of DSP (10, 30 and 45 mg/ml, equivalent to 9.15, 27.45 and 41.17 Dexamethsone Phosphate (DP)) with or without 0.5 mg/ml EDTA, respectively, were manufactured. The compositions of these six formulations is outlined in Tables 10 and 11. The formulations in Batch 1 and 2 (Table 10) were packaged with a headspace volume (ml) to dexamethasone content (mg) of 0.01543 (10 mg/ml dexamethasone sodium phosphate, equivalent to 9.15 mg/ml dexamethasone phosphate; 51 ml vial; 7.2 ml headspace volume; headspace volume (ml) to dexamethasone content (mg) ratio of about 0.01543). The formulations in Batch 3 and 4 (Table 10) were packaged with a headspace volume (ml) to dexamethasone content (mg) of 0.0514 (30 mg/ml dexamethasone sodium phosphate, equivalent to 27.45 mg/ml dexamethasone phosphate; 51 ml vial; 7.2 ml headspace volume; headspace volume (ml) to dexamethasone content (mg) ratio of about 0.00514). The formulations in Batch 1 and 2 (Table 11) were packaged with a headspace volume (ml) to dexamethasone content (mg) of 0.00343 (45 mg/ml dexamethasone sodium phosphate, equivalent to 41.17 mg/ml dexamethasone phosphate; 51 ml vial; 7.2 ml headspace volume; headspace volume (ml) to dexamethasone content (mg) ratio of about 0.00343).

TABLE 10

| | | Material | | | | |
|---|---|---|---|---|---|---|
| Storage Condition | Batch | DSP (mg/ml) | Sodium Citrate (mg/ml) | Disodium Edetate (mg/ml) | Sodium Sulfite (Anhydrous) (mg/ml) | Headspace Oxygen (%) Target |
| 40° C. - Inverted | 1 | 10 | 10 | 0.50 | 0 | 5 |
| 40° C. - Inverted | 2 | | | 0 | | |
| 40° C. - Inverted | 3 | 30 | | 0.50 | | |
| 40° C. - Inverted | 4 | | | 0 | | |

TABLE 11

| | | Material | | | | |
|---|---|---|---|---|---|---|
| Storage Condition | Batch | DSP (mg/ml) | Sodium Citrate (mg/ml) | Disodium Edetate (mg/ml) | Sodium Sulfite (Anhydrous) (mg/ml) | Headspace Oxygen (%) Target |
| 40° C. - Inverted | 1 | 45* | 10 | 0.50 | 0 | 5 |
| 40° C. - Inverted | 2 | | | 0 | | |

*Equivalent to 34.20 mg Dexamethasone and 41.17 mg Dexamethasone Phosphate

Results of the additional design of experiment for increasing concentrations of Dexamethasone Sodium Phosphate (DSP). Six formulations with 3 varying levels of DSP (10, 30 and 45 mg/ml, equivalent to 9.15, 27.45 and 41.17 Dexamethsone Phosphate (DP)) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. The results demonstrates that the formulations with an increasing DSP concentration form less total impurities over time. An overview of these results is shown in Table 12.

TABLE 12

| | | | | 40° C. - Inverted | | | | | | | | Assay DSP) | | | |
|---|---|---|---|---|---|---|---|---|---|---|---|---|---|---|---|
| | DSP | EDTA | | Description | | | | pH | | | | (95.0-105.0%) | | | |
| Batch # | mg/ml | mg/ml | months | 0 | 1 | 3 | 6 | 0 | 1 | 3 | 6 | 0 | 1 | 3 | 6 |
| 1 | 10 | + | | Pass | Pass | Fail | Fail | 7.6 | 7.6 | 7.6 | 7.6 | 99.7 | 98.2 | 97.9 | 96.5 |
| 2 | 10 | − | | Pass | Pass | Fail | Fail | 7.6 | 7.7 | 7.7 | 7.7 | 98.5 | 97.6 | 97.3 | 95.4 |
| 3 | 30 | + | | Pass | Fail | Fail | Fail | 7.6 | 7.6 | 7.6 | 7.7 | 95.9 | 94.7 | 94.8 | 93.3 |
| 4 | 30 | − | | Pass | Pass | Fail | Fail | 7.7 | 7.6 | 7.6 | 7.7 | 94.6 | 93.5 | 94.2 | 92.3 |

TABLE 12-continued

| | | | | | | | | | | | | | | | |
|---|---|---|---|---|---|---|---|---|---|---|---|---|---|---|---|
| 1 | 45 | + | | Pass | Pass | Pass | Fail | 7.7 | 7.7 | 7.7 | 7.7 | 97.3 | 96.8 | 96.6 | 95.4 |
| 2 | 45 | − | | Pass | Pass | Pass | Fail | 7.7 | 7.7 | 7.6 | 7.7 | 97.7 | 96.9 | 96.7 | 96.4 |

| | | | | 40° C. - Inverted | | | | | | | | | | | |
|---|---|---|---|---|---|---|---|---|---|---|---|---|---|---|---|
| | DSP | EDTA | | Impurity A (%) | | | | Impurity B (%) | | | | Impurity C (%) | | | |
| Batch # | mg/ml | mg/ml | months | 0 | 1 | 3 | 6 | 0 | 1 | 3 | 6 | 0 | 1 | 3 | 6 |
| 1 | 10 | + | | <0.05 | 0.16 | 0.27 | 0.58 | 0.08 | 0.07 | 0.06 | 0.06 | 0.05 | 0.11 | 0.22 | 0.31 |
| 2 | 10 | − | | <0.05 | 0.17 | 0.31 | 0.47 | 0.09 | 0.07 | 0.07 | 0.06 | 0.05 | 0.11 | 0.19 | 0.24 |
| 3 | 30 | + | | <0.05 | 0.16 | 0.41 | 0.75 | 0.08 | 0.07 | 0.07 | 0.07 | 0.05 | 0.1 | 0.18 | 0.24 |
| 4 | 30 | − | | <0.05 | 0.13 | 0.32 | 0.64 | 0.09 | 0.07 | 0.07 | 0.07 | 0.05 | 0.1 | 0.16 | 0.22 |
| 1 | 45 | + | | <0.05 | 0.15 | 0.34 | 0.62 | 0.08 | 0.08 | 0.08 | 0.07 | 0.05 | 0.1 | 0.16 | 0.21 |
| 2 | 45 | − | | <0.05 | 0.14 | 0.37 | 0.64 | 0.08 | 0.08 | 0.08 | 0.07 | 0.05 | 0.09 | 0.15 | 0.19 |

| | | | | 40° C. - Inverted | | | | | | | | | | | |
|---|---|---|---|---|---|---|---|---|---|---|---|---|---|---|---|
| | DSP | EDTA | | Impurity D (%) | | | | Impurity E (%) | | | | Impurity F (%) | | | |
| Batch # | mg/ml | mg/ml | months | 0 | 1 | 3 | 6 | 0 | 1 | 3 | 6 | 0 | 1 | 3 | 6 |
| 1 | 10 | + | | <0.05 | <0.05 | 0.05 | 0.14 | 0.05 | <0.05 | <0.05 | <0.05 | <0.05 | 0.07 | 0.1 | 0.13 |
| 2 | 10 | − | | <0.05 | <0.05 | 0.09 | 0.23 | 0.05 | <0.05 | <0.05 | <0.05 | <0.05 | 0.07 | 0.1 | 0.14 |
| 3 | 30 | + | | <0.05 | <0.05 | 0.07 | 0.18 | 0.05 | <0.05 | <0.05 | <0.05 | <0.05 | 0.07 | 0.09 | 0.12 |
| 4 | 30 | − | | <0.05 | <0.05 | 0.07 | 0.2 | <0.05 | <0.05 | <0.05 | <0.05 | <0.05 | 0.07 | 0.09 | 0.13 |
| 1 | 45 | + | | <0.05 | <0.05 | 0.08 | 0.2 | 0.05 | <0.05 | <0.05 | <0.05 | <0.05 | 0.07 | 0.09 | 0.12 |
| 2 | 45 | − | | <0.05 | <0.05 | 0.09 | 0.21 | 0.05 | <0.05 | <0.05 | <0.05 | <0.05 | 0.07 | 0.09 | 0.13 |

| | | | | 40° C. - Inverted | | | | | | | | | | | |
|---|---|---|---|---|---|---|---|---|---|---|---|---|---|---|---|
| | DSP | EDTA | | Impurity G (%) | | | | Unspecified Impurity (%) | | | | Total Impurities (%) | | | |
| Batch # | mg/ml | mg/ml | months | 0 | 1 | 3 | 6 | 0 | 1 | 3 | 6 | 0 | 1 | 3 | 6 |
| 1 | 10 | + | | 0.16 | 0.16 | 0.22 | 0.23 | 0.11 | 0.11 | 0.11 | 0.11 | 0.4 | 0.7 | 1.3 | 2.1 |
| 2 | 10 | − | | 0.15 | 0.16 | 0.22 | 0.29 | 0.11 | 0.11 | 0.1 | 0.1 | 0.4 | 0.7 | 1.2 | 1.9 |
| 3 | 30 | + | | 0.16 | 0.17 | 0.18 | 0.2 | 0.11 | 0.11 | 0.11 | 0.11 | 0.4 | 0.7 | 1.2 | 1.9 |
| 4 | 30 | − | | 0.16 | 0.18 | 0.18 | 0.2 | 0.11 | 0.11 | 0.11 | 0.1 | 0.4 | 0.7 | 1.1 | 1.7 |
| 1 | 45 | + | | 0.16 | 0.17 | 0.17 | 0.18 | 0.11 | 0.11 | 0.11 | 0.1 | 0.4 | 0.7 | 1.1 | 1.7 |
| 2 | 45 | − | | 0.16 | 0.17 | 0.18 | 0.2 | 0.11 | 0.1 | 0.11 | 0.1 | 0.4 | 0.7 | 1.1 | 1.6 |

Figure 46:
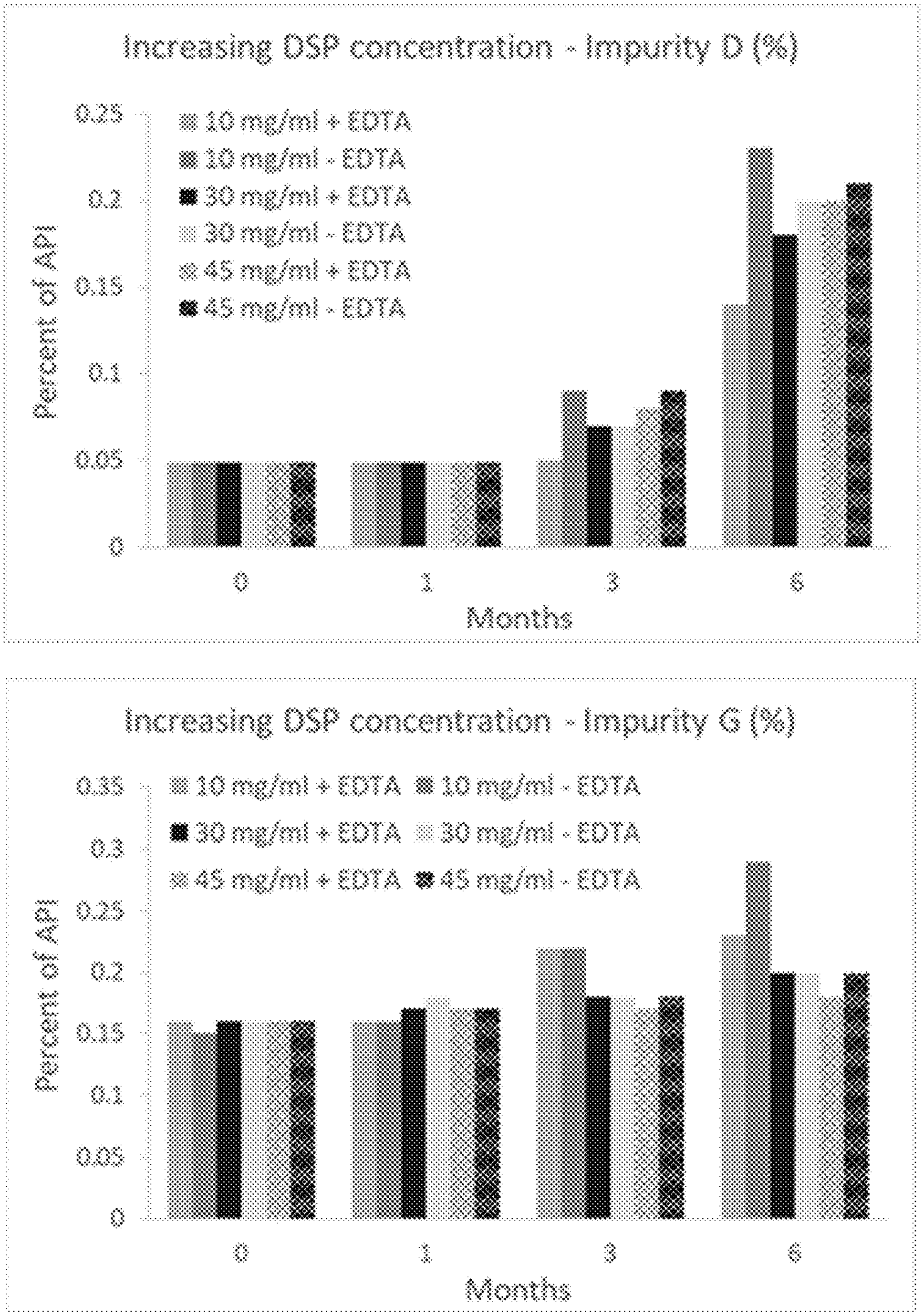

FIG. 45 & FIG. 46: Results of the additional design of experiment for increasing concentrations of the active pharmaceutical ingredient (API) in the AVM0703 formulation: Dexamethasone Sodium Phosphate (DSP). Six formulations with 3 varying levels of DSP (10, 30 and 45 mg/ml) with or without 0.5 mg/ml EDTA, respectively, were manufactured and put on stability (50 ml amber vial; 0, 1, 3, 6 months at 40° C./75% RH). All 6 formulations contained 5% headspace oxygen (95% nitrogen) and lacked sulfite. While there is a clear decrease of impurities C and G for all formulations over 6 months, there seems to be no clear trend for impurity A in the formulations including EDTA or impurity D in the formulations lacking EDTA. For impurity A in the formulation lacking EDTA there is an initial increase visible that eventually stagnates, while for impurity D in the formulations including EDTA there is a visible increase over time up to ~0.2%.

FIG. 47: Design of experiment result (0, 1, 3, 6 months at 40° C./75% RH) for increasing concentrations of the active pharmaceutical ingredient (API) in the AVM0703 formulation: Dexamethasone Sodium Phosphate (DSP). Six formulations with 3 varying levels of DSP (10, 30 and 45 mg/ml, equivalent to 9.15, 27.45 and 41.17 Dexamethsone Phosphate), with or without 0.5 mg/ml EDTA and each containing 5% headspace oxygen (95% nitrogen) were tested for stability. All six formulations lacked sulfite. The top chart includes all formulations, while the middle and bottom each depict the 3 formulations either with (middle) or without EDTA (bottom). The formulations with the highest DSP content of 45 mg/ml still passed the description at 3 months, while all other failed and showed a precipitate. The result demonstrates that the formulations with an increasing DSP concentration form less total impurities over time, independent of the presence or absence of EDTA.

Supplementary Tables

TABLE A

Examples of Dexamethasone Sodium Phosphate injectables including excipient/vial profile (U.S.) - For Human Use (US)

| PRODUCT NDC | PROPRIETARY NAME | DOSAGE FORM NAME | LABELER NAME | Strength | Unit | Excipients | Vial |
|---|---|---|---|---|---|---|---|
| 0641-0367 | Dexamethasone Sodium Phosphate | INJECTION | West-Ward Pharmaceuticals Corp. | 10 | mg/mL | Sodium Sulfite (1.5 mg in 1 mL) (UNII: VTK01UQK3G); Sodium Citrate (16.5 mg in 1 mL) (UNII: 1Q73Q2JULR); Benzyl Alcohol (10.42 mg in 1 mL) (UNII: LKG8494WBH); | 1 ml |

TABLE A-continued

| PRODUCT NDC | PROPRIETARY NAME | DOSAGE FORM NAME | LABELER NAME | Strength | Unit | Excipients | Vial |
|---|---|---|---|---|---|---|---|
| Examples of Dexamethasone Sodium Phosphate injectables including excipient/vial profile (U.S.) - For Human Use (US) | | | | | | | |
| | | | | | | Water (UNII: 059QF0KO0R); Sodium Hydroxide (UNII: 55X04QC321) Citric Acid Monohydrate (UNII: 2968PHW8QP) | |
| 0641-0367-25 | Dexameth-asone Sodium Phosphate | INJECTION | West-Ward Pharmaceuticals Corp. | 10 | mg/mL | Sodium Sulfite (1.5 mg in 1 mL) (UNII: VTK01UQK3G); Sodium Citrate (16.5 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 2968PHW8QP) | 1 ml |
| 52584-420 | Dexameth-asone Sodium Phosphate | INJECTION, SOLUTION | General Injectables and Vaccines, Inc. | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) | 10 ml |
| 54868-6099-0 | DEXAMETH-ASONE Sodium Phosphate | INJECTION | Physicians Total Care, Inc. | 10 | mg/mL | Anhydrous Trisodium Citrate (10 mg in 1 mL) (UNII: RS7A450LGA); Sodium Metabisulfite (1 mg in 1 mL) (UNII: 4VON5FNS3C); Benzyl Alcohol (10 mg in 1 mL) (UNII: LKG8494WBH); Water (UNII: 059QF0KO0R); Citric Acid Monohydrate (UNII: 2968PHW8QP) | 10 ml |
| 55154-5118 | Dexameth-asone Sodium Phosphate | INJECTION | Cardinal Health | 10 | mg/mL | Sodium Sulfite Anhydrous (1.5 mg in 1 mL) (UNII: 36KCS0R750); Anhydrous Trisodium Citrate (16.5 mg in 1 mL) (UNII: RS7A450LGA); Benzyl Alcohol (10.42 mg in 1 mL) (UNII: LKG8494WBH); Water (UNII: 059QF0KO0R); Sodium Hydroxide (UNII: 55X04QC321); Citric Acid Monohydrate (UNII: 2968PHW8QP) | 1 ml |
| 55154-9371 | Dexameth-asone Sodium Phosphate | INJECTION, SOLUTION | Cardinal Health | 10 | mg/mL | Sodium Citrate, Unspecified Form (24.75 mg in 1 mL) (UNII: 1Q73Q2JULR); Citric Acid Monohydrate (UNII: 2968PHW8QP); Sodium Hydroxide (UNII: 55X04QC321) | 1 ml |
| 63323-506-01 | Dexameth-asone Sodium Phosphate | INJECTION, SOLUTION | Fresenius Kabi USA, LLC | 10 | mg/mL | Sodium Citrate (24.75 mg in 1 mL) (UNII: 1Q73Q2JULR); Sodium Hydroxide (UNII: 55X04QC321) Citric Acid Monohydrate (UNII: 2968PHW8QP) | 1 ml |
| 63323-516-10 | Dexameth-asone Sodium Phosphate | INJECTION, SOLUTION | Fresenius Kabi USA, LLC | 10 | mg/mL | Sodium Citrate (13.5 mg in 1 mL) (UNII: 1Q73Q2JULR); Benzyl Alcohol (10 mg in 1 mL) (UNII: LKG8494WBH); Sodium Hydroxide (UNII: 55X04QC321) Citric Acid Monohydrate (UNII: 2968PHW8QP) | 10 ml |
| 67457-420-00 | Dexameth-asone Sodium Phosphate | INJECTION, SOLUTION | Mylan Institutional LLC | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) | 10 ml |
| 70069-021 | Dexameth-asone Sodium Phosphate | INJECTION | Somerset Therapeutics, LLC | 10 | mg/mL | Trisodium Citrate Dihydrate (24.75 mg in 1 mL) (UNII: B22547B95K), Citric Acid Monohydrate (UNII: 2968PHW8QP), Sodium Hydroxide (UNII: 55X04QC32I), Water (UNII: 059QF0KO0R) | 1 ml |
| 70518-0532 | Dexameth-asone Sodium Phosphate | INJECTION | REMEDYREPACK INC. | 10 | mg/mL | Sodium Sulfite (1.5 mg in 1 mL) (UNII: VTK01UQK3G), Sodium Citrate (16.5 mg in 1 mL) (UNII: 1Q73Q2JULR), Benzyl Alcohol (10.42 mg in 1 mL) (UNII: LKG8 49 4WBH), Water (UNII: 059QF0KO0R), Sodium Hydoxide (UNII: 55X04QC32I), Citric Acid Monohydrate (UNII: 2968PHW8QP) | 1 ml |
| 71872-7090 | Dexameth-asone Sodium Phosphate | INJECTION, SOLUTION | Medical Purchasing Solutions, LLC | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Citric Acid Monohydrate (UNII: 2968PHW8QP); Sodium | 10 ml |

TABLE A-continued

Examples of Dexamethasone Sodium Phosphate injectables including excipient/vial profile (U.S.) - For Human Use (US)

| PRODUCT NDC | PROPRIETARY NAME | DOSAGE FORM NAME | LABELER NAME | Strength | Unit | Excipients | Vial |
|---|---|---|---|---|---|---|---|
| | | | | | | Hydroxide (UNIIL 55X04QC321); Water (UNII: 059QF0KO0R) | |
| 71872-7091 | Dexameth-asone Sodium Phosphate | INJECTION | Medical Purchasing Solutions, LLC | 10 | mg/mL | Sodium Sulfite (1.5 mg in 1 mL) (UnII: VTK01UQK3G); Sodium Citrate (16.5 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 296PHW8QP) | 1 ml |
| 76420-270 | DMT SUIK | INJECTION, SOLUTION | Asclemed USA, Inc. | 10 | mg/mL | Sodium Citrate (UNII: 1Q73Q2JULR), Citric Acid Monohydrate (UNII: 2968PHW8QP), Sodium Hydroxide (UNII: 55X04QC32I) | 1 ml |
| 69677-071 | MAS CARE-PAK DEXAMETH-ASONE | KIT | MAS Management Group Inc. | 10 | mg/mL | SODIUM HYDROXIDE (UNII: 55X04QC32I), SODIUM CITRATE (24.5 mg in 1 mL)(UNII: 1Q73Q2JULR), CITRIC ACID MONOHYDRATE (UNII: 2968PHW8QP) | 1 ml |
| 53225-3660 | ReadySharp Dexameth-asone | INJECTION | Terrain Pharmaceuticals | 10 | mg/mL | SODIUM SULFITE (1.5 mg in 1 mL) (UNII: VTK01UQK3G), SODIUM CITRATE (16.5 mg in 1 mL) (UNII: 1Q73Q2JULR), BENZYL ALCOHOL (10.42 mg in 1 mL) (UNII: LKG8 49 4WBH), WATER (UNII: 059QF0KO0R), SODIUM HYDROXIDE (UNII: 55X04QC32I), CITRIC ACID MONOHYDRATE (UNII: 2968PHW8QP) | 1 ml |
| 76420-810 | Mardex 25 Kit | KIT; 1 ml vial part of kit; Size 50060163323-506-0110 mg/mL1 mLPackaged in twenty-fives | Asclemed USA, Inc. | 10 | mg/mL | Sodium Citrate (UNII: 1Q73Q2JULR), Citric Acid Monohydrate (UNII: 2968PHW8QP), Sodium Hydroxide (UNII: 55X04QC32I) | 1 ml vial; |
| 70112-555 | TopiDex | KIT | Topicare Management, LLC | 10 | mg/mL | SODIUM HYDROXIDE (UNII: 55X04QC32I), SODIUM CITRATE (24.5 mg in 1 mL) (UNII: 1Q73Q2JULR), CITRIC ACID MONOHYDRATE (UNII: 2968PHW8QP) | 1 ml |
| 0641-6146-01 | DEXAMETH-ASONE SODIUM PHOSPHATE | | West-Ward Pharmaceuticals Corp. | 4 | mg/ml | Sodium Sulfite Anhydrous (1 mg/ml), sodium citrate anhydrous (19.4 mg/ml) and (0.01 mL) benzyl alcohol 10.42 mg/ml (preservative) in Water for Injection. | 5 ml |
| 0006-7646-03 (with-drawn) | DECADRON Phosphate injection | INJECTION, SOLUTION | Merck | 24 | mg/ml | 8 mg/ml creatinine, 10 mg/ml sodium citrate, 0.5 mg/ml disodium edetate, sodium hydroxide to adjust pH, and Water for Injection q.s., with 1 mg/ml sodium bisulfite, 1.5 mg/ml methylparaben, and 0.2 mg/ml propylparaben added as preservatives. | 5 ml |

TABLE B

Examples of Dexamethasone Sodium Phosphate formulations including excipient profile (U.S.)

| Product NDC (USA) | Proprietary Name | Dosage Form Name | Route Name | Application Number | Labeler Name |
|---|---|---|---|---|---|
| 64679-810 | Baycadron | ELIXIR | ORAL | ANDA088254 | Wockhardt USA, LLC |
| 58463-010 | Decadron | ELIXIR | ORAL | ANDA090891 | Pragma Pharmaceuticals, LLC |
| 58463-014 | Decadron | TABLET | ORAL | ANDA088481 | Pragma Pharmaceuticals, LLC |
| 58463-015 | Decadron | TABLET | ORAL | ANDA088481 | Pragma Pharmaceuticals, LLC |
| 58463-016 | Decadron | TABLET | ORAL | ANDA088481 | Pragma Pharmaceuticals, LLC |
| 58463-017 | Decadron | TABLET | ORAL | ANDA088481 | Pragma Pharmaceuticals, LLC |

TABLE B-continued

| Examples of Dexamethasone Sodium Phosphate formulations including excipient profile (U.S.) | | | | | |
|---|---|---|---|---|---|
| 0054-4179 | Dexamethasone | TABLET | ORAL | ANDA084611 | West-Ward Pharmaceuticals Corp. |
| 0054-4180 | Dexamethasone | TABLET | ORAL | ANDA084613 | West-Ward Pharmaceuticals Corp. |
| 0054-4181 | Dexamethasone | TABLET | ORAL | ANDA088306 | West-Ward Pharmaceuticals Corp. |
| 0054-4182 | Dexamethasone | TABLET | ORAL | ANDA084610 | West-Ward Pharmaceuticals Corp. |
| 0054-4183 | Dexamethasone | TABLET | ORAL | ANDA087916 | West-Ward Pharmaceuticals Corp. |
| 0054-4184 | Dexamethasone | TABLET | ORAL | ANDA084612 | West-Ward Pharmaceuticals Corp. |
| 0054-4186 | Dexamethasone | TABLET | ORAL | ANDA088316 | West-Ward Pharmaceuticals Corp. |
| 0054-8174 | Dexamethasone | TABLET | ORAL | ANDA088306 | West-Ward Pharmaceuticals Corp. |
| 0054-8175 | Dexamethasone | TABLET | ORAL | ANDA084612 | West-Ward Pharmaceuticals Corp. |
| 0054-8176 | Dexamethasone | TABLET | ORAL | ANDA087916 | West-Ward Pharmaceuticals Corp. |
| 0054-8179 | Dexamethasone | TABLET | ORAL | ANDA084611 | West-Ward Pharmaceuticals Corp. |
| 0054-8180 | Dexamethasone | TABLET | ORAL | ANDA084613 | West-Ward Pharmaceuticals Corp. |
| 0054-8181 | Dexamethasone | TABLET | ORAL | ANDA084610 | West-Ward Pharmaceuticals Corp. |
| 0054-8183 | Dexamethasone | TABLET | ORAL | ANDA088316 | West-Ward Pharmaceuticals Corp. |
| 0095-0087 | Dexamethasone | TABLET | ORAL | ANDA040700 | ECR Pharmaceuticals |
| 0095-0088 | Dexamethasone | TABLET | ORAL | ANDA040700 | ECR Pharmaceuticals |
| 0095-0089 | Dexamethasone | TABLET | ORAL | ANDA040700 | ECR Pharmaceuticals |
| 10544-211 | Dexamethasone | TABLET | ORAL | ANDA088237 | Blenheim Pharmacal, Inc. |
| 10544-212 | Dexamethasone | TABLET | ORAL | ANDA088238 | Blenheim Pharmacal, Inc. |
| 21695-290 | Dexamethasone | TABLET | ORAL | ANDA084613 | Rebel Distributors Corp |
| 21695-382 | Dexamethasone | TABLET | ORAL | ANDA084612 | Rebel Distributors Corp |
| 21695-728 | Dexamethasone | TABLET | ORAL | ANDA088306 | Rebel Distributors Corp |
| 21695-745 | Dexamethasone | TABLET | ORAL | ANDA087916 | Rebel Distributors Corp |
| 24236-550 | Dexamethasone | TABLET | ORAL | ANDA084612 | REMEDYREPACK INC. |
| 33261-625 | Dexamethasone | TABLET | ORAL | ANDA088238 | Aidarex Pharmaceuticals LLC |
| 42195-015 | Dexamethasone | TABLET | ORAL | ANDA088237 | Xspire Pharma, LLC |
| 43063-266 | Dexamethasone | TABLET | ORAL | ANDA087916 | PD-Rx Pharmaceuticals, Inc. |

TABLE B-continued

| Examples of Dexamethasone Sodium Phosphate formulations including excipient profile (U.S.) | | | | | |
|---|---|---|---|---|---|
| 48102-045 | Dexamethasone | TABLET | ORAL | ANDA088481 | Fera Pharmaceuticals, LLC |
| 48102-046 | Dexamethasone | TABLET | ORAL | ANDA088481 | Fera Pharmaceuticals, LLC |
| 48102-047 | Dexamethasone | TABLET | ORAL | ANDA088481 | Fera Pharmaceuticals, LLC |
| 48102-048 | Dexamethasone | TABLET | ORAL | ANDA088481 | Fera Pharmaceuticals, LLC |
| 49884-084 | Dexamethasone | TABLET | ORAL | ANDA088148 | Par Pharmaceutical Inc. |
| 49884-085 | Dexamethasone | TABLET | ORAL | ANDA088160 | Par Pharmaceutical Inc. |
| 49884-086 | Dexamethasone | TABLET | ORAL | ANDA088237 | Par Pharmaceutical Inc. |
| 49884-087 | Dexamethasone | TABLET | ORAL | ANDA088238 | Par Pharmaceutical Inc. |
| 49884-373 | Dexamethasone | TABLET | ORAL | ANDA088481 | Par Pharmaceutical Inc. |
| 49999-059 | Dexamethasone | TABLET | ORAL | ANDA084612 | Lake Erie Medical DBA Quality Care Products LLC |
| 50090-0088 | Dexamethasone | TABLET | ORAL | ANDA084612 | A-S Medication Solutions |
| 50090-0089 | Dexamethasone | TABLET | ORAL | ANDA084612 | A-S Medication Solutions |
| 52959-547 | Dexamethasone | TABLET | ORAL | ANDA088238 | H.J. Harkins Company, Inc. |
| 53217-231 | Dexamethasone | TABLET | ORAL | ANDA084613 | Aidarex Pharmaceuticals LLC |
| 53217-310 | Dexamethasone | ELIXIR | ORAL | ANDA084754 | Aidarex Pharmaceuticals LLC |
| 54868-0218 | Dexamethasone | TABLET | ORAL | ANDA084612 | Physicians Total Care, Inc |
| 54868-0916 | Dexamethasone | TABLET | ORAL | ANDA084613 | Physicians Total Care, Inc |
| 54868-0927 | Dexamethasone | TABLET | ORAL | ANDA084611 | Physicians Total Care, Inc |
| 54868-1744 | Dexamethasone | TABLET | ORAL | ANDA084610 | Physicians Total Care, Inc |
| 54868-3157 | Dexamethasone | TABLET | ORAL | ANDA087916 | Physicians Total Care, Inc |
| 54868-5334 | Dexamethasone | TABLET | ORAL | ANDA040700 | Physicians Total Care, Inc. |
| 54868-5903 | Dexamethasone | TABLET | ORAL | ANDA088316 | Physicians Total Care, Inc |
| 54879-003 | Dexamethasone | ELIXIR | ORAL | ANDA084754 | STI Pharma LLC |
| 55154-4901 | Dexamethasone | TABLET | ORAL | ANDA084612 | Cardinal Health |
| 55154-4914 | Dexamethasone | TABLET | ORAL | ANDA087916 | Cardinal Health |
| 55289-582 | Dexamethasone | TABLET | ORAL | ANDA084612 | PD-Rx Pharmaceuticals, Inc. |

TABLE B-continued

Examples of Dexamethasone Sodium Phosphate formulations including excipient profile (U.S.)

| | | | | | |
|---|---|---|---|---|---|
| 55289-903 | Dexamethasone | TABLET | ORAL | ANDA084613 | PD-Rx Pharmaceuticals, Inc. |
| 60432-466 | Dexamethasone | ELIXIR | ORAL | ANDA088254 | Morton Grove Pharmaceuticals, Inc. |
| 61919-269 | Dexamethasone | TABLET | ORAL | ANDA088237 | Direct Rx |
| 63187-383 | Dexamethasone | TABLET | ORAL | ANDA087916 | Proficient Rx LP |
| 63187-561 | Dexamethasone | TABLET | ORAL | ANDA084612 | Proficient Rx LP |
| 63629-3742 | Dexamethasone | TABLET | ORAL | ANDA084612 | Bryant Ranch Prepack |
| 63629-4129 | Dexamethasone | TABLET | ORAL | ANDA084613 | Bryant Ranch Prepack |
| 64980-509 | Dexamethasone | ELIXIR | ORAL | ANDA090891 | Rising Pharmaceuticals, Inc. |
| 66267-067 | Dexamethasone | TABLET | ORAL | ANDA088238 | NuCare Pharmaceuticals, Inc. |
| 66336-479 | Dexamethasone | TABLET | ORAL | ANDA084612 | Dispensing Solutions, Inc. |
| 67296-0326 | Dexamethasone | TABLET | ORAL | ANDA084612 | RedPharm Drug |
| 67296-1090 | Dexamethasone | TABLET | ORAL | ANDA088238 | RedPharm Drug, Inc. |
| 68047-702 | Dexamethasone | TABLET | ORAL | ANDA201270 | Larken Laboratories, Inc. |
| 68071-4127 | Dexamethasone | TABLET | ORAL | ANDA088238 | NuCare Pharmaceuticals, Inc. |
| 68788-7142 | Dexamethasone | TABLET | ORAL | ANDA084612 | Preferred Pharmaceuticals Inc. |
| 68788-9938 | Dexamethasone | TABLET | ORAL | ANDA088238 | Preferred Pharmaceuticals, Inc. |
| 68788-9939 | Dexamethasone | TABLET | ORAL | ANDA088160 | Preferred Pharmaceuticals, Inc. |
| 69189-4186 | Dexamethasone | TABLET | ORAL | ANDA088316 | Avera McKennan Hospital |
| 70518-0843 | Dexamethasone | TABLET | ORAL | ANDA088238 | REMEDYREPACK INC. |
| 71335-0077 | Dexamethasone | TABLET | ORAL | ANDA088160 | Bryant Ranch Prepack |
| 71335-0177 | Dexamethasone | TABLET | ORAL | ANDA088238 | Bryant Ranch Prepack |
| 0054-3176 | Dexamethasone Intensol | SOLUTION, CONCENTRATE | ORAL | ANDA088252 | West-Ward Pharmaceuticals Corp. |
| 68151-5026 | Dexamethasone Intensol | SOLUTION, CONCENTRATE | ORAL | ANDA088252 | Carilion Materials Management |
| 0641-0367 | Dexamethasone Sodium Phosphate | INJECTION | INTRAMUSCULAR; INTRAVENOUS | ANDA087702 | West-Ward Pharmaceuticals Corp. |
| 0641-6145 | Dexamethasone Sodium Phosphate | INJECTION | INTRA-ARTICULAR; INTRALESIONAL; INTRAMUSCULAR; INTRAVENOUS; SOFT TISSUE | ANDA084282 | West-Ward Pharmaceuticals Corp. |
| 0641-6146 | Dexamethasone Sodium Phosphate | INJECTION | INTRA-ARTICULAR; INTRALESIONAL; INTRAMUSCULAR; INTRAVENOUS; SOFT TISSUE | ANDA084282 | West-Ward Pharmaceuticals Corp. |

TABLE B-continued

| Examples of Dexamethasone Sodium Phosphate formulations including excipient profile (U.S.) | | | | | |
|---|---|---|---|---|---|
| 0904-3006 | Dexamethasone Sodium Phosphate | SOLUTION/ DROPS | OPHTHALMIC | ANDA040069 | Major Pharmaceuticals |
| 11695-1411 | Dexamethasone Sodium Phosphate | SOLUTION/ DROPS | OPHTHALMIC | ANDA040069 | Butler Animal Health Supply |
| 21695-847 | Dexamethasone Sodium Phosphate | SOLUTION | OPHTHALMIC | ANDA088771 | Rebel Distributors Corp |
| 24208-720 | Dexamethasone Sodium Phosphate | SOLUTION/ DROPS | OPHTHALMIC | ANDA040069 | Bausch & Lomb Incorporated |
| 42254-088 | Dexamethasone Sodium Phosphate | SOLUTION/ DROPS | OPHTHALMIC | ANDA040069 | Rebel Distributors Corp |
| 52584-420 | Dexamethasone Sodium Phosphate | INJECTION, SOLUTION | INTRAMUSCULAR; INTRAVENOUS | ANDA040802 | General Injectables and Vaccines, Inc. |
| 52584-421 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | General Injectables and Vaccines, Inc |
| 52584-422 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | General Injectables and Vaccines, Inc |
| 54868-3129 | Dexamethasone Sodium Phosphate | SOLUTION | OPHTHALMIC | ANDA088771 | Physicians Total Care, Inc. |
| 54868-6099 | DEXAMETHASONE Sodium Phosphate | INJECTION | INTRAMUSCULAR; INTRAVENOUS | ANDA081126 | Physicians Total Care, Inc. |
| 55045-1755 | Dexamethasone Sodium Phosphate | SOLUTION | OPHTHALMIC | ANDA088771 | Dispensing Solutions, Inc. |
| 55150-237 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | AuroMedics Pharma LLC |
| 55150-238 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | AuroMedics Pharma LLC |
| 55150-239 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | AuroMedics Pharma LLC |
| 55154-5118 | Dexamethasone Sodium Phosphate | INJECTION | INTRAMUSCULAR; INTRAVENOUS | ANDA087702 | Cardinal Health |
| 55154-7075 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | Cardinal Health |
| 55154-9364 | Dexamethasone Sodium Phosphate | INJECTION, SOLUTION | INTRAMUSCULAR; INTRAVENOUS | ANDA084916 | Cardinal Health |
| 55154-9371 | Dexamethasone Sodium Phosphate | INJECTION, SOLUTION | INTRAMUSCULAR; INTRAVENOUS | ANDA040491 | Cardinal Health |
| 57319-065 | Dexamethasone Sodium Phosphate | SOLUTION/ DROPS | OPHTHALMIC | ANDA040069 | Phoenix Pharmaceutical, Inc. |

TABLE B-continued

| Examples of Dexamethasone Sodium Phosphate formulations including excipient profile (U.S.) | | | | | |
|---|---|---|---|---|---|
| 61314-294 | Dexamethasone Sodium Phosphate | SOLUTION | OPHTHALMIC | ANDA088771 | Sandoz Inc |
| 61786-979 | Dexamethasone Sodium Phosphate | INJECTION, SOLUTION | INTRAMUSCULAR; INTRAVENOUS | ANDA084916 | REMEDYREPACK INC. |
| 63323-165 | Dexamethasone Sodium Phosphate | INJECTION, SOLUTION | INTRAMUSCULAR; INTRAVENOUS | ANDA084916 | Fresenius Kabi USA, LLC |
| 63323-165 | Dexamethasone Sodium Phosphate | INJECTION, SOLUTION | INTRAMUSCULAR; INTRAVENOUS | ANDA084916 | Fresenius Kabi USA, LLC |
| 63323-506 | Dexamethasone Sodium Phosphate | INJECTION, SOLUTION | INTRAMUSCULAR; INTRAVENOUS | ANDA040491 | Fresenius Kabi USA, LLC |
| 63323-506 | Dexamethasone Sodium Phosphate | INJECTION, SOLUTION | INTRAMUSCULAR; INTRAVENOUS | ANDA040491 | Fresenius Kabi USA, LLC |
| 63323-516 | Dexamethasone Sodium Phosphate | INJECTION, SOLUTION | INTRAMUSCULAR; INTRAVENOUS | ANDA040572 | Fresenius Kabi USA, LLC |
| 67457-420 | Dexamethasone Sodium Phosphate | INJECTION, SOLUTION | INTRAMUSCULAR; INTRAVENOUS | ANDA040802 | Mylan Institutional LLC |
| 67457-421 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | Mylan Institutional LLC |
| 67457-422 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | Mylan Institutional LLC |
| 67457-423 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA040803 | Mylan Institutional LLC |
| 68071-1866 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | NuCare Pharmaceuticals, Inc. |
| 70069-021 | Dexamethasone Sodium Phosphate | INJECTION | INTRAMUSCULAR; INTRAVENOUS | ANDA207442 | Somerset Therapeutics, LLC |
| 70518-0410 | Dexamethasone Sodium Phosphate | SOLUTION/ DROPS | OPHTHALMIC | ANDA040069 | REMEDYREPACK INC. |
| 70518-0532 | Dexamethasone Sodium Phosphate | INJECTION | INTRAMUSCULAR; INTRAVENOUS | ANDA087702 | REMEDYREPACK INC. |
| 70518-0621 | Dexamethasone Sodium Phosphate | INJECTION, SOLUTION | INTRAMUSCULAR; INTRAVENOUS | ANDA084916 | REMEDYREPACK INC. |
| 70518-0872 | Dexamethasone Sodium Phosphate | INJECTION, SOLUTION | INTRAMUSCULAR; INTRAVENOUS | ANDA084916 | REMEDYREPACK INC. |
| 71872-7021 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | Medical Purchasing Solutions, LLC |
| 71872-7090 | Dexamethasone Sodium Phosphate | INJECTION, SOLUTION | INTRAMUSCULAR; INTRAVENOUS | ANDA040802 | Medical Purchasing Solutions, LLC |
| 71872-7091 | Dexamethasone Sodium Phosphate | INJECTION | INTRAMUSCULAR; INTRAVENOUS | ANDA087702 | Medical Purchasing Solutions, LLC |

TABLE B-continued

Examples of Dexamethasone Sodium Phosphate formulations including excipient profile (U.S.)

| | | | | | |
|---|---|---|---|---|---|
| 71872-7092 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | Medical Purchasing Solutions, LLC |
| 71872-7128 | DEXAMETHASONE SODIUM PHOSPHATE | INJECTION, SOLUTION | INTRA-ARTICULAR; INTRALESIONAL; INTRAMUSCULAR; INTRAVENOUS; SOFT TISSUE | ANDA206781 | Medical Purchasing Solutions, LLC |
| 76045-106 | Dexamethasone Sodium Phosphate | INJECTION, SOLUTION | INTRA-ARTICULAR; INTRALESIONAL; INTRAMUSCULAR; INTRAVENOUS; SOFT TISSUE | ANDA203129 | Fresenius Kabi USA, LLC |
| 51655-012 | Dexamethsone | TABLET | ORAL | ANDA084612 | Northwind Pharmaceuticals, LLC |
| 71879-001 | Dexycu | INJECTION, SUSPENSION | INTRAOCULAR | NDA208912 | EyePoint Pharmaceuticals US, Inc |
| 76420-270 | DMT SUIK | INJECTION, SOLUTION | INTRAMUSCULAR; INTRAVENOUS | | Asclemed USA, Inc. |
| 0998-0615 | Maxidex | SUSPENSION | OPHTHALMIC | NDA013422 | Alcon Laboratories, Inc. |
| 71205-013 | TaperDex 12-day | TABLET | ORAL | ANDA088237 | Proficient Rx LP |
| 71205-012 | TaperDex 6-day | TABLET | ORAL | ANDA088237 | Proficient Rx LP |
| 69677-071 | MAS CARE-PAK DEXAMETHASONE | KIT | INTRAMUSCULAR; INTRAVENOUS; TOPICAL | ANDA040491 | MAS Management Group Inc. |
| 70529-112 | Neuromaquel Neuroma/Anti-Inflammatory System | KIT | INTRA-ARTICULAR; INTRALESIONAL; INTRAMUSCULAR; INTRAVENOUS; SOFT TISSUE | ANDA084916 | IT3 Medical LLC |
| 53225-3660 | ReadySharp Dexamethasone | INJECTION | INTRAMUSCULAR; INTRAVENOUS | ANDA087702 | Terrain Pharmaceuticals |
| 76420-810 | Mardex 25 Kit | KIT | EPIDURAL; INFILTRATION; INTRAMUSCULAR; INTRAVENOUS; TOPICAL | | Asclemed USA, Inc. |
| 70112-555 | TopiDex | KIT | INTRAMUSCULAR; INTRAVENOUS | ANDA040491 | Topicare Management, LLC |
| withdrawn 0006-7646-03 | DECADRON Phosphate injection | INJECTION, SOLUTION | INTRAVENOUS | | Merck |

| Product NDC (USA) | Strength | Unit | Excipients |
|---|---|---|---|
| 64679-810 | 0.5 | mg/5 mL | Benzoic Acid, USP (as preservative) (0.1%); Alcohol (5.1%), raw sugar (UNII: 8M707QY5GH), propylene glycol (UNII: 6DC9Q167V3), benzoic acid (UNII: 8SKN0B0MIM), alcohol (UNII: 3K9958V90M), Anhydrous Citric Acid (UNII: XF417D3PSL), FD&C red no. 40 (UNII: WZB9127XOA), water (UNII: 059QF0KO0R), sodium citrate (UNII: 1Q73Q2JULR), citric acid monohydrate (UNII: 2968PHW8QP) |
| 58463-010 | 0.5 | mg/5 mL | Benzoic Acid, USP (as preservative) (0.1%); Alcohol (% v/v) (5.1%), alcohol (UNII: 3K9958V90M), benzoic acid (UNII: 8SKN0B0MIM), citric acid monohydrate (UNII: 2968PHW8QP), FD&C red no. 40 (UNII: WZB9127XOA), propylene glycol (UNII: 6DC9Q167V3), raspberry (UNII: 4N14V5R27W), |

TABLE B-continued

| Examples of Dexamethasone Sodium Phosphate formulations including excipient profile (U.S.) | | | |
|---|---|---|---|
| | | | sucrose (UNII: C151H8M554), trisodium citrate di hydrate (UNII: B22547B95K), water (UNII: 059QF0KO0R) |
| 58463-014 | 0.5 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP); D&C Yellow No. 10 (UNII: 35SW5USQ3G); FD&C Yellow No. 5 (UNII: 1753WB2F1M) |
| 58463-015 | 0.75 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP); D&C Yellow No. 10 (UNII: 35SW5USQ3G); FD&C Blue No. 1 (UNII: H3R473TBD) |
| 58463-016 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 58463-017 | 6 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 0054-4179 | 0.5 | mg/1 | D&C Yellow No. 10 (0.5 mg and 4 mg) (UNII: 35SW5USQ3G); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-4180 | 0.75 | mg/1 | FD&C Blue No. 1 (0.75 mg and 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-4181 | 1 | mg/1 | Ferric Oxide Yellow (1 mg) (UNII: EX438O2MRT); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-4182 | 1.5 | mg/1 | FD&C Blue No. 1 (0.75 mg and 1.5 mg) (UNII: H3R47K3TBD); FD&C Red No. 3 (1.5 mg) (UNII: PN2ZH5LOQY); FD&C Red No. 40 (1.5 mg) (UNII: WZB9127XOA); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-4183 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-4184 | 4 | mg/1 | D&C Yellow No. 10 (0.5 mg and 4 mg) (UNII: 35SW5USQ3G); FD&C Yellow No. 6 (0.5 mg and 4 mg) (UNII: H77VE193A8); FD&C Green No. 3 (4 mg and 6 mg) (UNII: 3P3ONR6O1S); Lactose Monohydrate (UNII: EWQ57Q815X); Magnesium Stearate (UNII: 70097M6130); Starch, Corn (UNII: |

TABLE B-continued

| Examples of Dexamethasone Sodium Phosphate formulations including excipient profile (U.S.) | | | |
|---|---|---|---|
| | | | 0823NY3SJ); Sucrose (UNII: C151H8M554) |
| 0054-4186 | 6 | mg/1 | FD&C Green No. 3 (4 mg and 6 mg) (UNII: 3P3ONR6O1S); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8174 | 1 | mg/1 | Ferric Oxide Yellow (1 mg) (UNII: EX438O2MRT); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8175 | 4 | mg/1 | D&C Yellow No. 10 (0.5 mg and 4 mg) (UNII: 35SW5USQ3G); FD&C Yellow No. 6 (0.5 mg and 4 mg) (UNII: H77VE193A8); FD&C Green No. 3 (4 mg and 6 mg) (UNII: 3P3ONR6O1S); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8176 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8179 | 0.5 | mg/1 | D&C Yellow No. 10 (0.5 mg and 4 mg) (UNII: 35SW5USQ3G); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8180 | 0.75 | mg/1 | FD&C Blue No. 1 (0.75 mg and 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8181 | 1.5 | mg/1 | FD&C Blue No. 1 (0.75 mg and 1.5 mg) (UNII: H3R47K3TBD); FD&C Red No. 3 (1.5 mg) (UNII: PN2ZH5LOQY); FD&C Red No. 40 (1.5 mg) (UNII: WZB9127XOA); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0054-8183 | 6 | mg/1 | FD&C Green No. 3 (4 mg and 6 mg) (UNII: 3P3ONR6O1S); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 0095-0087 | 1.5 | mg/1 | microcrystalline cellulose (UNII: OP1R32D61U); anhydrous lactose (UNII: 3SY5LH9PMK); croscarmellose sodium (UNII: M28OL1HH48); magnesium stearate (UNII: 70097M6130); FD&C Red No. 40 aluminum lake |
| 0095-0088 | 1.5 | mg/1 | microcrystalline cellulose (UNII: OP1R32D61U); anhydrous lactose (UNII: 3SY5LH9PMK); croscarmellose sodium (UNII: M28OL1HH48); magnesium stearate (UNII: 70097M6130); FD&C Red No. 40 aluminum lake |
| 0095-0089 | 1.5 | mg/1 | microcrystalline cellulose (UNII: OP1R32D61U); anhydrous lactose (UNII: 3SY5LH9PMK); croscarmellose |

TABLE B-continued

| Examples of Dexamethasone Sodium Phosphate formulations including excipient profile (U.S.) | | | |
|---|---|---|---|
| | | | sodium (UNII: M28OL1HH48); magnesium stearate (UNII: 70097M6130); FD&C Red No. 40 aluminum lake |
| 10544-211 | 1.5 | mg/1 | FD&C Red No. 40 (UNII: WZB9127XOA); Magnesium Stearate (UNII: 70097M6130); microcrystalline cellulose (UNII: OP1R32D61U); anhydrous lactose (UNII: 3SY5LH9PMK); croscarmellose sodium (UNII: M28OL1HH48); Stearic Acid (UNII: 4ELV7Z65AP) |
| 10544-212 | 4 | mg/1 | Magnesium Stearate (UNII: 70097M6130); microcrystalline cellulose (UNII: OP1R32D61U); anhydrous lactose (UNII: 3SY5LH9PMK); croscarmellose sodium (UNII: M28OL1HH48); Stearic Acid (UNII: 4ELV7Z65AP) |
| 21695-290 | 0.75 | mg/1 | FD&C Blue No. 1 (0.75, 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 21695-382 | 4 | mg/1 | D&C Yellow No. 10 (0.5, 4 mg) (UNII: 35SW5USQ3G); FD&C Green No. 3 (4, 6 mg) (UNII: 3P3ONR6O1S); FD&C Yellow No. 6 (0.5, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 21695-728 | 1 | mg/1 | Ferric Oxide Yellow (1 mg) (UNII: EX438O2MRT); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 21695-745 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 24236-550 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 33261-625 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 42195-015 | 1.5 | mg/1 | FD&C Red No. 40 (UNII: WZB9127XOA); Magnesium Stearate (UNII: 70097M6130); microcrystalline cellulose (UNII: OP1R32D61U); anhydrous lactose (UNII: 3SY5LH9PMK); croscarmellose sodium (UNII: M28OL1HH48); Stearic Acid (UNII: 4ELV7Z65AP) |
| 43063-266 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 48102-045 | 0.5 | mg/1 | D&C Yellow No. 10 (UNII: 35SW5USQ3G); FD&C Yellow No. 5 (UNII: 1753WB2F1M) anhydrous lactose |

TABLE B-continued

| Examples of Dexamethasone Sodium Phosphate formulations including excipient profile (U.S.) | | | |
|---|---|---|---|
| | | | (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 48102-046 | 0.75 | mg/1 | D&C Yellow No. 10 (UNII: 35SW5USQ3G); FD&C Blue No. 1 (UNII: H3R47K3TBD) anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 48102-047 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 48102-048 | 6 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49884-084 | 0.5 | mg/1 | D&C Yellow No. 10 (UNII: 35SW5USQ3G); FD&C Yellow No. 5 (UNII: 1753WB2F1M) anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49884-085 | 0.75 | mg/1 | D&C Yellow No. 10 (UNII: 35SW5USQ3G); FD&C Blue No. 1 (UNII: H3R47K3TBD) anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49884-086 | 1.5 | mg/1 | FD&C Red No. 40 (UNII: WZB9127XOA); anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49884-087 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49884-373 | 6 | mg/1 | D&C Yellow No. 10 (UNII: 35SW5USQ3G); FD&C Blue No. 1 (UNII: H3R47K3TBD); FD&C Yellow No. 6 (UNII: H77VE193A8); anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 49999-059 | 4 | mg/1 | D&C Yellow No. 10 (0.5, 4 mg) (UNII: 35SW5USQ3G); FD&C Green No. 3 (4, 6 mg) (UNII: 3P3ONR6O1S); FD&C Yellow No. 6 (0.5, 4 mg) (UNII: H77VE193A8); Lactose Monohydrate (UNII: EWQ57Q815X); Magnesium |

TABLE B-continued

| Examples of Dexamethasone Sodium Phosphate formulations including excipient profile (U.S.) | | | |
|---|---|---|---|
| | | | Stearate (UNII: 70097M6130); Starch, Corn (UNII: 0823NY3SJ); Sucrose (UNII: C151H8M554) |
| 50090-0088 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 50090-0089 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 52959-547 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 53217-231 | 0.75 | mg/1 | FD&C Blue No. 1 (0.75 mg and 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 53217-310 | 0.5 | mg/5 mL | Benzoic Acid, USP (as preservative) (0.1%); Alcohol (5%) |
| 54868-0218 | 4 | mg/1 | D&C Yellow No. 10 (0.5, 4 mg) (UNII: 35SW5USQ3G); FD&C Green No. 3 (4, 6 mg) (UNII: 3P3ONR6O1S); FD&C Yellow No. 6 (0.5, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54868-0916 | 0.75 | mg/1 | FD&C Blue No. 1 (0.75, 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54868-0927 | 0.5 | mg/1 | D&C Yellow No. 10 (0.5, 4 mg) (UNII: 35SW5USQ3G); FD&C Yellow No. 6 (0.5, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54868-1744 | 1.5 | mg/1 | FD&C Blue No. 1 (0.75, 1.5 mg) (UNII: H3R47K3TBD); FD&C Red No. 3 (1.5 mg) (UNII: PN2ZH5LOQY); FD&C Red No. 40 (1.5 mg) (UNII: WZB9127XOA); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54868-3157 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54868-5334 | 1.5 | mg/1 | anhydrous lactose (UNII: 3SY5LH9PMK); croscarmellose sodium |

TABLE B-continued

| Examples of Dexamethasone Sodium Phosphate formulations including excipient profile (U.S.) | | | |
|---|---|---|---|
| | | | (UNII: M28OL1HH48); magnesium stearate (UNII: 70097M6130); microcrystalline cellulose (UNII: OP1R32D61U); FD&C Red No. 40 |
| 54868-5903 | 6 | mg/1 | FD&C Green No. 3 (4, 6 mg) (UNII: 3P3ONR6O1S); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 54879-003 | 0.5 | mg/5 mL | Benzoic Acid, USP (as preservative) (0.1%); Alcohol (5%) |
| 55154-4901 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 55154-4914 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 55289-582 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 55289-903 | 0.75 | mg/1 | FD&C Blue No. 1 (0.75 mg and 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 60432-466 | 0.5 | mg/5 mL | Benzoic Acid, USP (as preservative) (0.1%); Alcohol (5.1%) |
| 61919-269 | 1.5 | mg/1 | FD&C Red No. 40 (UNII: WZB9127XOA); anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 63187-383 | 2 | mg/1 | Lactose Monohydrate (UNII: EWQ57Q815X); Magnesium Stearate (UNII: 70097M6130); Starch, Corn (UNII: 0823NY3SJ); Sucrose (UNII: C151H8M554) |
| 63187-561 | 4 | mg/1 | D&C Yellow No. 10 (0.5 mg, 4 mg) (UNII: 35SW5USQ3G); FD&C Green No. 3 (4 mg, 6 mg) (UNII: 3P3ONR6O1S); FD&C Yellow No. 6 (0.5 mg, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 63629-3742 | 4 | mg/1 | D&C Yellow No. 10 (0.5, 4 mg) (UNII: 35SW5USQ3G); FD&C Green No. 3 (4, 6 mg) (UNII: 3P3ONR6O1S); FD&C Yellow No. 6 (0.5, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |

TABLE B-continued

| Examples of Dexamethasone Sodium Phosphate formulations including excipient profile (U.S.) | | | |
|---|---|---|---|
| 63629-4129 | 0.75 | mg/1 | FD&C Blue No. 1 (0.75 mg and 1.5 mg) (UNII: H3R47K3TBD); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 64980-509 | 0.5 | mg/5 mL | Benzoic Acid, USP (as preservative) (0.1%); Alcohol (% v/v) (5%) |
| 66267-067 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 66336-479 | 4 | mg/1 | D&C Yellow No. 10 (0.5, 4 mg) (UNII: 35SW5USQ3G); FD&C Green No. 3 (4, 6 mg) (UNII: 3P3ONR6O1S); FD&C Yellow No. 6 (0.5, 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 67296-0326 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 67296-1090 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 68047-702 | 1.5 | mg/1 | Lactose Monohydrate (UNII: EWQ57Q815X); Magnesium Stearate (UNII: 70097M6130); Maltodextrin (UNII: 7CVR7L4A2D); Starch, Corn (UNII: 0823NY3SJ); Sucrose (UNII: C151H8M554) |
| 68071-4127 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 68788-7142 | 4 | mg/1 | D&C Yellow No. 10 (0.5 mg and 4 mg) (UNII: 35SW5USQ3G); FD&C Green No. 3 (4 mg and 6 mg) (UNII: 3P3ONR6O1S); FD&C Yellow No. 6 (0.5 mg and 4 mg) (UNII: H77VE193A8); Lactose Monohydrate (UNII: EWQ57Q815X); Magnesium Stearate (UNII: 70097M6130); Starch, Corn (UNII: 0823NY3SJ); Sucrose (UNII: C151H8M554) |
| 68788-9938 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 68788-9939 | 0.75 | mg/1 | D&C Yellow No. 10 (UNII: 35SW5USQ3G); FD&C Blue No. 1 (UNII: H3R47K3TBD) anhydrous lactose (UNII: 3SY5LH9PMK); croscarmellose sodium (UNII: M28OL1HH48); magnesium stearate |

TABLE B-continued

| Examples of Dexamethasone Sodium Phosphate formulations including excipient profile (U.S.) | | | |
|---|---|---|---|
| | | | (UNII: 70097M6130); microcrystalline cellulose (UNII: OP1R32D61U); stearic acid (UNII: 4ELV7Z65AP) |
| 69189-4186 | 6 | mg/1 | |
| 70518-0843 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 71335-0077 | 0.75 | mg/1 | D&C Yellow No. 10 (UNII: 35SW5USQ3G); FD&C Blue No. 1 (UNII: H3R47K3TBD) anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 71335-0177 | 4 | mg/1 | anhydrous lactose (UNII: 3SY5LH9PMK); croscarmellose sodium (UNII: M28OL1HH48); magnesium stearate (UNII: 70097M6130); microcrystalline cellulose (UNII: OP1R32D61U); stearic acid (UNII: 4ELV7Z65AP) |
| 0054-3176 | 1 | mg/mL | Alcohol (UNII: 3K9 9 58V9 0M) Benzoic Acid (UNII: 8 SKN0B0MIM), Citric Acid MONOHYDRATE (UNII: 29 6 8 PHW8QP), Edetate Disodium (UNII: 7FLD9 1C8 6K), Propylene Glycol (UNII: 6DC9Q16 7V3), Water (UNII: 0 59QFOKO0R) |
| 68151-5026 | 1 | mg/mL | Alcohol (UNII: 3K9 9 58V9 0M); Benzoic Acid (UNII: 8 SKN0B0MIM); Citric Acid MONOHYDRATE (UNII: 29 6 8 PHW8QP); Edetate Disodium (UNII: 7FLD9 1C8 6K); Propylene Glycol (UNII: 6DC9Q16 7V3); Water (UNII: 0 59QF0KO0R) |
| 0641-0367 | 10 | mg/mL | Sodium Sulfite (1.5 mg in 1 mL) (UNII: VTK01UQK3G); Sodium Citrate (16.5 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 2968PHW8QP) |
| 0641-6145 | 4 | mg/mL | Sodium Sulfite (1 mg in 1 mL) (UNII: VTK01UQK3G); Sodium Citrate (19.4 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 2968PHW8QP) |
| 0641-6146 | 4 | mg/mL | Sodium Sulfite (1 mg in 1 mL) (UNII: VTK01UQK3G); Sodium Citrate (19.4 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 2968PHW8QP) |
| 0904-3006 | 1 | mg/mL | Benzalkonium Chloride (0.02%) (UNII: F5UM2KM3W7); Creatinine (UNII: 7FLD91C86K); Edetate Disodium (UNII: 7FLD9 1C8 6K); Hydrochloric Acid (UNII: ML9LGA7468); Phenethyl Alcohol (0.25%) (UNII: ML9LGA7468); Polysorbate 80 (UNII: 6OZP39ZG8H); Water (UNII: 0 59QF0KO0R); Sodium Bisulfite (0.1%) (UNII: TZX5469Z6I); Sodium Borate (UNII: 91MBZ8H3QO); Sodium Citrate (UNII: 1Q73Q2JULR) |
| 11695-1411 | 1 | mg/mL | Benzalkonium Chloride (0.02%) (UNII: F5UM2KM3W7); Creatinine (UNII: |

TABLE B-continued

| Examples of Dexamethasone Sodium Phosphate formulations including excipient profile (U.S.) | | | |
|---|---|---|---|
| | | | 7FLD91C86K); Edetate Disodium (UNII: 7FLD9 1C8 6K); Hydrochloric Acid (UNII: ML9LGA7468); Phenethyl Alcohol (0.25%) (UNII: ML9LGA7468); Polysorbate 80 (UNII: 6OZP39ZG8H); Water (UNII: 0 59QF0KO0R); Sodium Bisulfite (0.1%) (UNII: TZX5469Z6I); Sodium Borate (UNII: 91MBZ8H3QO); Sodium Citrate (UNII: 1Q73Q2JULR) |
| 21695-847 | 1 | mg/mL | Benzalkonium Chloride (0.01%) (UNII: F5UM2KM3W7); Sodium Phosphate, Monobasic (UNII: 3980JIH2SW); Sodium Chloride (UNII: 451W47IQ8X); Sodium Phosphate Dibasic (UNII: GR686LBA74); Edetate Disodium (UNII: 7FLD9 1C8 6K); Sodium Phosphate, Monobasic (UNII: 3980JIH2SW); Sodium Phosphate Dibasic (UNII: GR686LBA74); Water (UNII: 0 59QF0KO0R) |
| 24208-720 | 1 | mg/mL | Benzalkonium Chloride (0.02%) (UNII: F5UM2KM3W7); Creatinine (UNII: 7FLD91C86K); Edetate Disodium (UNII: 7FLD9 1C8 6K); Hydrochloric Acid (UNII: ML9LGA7468); Phenethyl Alcohol (0.25%) (UNII: ML9LGA7468); Polysorbate 80 (UNII: 6OZP39ZG8H); Water (UNII: 0 59QF0KO0R); Sodium Bisulfite (0.1%) (UNII: TZX5469Z6I); Sodium Borate (UNII: 91MBZ8H3QO); Sodium Citrate, Unspecified Form (UNII: 1Q73Q2JULR) |
| 42254-088 | 1 | mg/mL | Benzalkonium Chloride (0.02%) (UNII: F5UM2KM3W7); Creatinine (UNII: 7FLD91C86K); Edetate Disodium (UNII: 7FLD9 1C8 6K); Hydrochloric Acid (UNII: ML9LGA7468); Phenethyl Alcohol (0.25%) (UNII: ML9LGA7468); Polysorbate 80 (UNII: 6OZP39ZG8H); Water (UNII: 0 59QF0KO0R); Sodium Bisulfite (0.1%) (UNII: TZX5469Z6I); Sodium Borate (UNII: 91MBZ8H3QO); Sodium Citrate (UNII: 1Q73Q2JULR) |
| 52584-420 | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 52584-421 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 52584-422 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 54868-3129 | 1 | mg/mL | Benzalkonium Chloride (0.01%) (UNII: F5UM2KM3W7); Sodium Phosphate, Monobasic (UNII: 3980JIH2SW); Sodium Chloride (UNII: 451W47IQ8X); Sodium Phosphate Dibasic (UNII: |

TABLE B-continued

| Examples of Dexamethasone Sodium Phosphate formulations including excipient profile (U.S.) | | | |
|---|---|---|---|
| | | | GR686LBA74); Edetate Disodium (UNII: 7FLD9 1C8 6K); Water (UNII: 0 59QF0KO0R) |
| 54868-6099 | 10 | mg/mL | Anhydrous Trisodium Citrate (10 mg in 1 mL) (UNII: RS7A450LGA); Sodium Metabisulfite (1 mg in 1 mL) (UNII: 4VON5FNS3C); Benzyl Alcohol (10 mg in 1 mL) (UNII: LKG8494WBH); Water (UNII: 059QF0KO0R); Citric Acid Monohydrate (UNII: 2968PHW8QP) |
| 55045-1755 | 1 | mg/mL | Benzalkonium Chloride (0.01%) (UNII: F5UM2KM3W7); Sodium Phosphate, Monobasic (UNII: 3980JIH2SW); Sodium Chloride (UNII: 451W47IQ8X); Sodium Phosphate Dibasic (UNII: GR686LBA74); Edetate Disodium (UNII: 7FLD9 1C8 6K); Water (UNII: 0 59QF0KO0R) |
| 55150-237 | 4 | mg/mL | Anhydrous Trisodium Citrate (UNII: RS7A450LGA); Sodium Sulfite (1 mg in 1 mL) (UNII: VTK01UQK3G); Benzyl Alcohol (10 mg in 1 mL) (UNII: LKG8494WBH); Water (UNII: 059QF0KO0R); Anhydrous Citric Acid (UNII: XF417D3PSL); Sodium Hydroxide (UNII: 55X04QC321) |
| 55150-238 | 4 | mg/mL | Anhydrous Trisodium Citrate (UNII: RS7A450LGA); Sodium Sulfite (1 mg in 1 mL) (UNII: VTK01UQK3G); Benzyl Alcohol (10 mg in 1 mL) (UNII: LKG8494WBH); Water (UNII: 059QF0KO0R); Anhydrous Citric Acid (UNII: XF417D3PSL); Sodium Hydroxide (UNII: 55X04QC321) |
| 55150-239 | 4 | mg/mL | Anhydrous Trisodium Citrate (UNII: RS7A450LGA); Sodium Sulfite (1 mg in 1 mL) (UNII: VTK01UQK3G); Benzyl Alcohol (10 mg in 1 mL) (UNII: LKG8494WBH); Water (UNII: 059QF0KO0R); Anhydrous Citric Acid (UNII: XF417D3PSL); Sodium Hydroxide (UNII: 55X04QC321) |
| 55154-5118 | 10 | mg/mL | Sodium Sulfate Anhydrous (1.5 mg in 1 mL) (UNII: 36KCS0R750); Anhydrous Trisodium Citrate (16.5 mg in 1 mL) (UNII: RS7A450LGA); Benzyl Alcohol (10.42 mg in 1 mL) (UNII: LKG8494WBH); Water (UNII: 059QF0KO0R); Sodium Hydroxide (UNII: 55X04QC321); Citric Acid Monohydrate (UNII: 2968PHW8QP) |
| 55154-7075 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 55154-9364 | 4 | mg/mL | Sodium Citrate, Unspecified Form (11 mg in 1 mL) (UNII: 1Q73Q2JULR); Sodium Sulfite (1 mg in 1 mL) (UNII: VTK01UQK3G); Benzyl Alcohol (10 mg in 1 mL) (UNII: LKG8494WBH); Citric Acid Monohydrate (UNII: 2968PHW8QP); Sodium Hydroxide (UNII: 55X04QC321) |
| 55154-9371 | 10 | mg/mL | Sodium Citrate, Unspecified Form (24.75 mg in 1 mL) (UNII: 1Q73Q2JULR); Citric Acid Monohydrate (UNII: 2968PHW8QP); Sodium Hydroxide (UNII: 55X04QC321) |
| 57319-065 | 1 | mg/mL | Benzalkonium Chloride (0.02%) (UNII: F5UM2KM3W7); Creatinine (UNII: 7FLD91C86K); Edetate Disodium (UNII: 7FLD9 1C8 6K); Hydrochloric Acid |

TABLE B-continued

| Examples of Dexamethasone Sodium Phosphate formulations including excipient profile (U.S.) | | | |
|---|---|---|---|
| | | | (UNII: ML9LGA7468); Phenethyl Alcohol (0.25%) (UNII: ML9LGA7468); Polysorbate 80 (UNII: 6OZP39ZG8H); Water (UNII: 0 59QF0KO0R); Sodium Bisulfite (0.1%) (UNII: TZX5469Z6I); Sodium Borate (UNII: 91MBZ8H3QO); Sodium Citrate (UNII: 1Q73Q2JULR) |
| 61314-294 | 1 | mg/mL | Benzalkonium Chloride (0.01%) (UNII: F5UM2KM3W7); Sodium Phosphate, Monobasic (UNII: 3980JIH2SW); Sodium Chloride (UNII: 451W47IQ8X); Sodium Phosphate, Dibasic (UNII: GR686LBA74); Edetate Disodium (UNII: 7FLD9 1C8 6K); Water (UNII: 0 59QF0KO0R) |
| 61786-979 | 4 | mg/mL | Sodium Citrate (11 mg in 1 mL) (UNII: 1Q73Q2JULR); Sodium Sulfite (1 mg in 1 mL) (UNII: VTK01UQK3G); Benzyl Alcohol (10 mg in 1 mL) (UNII: LKG8494WBH); Sodium Hydroxide (UNII: 55X04QC321) Citric Acid Monohydrate (UNII: 2968PHW8QP) |
| 63323-165 | 4 | mg/mL | Sodium Citrate (11 mg in 1 mL) (UNII: 1Q73Q2JULR); Sodium Sulfite (1 mg in 1 mL) (UNII: VTK01UQK3G); Benzyl Alcohol (10 mg in 1 mL) (UNII: LKG8494WBH); Sodium Hydroxide (UNII: 55X04QC321) Citric Acid Monohydrate (UNII: 2968PHW8QP) |
| 63323-165 | 4 | mg/mL | Sodium Citrate (11 mg in 1 mL) (UNII: 1Q73Q2JULR); Sodium Sulfite (1 mg in 1 mL) (UNII: VTK01UQK3G); Benzyl Alcohol (10 mg in 1 mL) (UNII: LKG8494WBH); Sodium Hydroxide (UNII: 55X04QC321) Citric Acid Monohydrate (UNII: 2968PHW8QP) |
| 63323-506 | 10 | mg/mL | Sodium Citrate (24.75 mg in 1 mL) (UNII: 1Q73Q2JULR); Sodium Hydroxide (UNII: 55X04QC321) Citric Acid Monohydrate (UNII: 2968PHW8QP) |
| 63323-506 | 10 | mg/mL | Sodium Citrate (24.75 mg in 1 mL) (UNII: 1Q73Q2JULR); Sodium Hydroxide (UNII: 55X04QC321) Citric Acid Monohydrate (UNII: 2968PHW8QP) |
| 63323-516 | 10 | mg/mL | Sodium Citrate (13.5 mg in 1 mL) (UNII: 1Q73Q2JULR); Benzyl Alcohol (10 mg in 1 mL) (UNII: LKG8494WBH); Sodium Hydroxide (UNII: 55X04QC321) Citric Acid Monohydrate (UNII: 2968PHW8QP) |
| 67457-420 | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 67457-421 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 67457-422 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: |

TABLE B-continued

| Examples of Dexamethasone Sodium Phosphate formulations including excipient profile (U.S.) | | | |
|---|---|---|---|
| | | | RS7A450LGA); Water (UNII: 059QF0KO0R); Sodium Hydroxide (UNII: 55X04QC321) Citric Acid Monohydrate (UNII: 2968PHW8QP) |
| 67457-423 | 4 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: RS7A450LGA); Water (UNII: 059QF0KO0R); Sodium Hydroxide (UNII: 55X04QC321) Citric Acid Monohydrate (UNII: 2968PHW8QP) |
| 68071-1866 | 4 | mg/mL | Anhydrous Trisodium Citrate (UNII: RS7A450LGA); Sodium Sulfite (1 mg in 1 mL) (UNII: VTK01UQK3G); Benzyl Alcohol (10 mg in 1 mL) (UNII: LKG8494WBH); Water (UNII: 059QF0KO0R); Anhydrous Citric Acid (UNII: XF417D3PSL); Sodium Hydroxide (UNII: 55X04QC321) |
| 70069-021 | 10 | mg/mL | Trisodium Citrate Dihydrate (24.75 mg in 1 mL) (UNII: B22547B95K), Citric Acid Monohydrate (UNII: 2968PHW8QP), Sodium Hydroxide (UNII: 55X04QC32I), Water (UNII: 059QF0KO0R) |
| 70518-0410 | 1 | mg/mL | BENZALKONIUM CHLORIDE (UNII: F5UM2KM3W7), CREATININE (UNII: AYI8EX34EU), EDETATE DISODIUM (UNII: 7FLD91C86K), HYDROCHLORIC ACID (UNII: QTT17582CB), PHENYLETHYL ALCOHOL (UNII: ML9LGA7468), POLYSORBATE 80 (UNII: 6OZP39ZG8H), WATER (UNII: 059QF0KO0R), SODIUM BISULFITE (UNII: TZX5469Z6I), SODIUM BORATE (UNII: 91MBZ8H3QO), SODIUM CITRATE, UNSPECIFIED FORM (UNII: 1Q73Q2JULR) |
| 70518-0532 | 10 | mg/mL | Sodium Sulfite (1.5 mg in 1 mL) (UNII: VTK01UQK3G), Sodium Citrate (16.5 mg in 1 mL) (UNII: 1Q73Q2JULR), Benzyl Alcohol (10.42 mg in 1 mL) (UNII: LKG8 49 4WBH), Water (UNII: 059QF0KO0R), Sodium Hydoxide (UNII: 55X04QC32I), Citric Acid Monohydrate (UNII: 2968PHW8QP) |
| 70518-0621 | 4 | mg/mL | Sodium Citrate (11 mg in 1 mL) (UNII: 1Q73Q2JULR), Sodium Sulfite (1 mg in 1 mL) (UNII: VTK01UQK3G), Benzyl Alcohol (10 mg in 1 ml) (UNII: LKG8494WBH), Sodium Hydroxide (UNII: 55X04QC32I), Citric Acid Monohydrate (UNII: 2968PHW8QP) |
| 70518-0872 | 4 | mg/mL | Sodium Citrate (11 mg in 1 mL) (UNII: 1Q73Q2JULR), Sodium Sulfite (1 mg in 1 mL) (UNII: VTK01UQK3G), Benzyl Alcohol (10 mg in 1 ml) (UNII: LKG8494WBH), Sodium Hydroxide (UNII: 55X04QC32I), Citric Acid Monohydrate (UNII: 2968PHW8QP) |
| 71872-7021 | 4 | mg/mL | Benzyl Alcohol (10 mg in 1 mL) (UNII: LKG8494WBH), Sodium Sulfite (1 mg in 1 mL) (UNII: VTK01UQK3G), Anhydrous Trisodium Citrate (UNII: RS7A450LGA), Anhydrous Citric Acid (UNII: XF417D3PSL), Sodium Hydroxide (55X04QC32I), Water (059QF0KO0R) |
| 71872-7090 | 10 | mg/mL | Methylparaben (1.5 mg in 1 mL) (UNII: A2I8C7HI9T); Propylparaben (0.2 mg in 1 mL) (UNII: Z8IX2SC1OH); Edetate Disodium (0.11 mg in 1 mL) (UNII: 7FLD9 1C8 6K); Anhydrous Trisodium Citrate (10 mg in 1 mL) (UNII: |

TABLE B-continued

| Examples of Dexamethasone Sodium Phosphate formulations including excipient profile (U.S.) | | | |
|---|---|---|---|
| | | | RS7A450LGA); Citric Acid Monohydrate (UNII: 2968PHW8QP); Sodium Hydroxide (UNIIL 55X04QC321); Water (UNII: 059QF0KO0R) |
| 71872-7091 | 10 | mg/mL | Sodium Sulfite (1.5 mg in 1 mL) (UnII: VTK01UQK3G); Sodium Citrate (16.5 mg in 1 mL) (UNII: 1Q73Q2JULR); Benzyl Alcohol (10.42 mg in 1 mL) (UNII: LKG8494WBH); Water (UNII: 059QF0KO0R); Sodium Hydroxide (UNII: 55X04QC321) Citric Acid Monohydrate (UNII: 296PHW8QP) |
| 71872-7092 | 4 | mg/mL | Benzyl Alcohol (10 mg in 1 mL) (UNII: LKG8494WBH), Sodium Sulfite (1 mg in 1 mL) (UNII: VTK01UQK3G), Anhydrous Trisodium Citrate (UNII: RS7A450LGA), Anhydrous Citric Acid (UNII: XF417D3PSL), Sodium Hydroxide (55X04QC32I), Water (059QF0KO0R) |
| 71872-7128 | 4 | mg/mL | Benzyl Alcohol (10 mg in 1 mL) (UNII: LKG8494WBH), Sodium Sulfite (1 mg in 1 mL) (UNII: VTK01UQK3G), Anhydrous Trisodium Citrate (UNII: RS7A450LGA), Anhydrous Citric Acid (UNII: XF417D3PSL), Sodium Hydroxide (55X04QC32I), Water (059QF0KO0R) |
| 76045-106 | 4 | mg/mL | Citric Acid Monohydrate (UNII: 2968PHW8QP), Trisodium Citrate Dihydrate (UNII: B22547B95K), Water (UNII: 059QF0KO0R), Sodium Hydroxide (UNII: 55X04QC32I) |
| 51655-012 | 4 | mg/1 | |
| 71879-001 | 517 | ug/.005 mL | ACETYLTRIETHYL CITRATE (5233 ug in 0.005 mL) (UNII: 5WBR36T90E); Nitrogen (UNII: N762921K75) |
| 76420-270 | 10 | mg/mL | Sodium Citrate (UNII: 1Q73Q2JULR), Citric Acid Monohydrate (UNII: 2968PHW8QP), Sodium Hydroxide (UNII: 55X04QC32I) |
| 0998-0615 | 1 | mg/mL | BENZALKONIUM CHLORIDE (UNII: F5UM2KM3W7), HYPROMELLOSES (UNII: 3NXW29V3WO), SODIUM CHLORIDE (UNII: 451W47IQ8X), SODIUM PHOSPHATE, DIBASIC (UNII: GR686LBA74), POLYSORBATE 80 (UNII: 6OZP39ZG8H), EDETATE DISODIUM (UNII: 7FLD91C86K), CITRIC ACID MONOHYDRATE (UNII: 2968PHW8QP), SODIUM HYDROXIDE (UNII: 55X04QC32I) WATER (UNII: 059QF0KO0R) |
| 71205-013 | 1.5 | mg/1 | ANHYDROUS LACTOSE (UNII: 3SY5LH9PMK), CROSCARMELLOSE SODIUM (UNII: M28OL1HH48), MAGNESIUM STEARATE (UNII: 70097M6I30), MICROCRYSTALLINE CELLULOSE (UNII: OP1R32D61U), STEARIC ACID (UNII: 4ELV7Z65AP), FD&C RED NO. 40 (UNII: WZB9127XOA) |
| 71205-012 | 1.5 | mg/1 | ANHYDROUS LACTOSE (UNII: 3SY5LH9PMK), CROSCARMELLOSE SODIUM (UNII: M28OL1HH48), MAGNESIUM STEARATE (UNII: 70097M6I30), MICROCRYSTALLINE CELLULOSE (UNII: OP1R32D61U), STEARIC ACID (UNII: 4ELV7Z65AP), FD&C RED NO.40 (UNII: WZB9127XOA) |
| 69677-071 | 10 | mg/mL | SODIUM HYDROXIDE (UNII: 55X04QC32I), SODIUM CITRATE (24.5 mg in 1 mL)(UNII: 1Q73Q2JULR), CITRIC ACID MONOHYDRATE (UNII: 2968PHW8QP) |
| 70529-112 | 4 | mg/mL | SODIUM CITRATE, UNSPECIFIED FORM (11 mg in 1 mL) (UNII: 1Q73Q2JULR), SODIUM SULFITE (1 mg in 1 mL) (UNII: VTK0 1UQK3G), |

TABLE B-continued

| Examples of Dexamethasone Sodium Phosphate formulations including excipient profile (U.S.) | | | |
|---|---|---|---|
| | | | BENZYL ALCOHOL (10 mg in 1 mL) (UNII: LKG8 49 4WBH), SODIUM HYDROXIDE (UNII: 55X0 4QC32I), CITRIC ACID MONOHYDRATE (UNII: 2968PHW8QP) |
| 53225-3660 | 10 | mg/mL | SODIUM SULFITE (1.5 mg in 1 mL) (UNII: VTK01UQK3G), SODIUM CITRATE (16.5 mg in 1 mL) (UNII: 1Q73Q2JULR), BENZYL ALCOHOL (10.42 mg in 1 mL) (UNII: LKG8 49 4WBH), WATER (UNII: 059QF0KO0R), SODIUM HYDROXIDE (UNII: 55X04QC32I), CITRIC ACID MONOHYDRATE (UNII: 2968PHW8QP) |
| 76420-810 | 10 | mg/mL | Sodium Citrate (UNII: 1Q73Q2JULR), Citric Acid Monohydrate (UNII: 2968PHW8QP), Sodium Hydroxide (UNII: 55X04QC32I) |
| 70112-555 | 10 | mg/mL | SODIUM HYDROXIDE (UNII: 55X04QC32I), SODIUM CITRATE (24.5 mg in 1 mL) (UNII: 1Q73Q2JULR), CITRIC ACID MONOHYDRATE (UNII: 2968PHW8QP) |
| withdrawn 0006-7646-03 | 24 | mg/ml | 8 mg/ml creatinine, 10 mg/ml sodium citrate, 0.5 mg/ml disodium edetate, sodium hydroxide to adjust pH, and Water for Injection q.s., with 1 mg/ml sodium bisulfite, 1.5 mg/ml methylparaben, and 0.2 mg/ml propylparaben added as preservatives. |

TABLE C

Examples of Dexamethasone Sodium Phosphate formulations (U.S. veterinary market) - Products for veterinary market

| NDC or drug code | Active ingredient | Brand Name | Excipients | Concen-tration | Vial | Total Amount |
|---|---|---|---|---|---|---|
| 0061-0884-01 | Dexamethasone | Azium | Per ml: 500 mg polyethylene glycol 400, 9 mg benzyl alcohol, 1.8 mg methylparaben and 0.2 mg propylparaben as preservatives, 4.75% alcohol, HCl to adjust pH to approximately 4.9, and water for injection q.s. | 2 mg/ml dexameth-asone | 100 mL | 200 mg dexameth-asone |
| 2314118 | Dexamethasone sodium phosphate | Dexacort 5 | 1 mg/ml methylparahydroxybenzoate, 0.1 mg/ml propylparahydroxybenzoate | 5 mg/ml | 100 ml | 500 mg |
| ACVM A001421 | Dexamethasone sodium phosphate | Dexadreson | 15.6 mg/mL benzyl alcohol | 2 mg/mL | 50 ml | 100 mg |
| 11695-4017 | Dexamethasone | Dexaject | Per ml: 500 mg polyethylene glycol 400, 9 mg benzyl alcohol, 1.8 mg methylparaben and 0.2 mg propylparaben as preservatives, 4.75% alcohol, HCl to adjust pH to approximately 4.9, water for injection q.s. | 2 mg/mL | 100 mL | 200 mg |
| 11695-4013 | Dexamethasone sodium phosphate | Dexaject SP | Per ml: Sodium Citrate 10 mg, Sodium Bisulfite 2 mg, Benzyl Alcohol 1.5% as preservative, in Water for Injection q.s. Sodium Hydroxide and/or Hydrochloric Acid to adjust pH to between 7.0 and 8.5. | 4 mg/mL DSP | 100 mL | 400 mg |
| 50989-074-12 | dexamethasone | Dexamethasone (Vedco, Inc) | Per ml: 500 mg polyethylene glycol 400, 9 mg benzyl alcohol, 1.8 mg methylparaben and 0.2 mg propylparaben as preservatives, 4.75% alcohol, HCl and/or NaOH to adjust pH to approximately 4.9, water for injection q.s. | 2 mg/mL | 100 mL | 200 mg |
| 57561-953 | dexamethasone | Dexamethasone (Agri Laboratories, Ltd.) | Per ml: 500 mg polyethylene glycol 400, 9 mg benzyl alcohol, 1.8 mg methylparaben and 0.2 mg propylparaben as preservatives, 1.75% alcohol, HCl to adjust pH to approximately 4.9, water for injection q.s. | 2 mg/mL | 100 mL | 200 mg |

TABLE C-continued

Examples of Dexamethasone Sodium Phosphate formulations (U.S. veterinary market) - Products for veterinary market

| NDC or drug code | Active ingredient | Brand Name | Excipients | Concen-tration | Vial | Total Amount |
|---|---|---|---|---|---|---|
| 57319-560-05 | Dexamethasone | Dexamethasone (Phoenix Pharmaceuticals) | Per ml: 500 mg polyethylene glycol 400, 9 mg benzyl alcohol, 1.8 mg methylparaben and 0.2 mg propylparaben as preservatives, 4.75% alcohol, HCl to adjust pH to approximately 4.9, water for injection q.s. | 2 mg/mL | 100 mL | 200 mg |
| 57561-953-04 | Dexamethasone | Dexamethasone injection (Agrilabs) | polyethylene glycol 400, Benzyl alcohol, Methylparaben and propylparaben. | 2 mg/ml | 100 mL | 200 mg |
| 49884-084-01 | Dexamethasone | Dexamethasone injection (Vettek) | Per ml: 500 mg polyethylene glycol 400; 9 mg benzyl alcohol, 1.8 mg methylparaben, and 0.2 mg propylparaben as preservatives; 4.75% alcohol; HCl to adjust pH to approximately 4.9; water for injection qs. | 2 mg/mL | 100 mL | 200 mg |
| 54925-067-10 | Dexamethasone | Dexamethasone Solution | Per ml: 500 mg polyethylene glycol 400, 9 mg benzyl alcohol, 1.8 mg methylparaben and 0.2 mg propylparaben as preservatives, 4.75% alcohol, HCl and/or sodium hydroxide to adjust pH to approximately 4.9, Water for Injection q.s. | 2 mg/mL | 100 mL | 200 mg |
| 13985-043-29 | Dexamethasone sodium phosphate | Dexamethasone SP | Per ml: Sodium Citrate 10 mg, Sodium Bisulfite 2 mg, Benzyl Alcohol 1.5% as preservative, in Water for Injection q.s. Sodium Hydroxide and/or Hydrochloric Acid to adjust pH to between 7.0 and 8.5. | 4 mg/mL DSP | 100 mL | 400 mg |
| 61133-0899-9 | dexamethasone | Dexium | Per ml: 500 mg polyethylene glycol 400, 9 mg benzyl alcohol, 1.8 mg methylparaben and 0.2 mg propylparaben as preservatives, 4.75% alcohol, HCl to adjust pH to approximately 4.9, water for injection q.s. | 2 mg/ml dexamethasone | 100 mL | 200 mg |
| | Dexamethasone | Dexa-ject | 15 mg/ml Benzyl Alcohol | 2 mg/mL | 50 or 100 ml | 100 or 200 mg |
| 11695-4013-1 | Dexamethasone Sodium Phosphate | DEXAJECT SP | Per ml: Sodium Citrate 10 mg, Sodium Bisulfite 2 mg, Benzyl Alcohol 1.5% as preservative, in Water for Injection q.s. Sodium Hydroxide and/or Hydrochloric Acid to adjust pH to between 7.0 and 8.5. | 4 mg/mL | 100 mL | 400 mg |
| 2/5/412/2006 | Dexamethasone Sodium phosphate | Dexafort Ject | Not disclosed | 5 mg/ml | 100 mL | 500 mg |
| 13985-533-25, 13985-533-03 | Dexamethasone | Dexamethasone (Vet One) | Per ml: 500 mg polyethylene glycol 400, 9 mg benzyl alcohol, 1.8 mg methylparaben and 0.2 mg propylparaben, 4.75% alcohol, HCl to adjust pH to approximately 4.9, water for injection q.s. | 2 mg/ml | 100 ml | 200 mg |
| 50989-437-12 | Dexamethasone | Dexamethasone (Vedco, Inc) | Per ml: 500 mg polyethylene glycol 400, 9 mg benzyl alcohol, 1.8 mg methylparaben and 0.2 mg propylparaben, 4.75% alcohol, HCl to adjust pH to approximately 4.9, water for injection q.s. | 2 mg/ml | 100 ml | 200 mg |
| 17033-207-76 | Per ml: 40 mg thiabendazole, 1 mg dexamethasone, 3.2 mg neomycin (from neomycin sulfate) | ThiDexaVet | glycerin, propylene glycol, purifed water, hypophosphorous acid, calcium hypophosphite; about 8.5% ethyl alcohol and about 0.5% benzyl alcohol. | 1 mg/ml | 7.5 ml | 7.5 mg |

TABLE D

Examples of high dose Dexamethasone Sodium Phosphate formulations (international market)
High concentration dexamethasone sodium phosphate approved products

| Compound | Brand | Strength (mg/ml) | Vial Size | Actives per ml | Inactives per ml | Preserva-tives per ml | Notes | Approved & Registered Markets |
|---|---|---|---|---|---|---|---|---|
| Dexamethasone Sodium Phosphate NDC 0006-7646-03 | Decadron (Merck) | 24 | 5 ml (120 mg) | 20 mg Dexamethasone (100 mg) | 10 mg sodium citrate 0.5 mg disodium edetate sodium hydroxide | 1 mg sodium bisulfite 1.5 mg methylparaben 0.2 mg | NOT AVAILABLE. For intravenous injection only. DECADRON Phos-phate injection can | 1. USA 2. UK 3. Ireland |

TABLE D-continued

Examples of high dose Dexamethasone Sodium Phosphate formulations (international market)
High concentration dexamethasone sodium phosphate approved products

| Compound | Brand | Strength (mg/ml) | Vial Size | Actives per ml | Inactives per ml | Preserva-tives per ml | Notes | Approved & Registered Markets |
|---|---|---|---|---|---|---|---|---|
| | | | | | to adjust pH water for injection q.s. | propylparaben 8 mg creatinine | be given directly from the vial, or it can be added to Sodium Chloride Injection or Dextrose Injection and administered by intravenous drip. Solutions used for intravenous administration or further dilution of this product should be preservative-free when used in the neonate, especially the premature infant. When it is mixed with an infusion solution, sterile precautions should be observed. Since infusion solutions generally do not contain preservatives, mixtures should be used within 24 hours. Parenteral drug products should be inspected visually for particulate matter and discoloration prior to administration, whenever solution and container permit. | |
| Dexamethasone Sodium Phosphate NDC N/A | DBL ™ Dexameth-asone (Hospira) | 24 | 5 ml (120 mg) | 20 mg Dexamethasone (100 mg) | 10 mg sodium citrate 0.5 mg disodium edetate sodium hydroxide to adjust pH water for injection q.s. | 8 mg creatinine | NOT AVAILABLE. The intravenous and intramuscular routes of administration of DBL ™ Dexamethasone Sodium Phosphate Injection should only be used where acute illness or life-threatening situations exist. Oral therapy should be substituted as soon as possible. | 1. Australia 2. New Zealand (active) 3. Ireland 4. United Kingdom |
| Dexamethasone Sodium Phosphate NDC 63323-516-10 | Fresenius Kabi APP Pharma | 10 | 10 ml (100 mg) | 8.30 mg Dexamethasone (82.5 mg) | 13.5 mg sodium citrate, dihydrate; and Water for Injection, q.s. pH adjusted with citric acid or sodium hydroxide, if necessary. pH: 7.0 to 8.5. | 10 mg Benzyl alcohol | AVAILABLE | |
| Dexamethasone Sodium Phosphate NDC 0069-4541-02 | Pfizer | 10 | 10 ml (100 mg) | Dexamethasone sodium phosphate 11 mg (equivalent to dexamethasone phosphate 10 mg). | Edetate Disodium 0.11 mg; Sodium Citrate Anhydrous 10 mg; Citric Acid and/or Sodium Hydroxide q.s to adjust pH 7.0 to 8.5 and Water for Injection q.s to 1 mL | Methylparaben 1.5 mg; Propylparaben 0.2 mg | AVAILABLE | |
| Dexamethasone Sodium Phosphate | Solcort ™ Injection 100 mg | 24 | 5 ml (120 mg) | 20 mg Dexamethasone (100 mg) | Per 5 ml: Citric acid monohydrate | Benzethonium chloride 0.5 mg/5 ml | AVAILABLE | 1. Japan Restricted to |

TABLE D-continued

Examples of high dose Dexamethasone Sodium Phosphate formulations (international market)
High concentration dexamethasone sodium phosphate approved products

| Compound | Brand | Strength Vial (mg/ml) Size | Actives per ml | Inactives per ml | Preserva-tives per ml | Notes | Approved & Registered Markets |
|---|---|---|---|---|---|---|---|
| NDC 22000AMX00346000 | Fuji Pharm (Shelf life: 3 years) | | | 100 mg pH adjustment agent (Appropriate amount) | | | treatment of shock: hemorrhagic shock, traumatic shock emergencies, and peri-operative and post-operative shock. |

TABLE E

Examples of patents disclosing Dexamethasone formulations with a much higher sulfite or excipient content

| Patent | Title | Composition | | | | | Stability | Comparison to AVM0703 |
|---|---|---|---|---|---|---|---|---|
| WO 2017/ 097432 A1 | Preservative free pharmaceutical composition for ophthalmic administration containing dexamethasone | Dexamethasone phosphate | 1.000 | 1.000 | 1.000 | 1.000 | The final product was stored at 0, 1, 3, 6 and 9 months under long term (25° C./60% RH) and accelerated storage conditions (40° C./75% RH), which did not significantly change the realted substances profile conforming to the specification limits. | 1/24 of DSP concentration; 2x Disodium EDTA concentration |
| | | Dexamethasone sodium phosphate | 1.093 | 1.093 | 1.093 | 1.093 | | |
| | | Disodium EDTA | 1.000 | 1.000 | 1.000 | 1.000 | | |
| | | Sodium chloride | 7.500 | 6.920 | 7.600 | 6.600 | | |
| | | Disodium phosphate dodecahydrate | 4.500 | 6.000 | 6.000 | 7.450 | | |
| | | NaOH/HCl 0.1/1N | q.s. to 7.6 | | | | | |
| | | Total solution volume (ml) | 1.00 | | | | | |
| CN 107375200 A | Dexamethasone sodium phosphate injection and preparing method thereof | Sodium hydrogen sulfite (g) | 0.4 | | | | Stored for more than 2 years, no precipi-tates precipitated in the life of the product (at 50° C.) | Together: 2000 ppm sulfite present (AVM0703 only 35 ppm) = 57x more than AVM0703; 30 minutes (steam sterilized); AVM0703: aseptic manufacture |
| | | Anhydrous sulfite (g) | 1.6 | | | | | |
| | | Dexamethasone sodium phosphate (g) | 1 | | | | | |
| | | Propylene glycol (ml) | 250 | | | | | |
| | | NaOH 1N | pH 7.5-8.0 | | | | | |
| | | Water for injection (ml) | 1000 | | | | | |
| CN 101623291 A | Dexamethasone sodium phosphate injection | Dexamethasone sodium phosphate | 0.1 to 1% | | | | Only 3 months stabil-ity (at 60° C./75% RH) | As antioxidant, sodium bisulfite, sodium sulfite, A-tocopherol, sodium metabisulfite, and sodium thiosulfate in one or more of 0.05%-0.2% (14.7x more than AVM0703; sodium sulfite content of only 0.0034%) |
| | | Pharmaceutically acceptable glycol (medicinal propylene glycol) | 0 to 2% | | | | | |
| | | Sodium dihydrogen phosphate:disodium hydrogen phosphate | 0.01 to 0.1 percent of mixed phosphate buffer according to ratio of 0-1:10 | | | | | |
| | | Water for injection | | | | | | |
| | | Example 5 | | | | | | |
| | | Dexamethasone sodium phosphate (g) | 5 | | | | | |
| | | Disodium hydrogen phosphate (g) | 0.5 | | | | | |

TABLE E-continued

Examples of patents disclosing Dexamethasone formulations with a much higher sulfite or excipient content

| Patent | Title | Composition | | | Stability | Comparison to AVM0703 |
|---|---|---|---|---|---|---|
| | | Medicinal propylene glycol (g) | | 10 | | |
| | | | | Adjusted to pH 8.0, filtered, dispensed, sterilized to give injections per ml solution of dexameth-asone sodium phosphate 5 mg | | |
| | | Water for injection (ml) | | 1000 | | |
| EP 2735305 A1 | Stabilised liquid pharmaceutical preparations | INGREDIENTS: FORMULATION A (according to the invention); oral drops | | Quantity for 1 ml: | 36 months under if stored at room temperature (25° C. 62° C./65% RH 65%) an | Use of cyclo-dextrins is limited by cost and toxicity at high doses. Likewise for propylene glycol: dose limiting, especially for pediatric use! |
| | | Dexamethasone sodium phosphate | | 2.00 mg | | |
| | | Sodium benzoate | | 1.50 mg | | |
| | | Propylene glycol | | 700.00 mg | | |
| | | Sodium dihydrogen Phosphate dihydrate | | 5.50 mg | | |
| | | Saccharin sodium | | 2.00 mg | | |
| | | Hydroxypropylbetadex | | 6.50 mg | | |
| | | Disodium edetate | | 1.00 mg | | |
| | | Sodium hydroxide | | 0.6667 mg | | |
| | | Purified water | | q.s. to 1.00 ml (328 mg) | | |
| | | EXAMPLE 4 | | | | |
| | | Preparation of an aqueous solution for injectable liquids | | | | |
| | | Components | Unit | Per 100 ml | | |
| | | Dexamethasone sodium phosphate | mg | 200 | | |
| | | Propylene glycol | g | 10 | | |
| | | Hydroxypropyl beta cyclodextrin | g | 0.65 | | |
| | | Sodium dihydrogen phosphate dihydrate | | q.s. for pH 7.0-8.0 | | |
| | | Sodium hydroxide | | q.s. for pH 7.0-8.0 | | |
| | | Purified watwer | | q.s. for 100 ml | | |

TABLE F

Examples of Dexamethasone formulations including their shelf-life as disclosed by the manufacturers in comparison with the AVM0703 F10 formulation

| Name | Drug Code | Active Pharma-ceutical Ingredient | Form and Adminis-tration | Company | Strength | Use | Composition | Volume | Shelf-life | Compar-ison |
|---|---|---|---|---|---|---|---|---|---|---|
| AVM0703 (F10) | | Dexamethasone Sodium Phosphate | INJECTION, SOLUTION, Oral Administration | AVM Biotechnology | 24 mg/ml | Human Use | Sodium Citrate (10 mg in 1 ml); Disodium Edetate (0.5 mg in 1 ml); Sodium Hydroxide (pH adjustment to 7.6) | 50 ml (Target fill: 51.0 ml; nominal fill 50.0 ml) | 29-48 months | highest strength, volume and longest shelf-life, no preservatives |
| Dexameth-asone Sodium Phosphate | 63323-506-01 | Dexamethasone Sodium Phosphate | INJECTION, SOLUTION | Fresenius Kabi USA, LLC | 10 mg/ml | Human Use | Sodium Citrate (24.75 mg in 1 mL); Sodium Hydroxide, Citric Acid Monohydrate | 1 ml | 24 months | low strength, very low volume |
| Dexameth-asone | PL 04515/0020 | Dexamethasone Sodium Phosphate | Injection | Hospira | 4 mg/ml | Human Use | 10 mg/ml Sodium citrate, 0.5 mg/ml disodium edetate, 0.07 mg/ml sodium | 2 ml | 18 months | 70 ppm sulfite present |

TABLE F-continued

Examples of Dexamethasone formulations including their shelf-life as disclosed by the manufacturers in comparison with the AVM0703 F10 formulation

| Name | Drug Code | Active Pharma-ceutical Ingredient | Form and Adminis-tration | Company | Strength | Use | Composition | Volume | Shelf-life | Compar-ison |
|---|---|---|---|---|---|---|---|---|---|---|
| | | | | | | | sulphite anhydrous (E221), Water for Injections, sodium hydroxide and hydrochloric acid. | | | |
| Dexa-ject | | Dexamethasone Sodium Phosphate | Injection | Dopharma | 2 mg/mL | Animal Use | 15 mg/ml Benzyl Alcohol | 100 ml | 18 months | benzyl alcohol present |

REFERENCES

A number of publications are cited above in order to more fully describe and disclose the invention and the state of the art to which the invention pertains. Full citations for these references are provided below:

American Hospital Formulary Service. Volumes I and II. Washington, D.C.: American
Society of Hospital Pharmacists, to 1984, p. 40:08
Thabet et al. 2018; J Clin Pharmacol. 2018 October; 58 Suppl 10:S26-S35
Oishi et al 2002; Food Chem Toxicol. 2002 December; 40(12):1807-13.
Savage et al. 2012; J Allergy Clin Immunol. 2012 August; 130(2):453-60.e7.
Spanier et al. 2014; Allergy Asthma Proc. 2014 November-December; 35(6):475-81.
Gershanik et al., 1982; N Engl J Med. 1982 Nov. 25; 307(22):1384-8.
Hiller et al., 1986; Pediatrics. 1986 April; 77(4):500-6.
Benda et al., 1986; Pediatrics. 1986 April; 77(4):507-12.
Jardine and Rogers, 1989; Pediatrics. 1989 February; 83(2):153-60.
Benjamin et al. 2011; Skin Res Technol. 2012 August; 18(3):272-7
Dao et al. 2012; Dermatitis. 2012 July-August; 23(4): 162-6
Sanidad et al. 2018; Toxicol Sci. 2018 Jun. 1; 163(2): 490-499
Lim et al. 2014; J Pediatr Pharmacol Ther. 2014 October-December; 19(4): 277-282.
Darby et al. 2012; Ann Clin Biochem. 2012 May; 49(Pt 3):292-4
EFSA Journal 2016; 14(4):4438
Nellis et al. 2015; Arch Dis Child. 2015 July; 100(7): 694-9
Turner et al. 2014; Adv Drug Deliv Rev. 2014 June; 73:89-101
Serafin et al., 2017; Blood. 2017 Dec. 21; 130(25):2750-2761
WO 2012/024519
WO 2018/183927
PCT/US2019/054395
WO 2017/097432 A1
CN 107375200 A
CN 101623291 A
EP 2735305 A

STATEMENTS OF INVENTION

101. A pharmaceutical composition comprising (i) a glucocorticoid, packaged with a headspace (volume; [ml]) to glucocorticoid (weight [mg]) ratio of 0-0.00588, and (ii) a preservative in a concentration of less than 70 ppm.
102. The pharmaceutical composition of statement 101, wherein the glucocorticoid is dexamethasone.
103. The pharmaceutical composition of statement 101, wherein the preservative is a sulfite.
104. The pharmaceutical composition of statement 103, wherein the sulfite is sodium sulfite.
105. The pharmaceutical composition of statement 101, wherein the concentration of the preservative is 0 ppm.
106. The pharmaceutical composition of statement 101 further comprising a chelating agent.
107. The pharmaceutical composition of statement 106, wherein the chelating agent is disodium edetate.
108. The pharmaceutical composition of statement 101, wherein the concentration of the chelating agent disodium edetate is 0 ppm.
109. A method for producing a pharmaceutical composition having a low concentration of preservative, based on packing of said pharmaceutical composition with a headspace (volume; [ml]) to glucocorticoid (weight [mg]) ratio of 0-0.00588.
110. The method of statement 109, wherein the preservative is a sulfite.
111. The method of statement 109, wherein the sulfite is sodium sulfite.
112. The method of statement 109, wherein the concentration of the preservative is 0 ppm.
113. The method of statement 109, further comprising a chelating agent.
114. The method of statement 109, further comprising disodium edetate as chelating agent.
115. The method of statement 109, wherein the concentration of the chelating agent disodium edetate is 0 ppm.
116. A method of treating a host in need of glucocorticoid treatment, comprising administering the pharmaceutical composition of claim statement 101.
117. The method of statement 116, wherein the glucocorticoid is dexamethasone.
118. The method of statement 116, wherein the headspace to glucocorticoid is 0-0.00588.
119. The method of statement 116, wherein the preservative is a sulfite.
120. The method of statement 116, wherein the sulfite is sodium sulfite.
121. The method of statement 116, wherein the concentration of the preservative is 0 ppm.

122. The method of statement 116, further comprising a chelating agent.

123. The method of statement 116, further comprising disodium edetate as chelating agent.

124. The method of statement 116, wherein the concentration of the chelating agent disodium edetate is 0 ppm.

201. An aqueous pharmaceutical formulation comprising a glucocorticoid, wherein the formulation is packaged in a container with a headspace volume (ml) to total glucocorticoid content (mg) ratio of 0.007 or less.

Headspace to API Ratio

202. The aqueous pharmaceutical formulation of statement 201, wherein the headspace volume (ml) to total glucocorticoid content (mg) ratio is 0.0065 or less, 0.0060 or less, 0.00588 or less, 0.0055 or less, 0.0050 or less, 0.0045 or less, 0.0040 or less, 0.0035 or less, 0.0030 or less, 0.0025 or less, 0.0020 or less, 0.0015 or less, or 0.0010 or less.

203. The aqueous pharmaceutical formulation of statement 202, wherein the headspace volume (ml) to total glucocorticoid content (mg) ratio is 0.00588 or less.

Sulfite to API Ratio

204. The aqueous pharmaceutical formulation of any one of statements 201 to 203, wherein the formulation is packaged in a container with a total sulfite content (mg) to total glucocorticoid content (mg) ratio of 0.0040 or less, 0.0035 or less, 0.0030 or less, 0.0025 or less, 0.0020 or less, 0.0015 or less, 0.00146 or less, or 0.0010 or less.

205. The aqueous pharmaceutical formulation of statement 204, wherein the formulation is packaged in a container with a total sulfite content (mg) to total glucocorticoid content (mg) ratio of 0.00150 or less, preferably 0.00146 or less.

Headspace Volume

206. The aqueous pharmaceutical formulation of any one of statements 201 to 205, wherein the headspace volume is or is less than about 20, 19, 18, 17, 16, 15, 14, 13, 12, 11, 10, 9, 8, 7, 6, 5, 4, 3, 2, or 1 ml.

207. The aqueous pharmaceutical formulation of statement 206, wherein the headspace volume is or is less than about 8 ml.

Headspace Oxygen

208. The aqueous pharmaceutical formulation of any one of statements 201 to 207, wherein the headspace volume comprises less than about 21, 20, 19, 18, 17, 16, 15, 14, 13, 12, 11, 10, 9, 8, 7, 6, 5, 4, 3, 2, or 1% oxygen.

209. The aqueous pharmaceutical formulation of statement 208, wherein the headspace volume comprises less than about 5% oxygen.

210. The aqueous pharmaceutical formulation of any one of statements 201 to 207, wherein the headspace volume comprises 0% oxygen.

Preservative Concentration

211. The aqueous pharmaceutical formulation of any one of statements 201 to 210, wherein the formulation comprises one or more preservative, wherein the concentration of preservatives is or is less than about 0.1 mg/ml.

212. The aqueous pharmaceutical formulation of statement 211, wherein the concentration of preservatives is or is less than about 0.09 mg/ml, is or is less than about 0.08 mg/ml, is or is less than about 0.07 mg/ml, is or is less than about 0.06 mg/ml, is or is less than about 0.05 mg/ml, is or is less than about 0.04 mg/ml, is or is less than about 0.035 mg/ml, is or is less than about 0.03 mg/ml, is or is less than about 0.02 mg/ml, or is or is less than about 0.01 mg/ml.

213. The aqueous pharmaceutical formulation of statement 212, wherein the concentration of preservatives is or is less than about 0.07 mg/ml, preferably wherein the concentration of preservatives is or is less than about 0.035 mg/ml.

214. The aqueous pharmaceutical formulation of any one of statements 201 to 210, wherein the concentration of preservative is 0 mg/ml.

215. The aqueous pharmaceutical formulation of any one of statements 201 to 210, wherein the formulation does not comprise a preservative.

Preservative Identity

216. The aqueous pharmaceutical formulation of any one of statements 211 to 215, wherein the preservative is a sulfite, a paraben, benzyl alcohol, benzethonium chloride, propylene glycol, and/or creatinine.

217. The aqueous pharmaceutical formulation of statement 216, wherein the sulfite is sodium sulfite (anhydrous), sodium bisulfite, and/or sodium metabisulfite.

218. The aqueous pharmaceutical formulation of statement 216, wherein the paraben is methylparaben, propylparaben, ethylparaben, butylparaben, isopropylparaben and/or isobutylparaben, preferably wherein the paraben is methylparaben and/or propylparaben.

Chelating Agent Concentration

219. The aqueous pharmaceutical formulation of any one of statements 201 to 219, wherein the formulation comprises one or more chelating agent, wherein the concentration of chelating agent is or is less than about 0.50 mg/ml.

220. The aqueous pharmaceutical formulation of statement 219, wherein the concentration of chelating agent is or is less than about 0.45 mg/ml, is or is less than about 0.40 mg/ml, is or is less than about 0.35 mg/ml, is or is less than about 0.30 mg/ml, is or is less than about 0.25 mg/ml, is or is less than about 0.20 mg/ml, is or is less than about 0.15 mg/ml, is or is less than about 0.10 mg/ml, is or is less than about 0.10 mg/ml, or is or is less than about 0.05 mg/ml.

221. The aqueous pharmaceutical formulation of any one of statements 201 to 219, wherein the concentration of chelating agent is 0 mg/ml.

222. The aqueous pharmaceutical formulation of any one of statements 201 to 219, wherein the formulation does not comprise a chelating agent.

Chelating Agent Identity

223. The aqueous pharmaceutical formulation of any one of statements 201 to 222, wherein the chelating agent is ethylenediaminetetraacetic acid (EDTA), sodium edetate, disodium edetate, tetrasodium edetate, calcium disodium edetate, calcium versetamide sodium, calteridol, and/or diethylenetriaminepenta acetic acid (DPTA).

224. The aqueous pharmaceutical formulation of statement 223, wherein the chelating agent is disodium edetate (disodium EDTA).

Glucocorticoid Identity

225. The aqueous pharmaceutical formulation of any one of statements 201 to 224, wherein the glucocorticoid is selected from the group consisting of dexamethasone, hydrocortisone, methylprednisolone, prednisone, prednisolone, prednylidene, cortisone, budesonide, betamethasone and beclomethasone.

226. The aqueous pharmaceutical formulation of statement 225, wherein the glucocorticoid comprises dexamethasone, optionally wherein the dexamethasone is selected from the group consisting of dexamethasone base, dexamethasone sodium phosphate, dexamethasone hemisuccinate, dexamethasone sodium succinate, dexamethasone succinate, and dexamethasone acetate.

227. The aqueous pharmaceutical formulation of statement 226, wherein the dexamethasone is dexamethasone sodium phosphate.

Glucocorticoid Concentration

228. The aqueous pharmaceutical formulation of any one of statements 201 to 227, wherein the concentration of glucocorticoid is or is at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 mg/ml.

229. The aqueous pharmaceutical formulation of statement 228, wherein the concentration of glucocorticoid is or is at least about 24 mg/ml.

230. The aqueous pharmaceutical formulation of statement 228, wherein the concentration of glucocorticoid is or is at least about 30 mg/ml.

231. The aqueous pharmaceutical formulation of statement 228, wherein the concentration of glucocorticoid is or is at least about 45 mg/ml.

Formulation pH

232. The aqueous pharmaceutical formulation of any one of statements 201 to 231, wherein the pH of the formulation is about 7.0 to about 8.2, about 7.2 to about 8.0, about 7.3 to about 7.9, or about 7.4 to about 7.8

233. The aqueous pharmaceutical formulation of statement 232, wherein the pH of the formulation is about 7.4 to about 7.8, preferably wherein the pH of the formulation is about 7.6.

Other Components of Formulation

234. The aqueous pharmaceutical formulation of any one of statements 201 to 233, wherein the formulation comprises a buffer.

235. The aqueous pharmaceutical formulation of statement 234, wherein the buffer is sodium citrate.

236. The aqueous pharmaceutical formulation of statement 234 or 235, wherein the concentration of buffer is about 10 mg/ml.

Container Type & Volume

237. The aqueous pharmaceutical formulation of any one of statements 201 to 236, wherein the container is a vial, ampoule, solvent reservoir, storage bottle, medical bottle, syringe, or bottle, preferably wherein the container is a vial, ampoule, or bottle.

238. The aqueous pharmaceutical formulation of any one of statements 201 to 237, wherein the volume of the container is or is at least about 1, 2, 3, 4, 5, 6, 7, 8, 9, 10, 15, 20, 25, 30, 35, 40, 45, 50, 51, 55, 60, 65, 70, 75, 80, 85, 90, 95, or 100 ml.

239. The aqueous pharmaceutical formulation of statement 238, wherein the volume of the container is or is at least about 51 ml.

240. The aqueous pharmaceutical formulation of any one of statements 201 to 239, wherein the volume of glucocorticoid packaged in the container is at least 1, 2, 3, 4, 5, 6, 7, 8, 9, 10, 15, 20, 25, 30, 35, 40, 45, 50, 55, 60, 65, 70, 75, 80, 85, 90, 95, or 100 ml.

Functional Features

241. The aqueous pharmaceutical formulation of any one of statements 201 to 240, wherein the shelf-life of the formulation is at least about 18, 24, 36, or 48 months when stored between 20° C. to 40° C. or between 15° C. to 20° C.

242. The aqueous pharmaceutical formulation of any one of statements 201 to 240, wherein the formulation remains stable when stored between 20° C. to 40° C. or between 15° C. to 20° C. for at least about 18, 24, 36, or 48 months.

243. The aqueous pharmaceutical formulation of any one of statements 201 to 242, wherein the formulation exhibits less than about 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0% degradation of the glucocorticoid when stored between 20° C. to 40° C. or between 15° C. to 20° C. for at least about 18, 24, 36, or 48 months.

244. The aqueous pharmaceutical formulation of any one of statements 201 to 242, wherein the amount of glucocorticoid in the formulation is maintained above about 95.0, 95.2, 95.4, 95.6, 96.0, 96.2, 96.4, 96.6, 96.8, 97.0, 97.2, 97.4, 97.6, 98.0, 98.2, 98.4, 98.6, 98.8, 99.0, 99.1, 99.2, 99.3, 99.4, 99.5, 99.6, 99.7, 99.8, or 99.9% as compared to the date of manufacture when the formulation is stored between 20° C. to 40° C. or between 15° C. to 20° C. for at least about 18, 24, 36, or 48 months.

245. The aqueous pharmaceutical formulation of any one of statements 201 to 242, wherein the amount of glucocorticoid in the formulation is maintained between ±1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% as compared to the date of manufacture when the formulation is stored between 20° C. to 40° C. or between 15° C. to 20° C. for at least about 18, 24, 36, or 48 months.

246. The aqueous pharmaceutical formulation of any one of statements 201 to 245, wherein the formulation exhibits less than ±0.1, 0.2, 0.3, 0.4, 0.5, 0.6, 0.7, 0.8, 0.9, 1.0, 1.2, 1.4, 1.6, 1.8, or 2.0 change in pH when stored between 20° C. to 40° C. or between 15° C. to 20° C. for at least about 18, 24, 36, or 48 months.

247. The aqueous pharmaceutical formulation of any one of statements 201 to 246, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity A when stored between 20° C. to 40° C. or between 15° C. to 20° C. for at least about 18, 24, 36, or 48 months.

248. The aqueous pharmaceutical formulation of any one of statements 201 to 247, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity B when stored between 20° C. to 40° C. or between 15° C. to 20° C. for at least about 18, 24, 36, or 48 months.

249. The aqueous pharmaceutical formulation of any one of statements 201 to 248, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity C when stored between 20° C. to 40° C. or between 15° C. to 20° C. for at least about 18, 24, 36, or 48 months.

250. The aqueous pharmaceutical formulation of any one of statements 201 to 249, wherein the glucocorticoid is dexamethasone sodium phosphate, and
wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity D when stored between 20° C. to 40° C. or between 15° C. to 20° C. for at least about 18, 24, 36, or 48 months.
251. The aqueous pharmaceutical formulation of any one of statements 201 to 250, wherein the glucocorticoid is dexamethasone sodium phosphate, and
wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity E when stored between 20° C. to 40° C. or between 15° C. to 20° C. for at least about 18, 24, 36, or 48 months.
252. The aqueous pharmaceutical formulation of any one of statements 201 to 251, wherein the glucocorticoid is dexamethasone sodium phosphate, and
wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity F when stored between 20° C. to 40° C. or between 15° C. to 20° C. for at least about 18, 24, 36, or 48 months.
253. The aqueous pharmaceutical formulation of any one of statements 201 to 252, wherein the glucocorticoid is dexamethasone sodium phosphate, and
wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity G when stored between 20° C. to 40° C. or between 15° C. to 20° C. for at least about 18, 24, 36, or 48 months.
254. The aqueous pharmaceutical formulation of any one of statements 201 to 253, wherein the formulation exhibits less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19 0.20, 0.21, 0.22, 0.23, 0.24, 0.25, 0.26, 0.27, 0.28, 0.29, or 0.30% accumulation of unspecified impurities when stored between 20° C. to 40° C. or between 15° C. to 20° C. for at least about 18, 24, 36, or 48 months.
255. The aqueous pharmaceutical formulation of any one of statements 201 to 254, wherein the formulation exhibits less than about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% accumulation of total impurities when stored between 20° C. to 40° C. or between 15° C. to 20° C. for at least about 18, 24, 36, or 48 months.

Medical Use

256. The aqueous pharmaceutical formulation of any one of statements 201 to 255, for use in a method of treatment.
257. Use of the aqueous pharmaceutical formulation of any one of statements 201 to 255 for the preparation of a medicament for use in a method of treatment.
258. A method of treatment comprising administering to a subject in need thereof, a therapeutically effective amount of the aqueous pharmaceutical formulation of any one of statements 201 to 255.
259. The formulation for use, use, or method of any one of statements 256 to 258, wherein the method is a method of reducing stem cell accumulation in the spleen in a subject, the method comprising administering the formulation to the subject prior to stem cell treatment.
260. The formulation for use, use, or method of any one of statements 256 to 258, wherein the method is a method of enhancing adoptive cellular therapy (ACT) in a subject, the method comprising administering the formulation to the subject prior to adoptive cellular therapy.
261. The formulation for use, use, or method of any one of statements 256 to 258, wherein the method is a method of treatment of a lymphocyte mediated disease in a subject, the method comprising administering the formulation to the subject.

Method of Manufacture

262. A method for stabilising an aqueous pharmaceutical formulation comprising a glucocorticoid, the method comprising packaging the aqueous pharmaceutical formulation of any one of statements 201 to 255 into a container with a headspace volume (ml) to total glucocorticoid content (mg) ratio of 0.007 or less.
301. An aqueous pharmaceutical formulation comprising a glucocorticoid and a preservative, wherein the concentration of glucocorticoid is at least about 24 mg/ml, and the concentration of preservative is less than about 0.1 mg/ml.
302. An aqueous pharmaceutical formulation comprising a glucocorticoid and a preservative, wherein the concentration of glucocorticoid is at least about 24 mg/ml, and wherein the preservative comprises:
a sulfite present in a concentration of less than about 1 mg/ml;
a paraben present in a concentration of less than about 0.2 mg/ml;
creatinine present in a concentration of less than about 8 mg/ml; and/or
benzethonium chloride present in a concentration of less than about 0.1 mg/ml.
303. The aqueous pharmaceutical formulation of statement 302, wherein the concentration of preservative is less than about 0.1 mg/ml.

Headspace to API Ratio

304. The aqueous pharmaceutical formulation of any one of statements 301 to 303, wherein the formulation is packaged in a container with a headspace volume (ml) to total glucocorticoid content (mg) ratio of 0.007 or less
305. The aqueous pharmaceutical formulation of statement 304, wherein the headspace volume (ml) to total glucocorticoid content (mg) ratio is 0.0065 or less, 0.0060 or less, 0.00588 or less, 0.0055 or less, 0.0050 or less, 0.0045 or less, 0.0040 or less, 0.0035 or less, 0.0030 or less, 0.0025 or less, 0.0020 or less, 0.0015 or less, or 0.0010 or less.
306. The aqueous pharmaceutical formulation of statement 305, wherein the headspace volume (ml) to total glucocorticoid content (mg) ratio is 0.00588 or less.

Sulfite to API Ratio

307. The aqueous pharmaceutical formulation of any one of statements 301 to 306, wherein the formulation is packaged in a container with a total sulfite content (mg) to total glucocorticoid content (mg) ratio of 0.0040 or less, 0.0035 or less, 0.0030 or less, 0.0025 or less, 0.0020 or less, 0.0015 or less, 0.00146 or less, or 0.0010 or less.
308. The aqueous pharmaceutical formulation of statement 307, wherein the formulation is packaged in a container with a total sulfite content (mg) to total glucocorticoid content (mg) ratio of 0.00150 or less, preferably 0.00146 or less.

Headspace Volume

309. The aqueous pharmaceutical formulation of any one of statements 301 to 308, wherein the headspace volume is or is less than about 20, 19, 18, 17, 16, 15, 14, 13, 12, 11, 10, 9, 8, 7, 6, 5, 4, 3, 2, or 1 ml.

310. The aqueous pharmaceutical formulation of statement 309, wherein the headspace volume is or is less than about 8 ml.

Headspace Oxygen

311. The aqueous pharmaceutical formulation of any one of statements 301 to 310, wherein the headspace volume comprises less than about 21, 20, 19, 18, 17, 16, 15, 14, 13, 12, 11, 10, 9, 8, 7, 6, 5, 4, 3, 2, or 1% oxygen.

312. The aqueous pharmaceutical formulation of statement 311, wherein the headspace volume comprises less than about 5% oxygen.

313. The aqueous pharmaceutical formulation of any one of statements 301 to 312, wherein the headspace volume comprises 0% oxygen.

Preservative Concentration

314. The aqueous pharmaceutical formulation of any one of statements 301 to 313, wherein the concentration of preservative is or is less than about 0.09 mg/ml, is or is less than about 0.08 mg/ml, is or is less than about 0.07 mg/ml, is or is less than about 0.06 mg/ml, is or is less than about 0.05 mg/ml, is or is less than about 0.04 mg/ml, is or is less than about 0.035 mg/ml, is or is less than about 0.03 mg/ml, is or is less than about 0.02 mg/ml, or is or is less than about 0.01 mg/ml.

315. The aqueous pharmaceutical formulation of statement 314, wherein the concentration of preservative is or is less than about 0.07 mg/ml, preferably wherein the concentration of preservative is or is less than about 0.035 mg/ml.

316. The aqueous pharmaceutical formulation of any one of statements 301 to 313, wherein the concentration of preservative is 0 mg/ml.

317. The aqueous pharmaceutical formulation of any one of statements 301 to 313, wherein the formulation does not comprise a preservative.

Preservative Identity

318. The aqueous pharmaceutical formulation of any one of statements 301 to 317, wherein the preservative is a sulfite, a paraben, benzyl alcohol, benzethonium chloride, propylene glycol, and/or creatinine 319. The aqueous pharmaceutical formulation of statement 318, wherein the sulfite is sodium sulfite (anhydrous), sodium bisulfite, and/or sodium metabisulfite.

320. The aqueous pharmaceutical formulation of statement 318, wherein the paraben is methylparaben, propylparaben, ethylparaben, butylparaben, isopropylparaben and/or isobutylparaben, preferably wherein the paraben is methylparaben and/or propylparaben.

Chelating Agent Concentration

321. The aqueous pharmaceutical formulation of any one of statements 301 to 321, wherein the formulation comprises one or more chelating agent, wherein the concentration of chelating agent is or is less than about 0.50 mg/ml.

322. The aqueous pharmaceutical formulation of statement 321, wherein the concentration of chelating agent is or is less than about 0.45 mg/ml, is or is less than about 0.40 mg/ml, is or is less than about 0.35 mg/ml, is or is less than about 0.30 mg/ml, is or is less than about 0.25 mg/ml, is or is less than about 0.20 mg/ml, is or is less than about 0.15 mg/ml, is or is less than about 0.10 mg/ml, is or is less than about 0.10 mg/ml, or is or is less than about 0.05 mg/ml.

323. The aqueous pharmaceutical formulation of any one of statements 301 to 321, wherein the concentration of chelating agent is 0 mg/ml.

324. The aqueous pharmaceutical formulation of any one of statements 301 to 321, wherein the formulation does not comprise a chelating agent.

Chelating Agent Identity

325. The aqueous pharmaceutical formulation of any one of statements 301 to 324, wherein the chelating agent is ethylenediaminetetraacetic acid (EDTA), sodium edetate, disodium edetate, tetrasodium edetate, calcium disodium edetate, calcium versetamide sodium, calteridol, and/or diethylenetriaminepenta acetic acid (DPTA).

326. The aqueous pharmaceutical formulation of statement 325, wherein the chelating agent is disodium edetate (disodium EDTA).

Glucocorticoid Identity

327. The aqueous pharmaceutical formulation of any one of statements 301 to 326, wherein the glucocorticoid is selected from the group consisting of dexamethasone, hydrocortisone, methylprednisolone, prednisone, prednisolone, prednylidene, cortisone, budesonide, betamethasone and beclomethasone.

328. The aqueous pharmaceutical formulation of statement 327, wherein the glucocorticoid comprises dexamethasone, optionally wherein the dexamethasone is selected from the group consisting of dexamethasone base, dexamethasone sodium phosphate, dexamethasone hemisuccinate, dexamethasone sodium succinate, dexamethasone succinate, and dexamethasone acetate.

329. The aqueous pharmaceutical formulation of statement 328, wherein the dexamethasone is dexamethasone sodium phosphate.

Glucocorticoid Concentration

330. The aqueous pharmaceutical formulation of any one of statements 301 to 329, wherein the concentration of glucocorticoid is or is at least about 25, 26, 27, 28, 29, 30, 31, 32, 33, 34, 35, 36, 37, 38, 39, 40, 41, 42, 43, 44, or 45 mg/ml.

331. The aqueous pharmaceutical formulation of statement 330, wherein the concentration of glucocorticoid is or is at least about 30 mg/ml.

332. The aqueous pharmaceutical formulation of statement 330, wherein the concentration of glucocorticoid is or is at least about 45 mg/ml.

Formulation pH

333. The aqueous pharmaceutical formulation of any one of statements 301 to 332, wherein the pH of the formulation is about 7.0 to about 8.2, about 7.2 to about 8.0, about 7.3 to about 7.9, or about 7.4 to about 7.8

334. The aqueous pharmaceutical formulation of statement 333, wherein the pH of the formulation is about 7.4 to about 7.8, preferably wherein the pH of the formulation is about 7.6.

Other Components of Formulation

335. The aqueous pharmaceutical formulation of any one of statements 301 to 334, wherein the formulation comprises a buffer.

336. The aqueous pharmaceutical formulation of statement 335, wherein the buffer is sodium citrate.

337. The aqueous pharmaceutical formulation of statement 335 or 336, wherein the concentration of buffer is about 10 mg/ml.

Container Type & Volume

338. The aqueous pharmaceutical formulation of any one of statements 301 to 337, wherein the container is a vial, ampoule, solvent reservoir, storage bottle, medical bottle, syringe, or bottle, preferably wherein the container is a vial, ampoule, or bottle.

339. The aqueous pharmaceutical formulation of any one of statements 301 to 338, wherein the volume of the container is or is at least about 1, 2, 3, 4, 5, 6, 7, 8, 9, 10, 15, 20, 25, 30, 35, 40, 45, 50, 51, 55, 60, 65, 70, 75, 80, 85, 90, 95, or 100 ml.

340. The aqueous pharmaceutical formulation of statement 339, wherein the volume of the container is or is at least about 51 ml.

341. The aqueous pharmaceutical formulation of any one of statements 301 to 340, wherein the volume of glucocorticoid packaged in the container is at least 1, 2, 3, 4, 5, 6, 7, 8, 9, 10, 15, 20, 25, 30, 35, 40, 45, 50, 55, 60, 65, 70, 75, 80, 85, 90, 95, or 100 ml.

Functional Features

342. The aqueous pharmaceutical formulation of any one of statements 301 to 341, wherein the shelf-life of the formulation is at least about 18, 24, 36, or 48 months when stored between 20° C. to 40° C. or between 15° C. to 20° C.

343. The aqueous pharmaceutical formulation of any one of statements 301 to 341, wherein the formulation remains stable when stored between 20° C. to 40° C. or between 15° C. to 20° C. for at least about 18, 24, 36, or 48 months.

344. The aqueous pharmaceutical formulation of any one of statements 301 to 343, wherein the formulation exhibits less than about 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0% degradation of the glucocorticoid when stored between 20° C. to 40° C. or between 15° C. to 20° C. for at least about 18, 24, 36, or 48 months.

345. The aqueous pharmaceutical formulation of any one of statements 301 to 343, wherein the amount of glucocorticoid in the formulation is maintained above about 95.0, 95.2, 95.4, 95.6, 96.0, 96.2, 96.4, 96.6, 96.8, 97.0, 97.2, 97.4, 97.6, 98.0, 98.2, 98.4, 98.6, 98.8, 99.0, 99.1, 99.2, 99.3, 99.4, 99.5, 99.6, 99.7, 99.8, or 99.9% as compared to the date of manufacture when the formulation is stored between 20° C. to 40° C. or between 15° C. to 20° C. for at least about 18, 24, 36, or 48 months.

346. The aqueous pharmaceutical formulation of any one of statements 301 to 343, wherein the amount of glucocorticoid in the formulation is maintained between ±1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% as compared to the date of manufacture when the formulation is stored between 20° C. to 40° C. or between 15° C. to 20° C. for at least about 18, 24, 36, or 48 months.

347. The aqueous pharmaceutical formulation of any one of statements 301 to 346, wherein the formulation exhibits less than ±0.1, 0.2, 0.3, 0.4, 0.5, 0.6, 0.7, 0.8, 0.9, 1.0, 1.2, 1.4, 1.6, 1.8, or 2.0 change in pH when stored between 20° C. to 40° C. or between 15° C. to 20° C. for at least about 18, 24, 36, or 48 months.

348. The aqueous pharmaceutical formulation of any one of statements 301 to 347, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity A when stored between 20° C. to 40° C. or between 15° C. to 20° C. for at least about 18, 24, 36, or 48 months.

349. The aqueous pharmaceutical formulation of any one of statements 301 to 348, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity B when stored between 20° C. to 40° C. or between 15° C. to 20° C. for at least about 18, 24, 36, or 48 months.

350. The aqueous pharmaceutical formulation of any one of statements 301 to 349, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity C when stored between 20° C. to 40° C. or between 15° C. to 20° C. for at least about 18, 24, 36, or 48 months.

351. The aqueous pharmaceutical formulation of any one of statements 301 to 350, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity D when stored between 20° C. to 40° C. or between 15° C. to 20° C. for at least about 18, 24, 36, or 48 months.

352. The aqueous pharmaceutical formulation of any one of statements 301 to 351, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity E when stored between 20° C. to 40° C. or between 15° C. to 20° C. for at least about 18, 24, 36, or 48 months.

353. The aqueous pharmaceutical formulation of any one of statements 301 to 352, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity F when stored between 20° C. to 40° C. or between 15° C. to 20° C. for at least about 18, 24, 36, or 48 months.

354. The aqueous pharmaceutical formulation of any one of statements 301 to 353, wherein the glucocorticoid is dexamethasone sodium phosphate, and wherein the formulation exhibits less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0% accumulation of impurity G when stored between 20° C. to 40° C. or between 15° C. to 20° C. for at least about 18, 24, 36, or 48 months.

355. The aqueous pharmaceutical formulation of any one of statements 301 to 354, wherein the formulation exhibits less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19 0.20, 0.21, 0.22, 0.23, 0.24, 0.25, 0.26, 0.27, 0.28, 0.29, or 3.0% accumulation of unspecified impurities when stored between 20° C. to 40° C. or between 15° C. to 20° C. for at least about 18, 24, 36, or 48 months.

356. The aqueous pharmaceutical formulation of any one of statements 301 to 355, wherein the formulation exhibits less than about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0% accumulation of total impurities when stored between 20° C. to 40° C. or between 15° C. to 20° C. for at least about 18, 24, 36, or 48 months.

Medical Use

357. The aqueous pharmaceutical formulation of any one of statements 301 to 356, for use in a method of treatment.

358. Use of the aqueous pharmaceutical formulation of any one of statements 301 to 356 for the preparation of a medicament for use in a method of treatment.

359. A method of treatment comprising administering to a subject in need thereof, a therapeutically effective amount of the aqueous pharmaceutical formulation of any one of statements 301 to 356.

360. The formulation for use, use, or method of any one of statements 357 to 359, wherein the method is a method of reducing stem cell accumulation in the spleen in a subject, the method comprising administering the formulation to the subject prior to stem cell treatment.

361. The formulation for use, use, or method of any one of statements 357 to 359, wherein the method is a method of enhancing adoptive cellular therapy (ACT) in a subject, the method comprising administering the formulation to the subject prior to adoptive cellular therapy.

362. The formulation for use, use, or method of any one of statements 357 to 359, wherein the method is a method of treatment of a lymphocyte mediated disease in a subject, the method comprising administering the formulation to the subject.

Method of Manufacture

363. A method for stabilising an aqueous pharmaceutical formulation comprising a glucocorticoid, the method comprising packaging the aqueous pharmaceutical formulation of any one of statements 301 to 356 into a container with a headspace volume (ml) to total glucocorticoid content (mg) ratio of 0.007 or less.

The invention claimed is:

1. A clear aqueous pharmaceutical formulation comprising a concentration of at least 24 mg/ml of dexamethasone sodium phosphate or dexamethasone phosphate and a concentration of equal to or less than 0.035 mg/ml of a preservative, wherein the formulation is packaged in a container with a headspace volume (ml) to dexamethasone content (mg) ratio of 0.0065 or less, wherein the amount of dexamethasone in the formulation is maintained between ±5% as compared to the date of manufacture when the formulation is stored between 2° C. to 40° C. for at least about 18, 24, 36, or 48 months, wherein the formulation is for intravenous administration, and wherein the volume of the container is at least about 45, 50, 51, 55, 60, 65, 70, 75, 80, 85, 90, 95, or 100 ml.

2. The aqueous pharmaceutical formulation of claim 1, wherein the headspace volume (ml) to dexamethasone sodium phosphate or dexamethasone phosphate content (mg) ratio is 0.00588 or less.

3. The aqueous pharmaceutical formulation of claim 1, wherein the headspace volume comprises less than about 21% oxygen, less than about 10% oxygen, or less than about 5% oxygen.

4. The aqueous pharmaceutical formulation of claim 1, wherein the preservative is a sulfite, a paraben, benzyl alcohol, propylene glycol, and/or creatinine.

5. The aqueous pharmaceutical formulation of claim 4, wherein the sulfite is sodium sulfite (anhydrous), sodium bisulfite, and/or sodium metabisulfite.

6. The aqueous pharmaceutical formulation of claim 1, wherein the formulation does not comprise a preservative.

7. The aqueous pharmaceutical formulation of claim 1, wherein the formulation comprises one or more chelating agent, wherein the concentration of chelating agent is or is less than about 0.50 mg/ml.

8. The aqueous pharmaceutical formulation of claim 7, wherein the chelating agent is disodium edetate (disodium EDTA).

9. The aqueous pharmaceutical formulation of claim 1, wherein the formulation does not comprise a chelating agent.

10. The aqueous pharmaceutical formulation of claim 1, wherein the formulation comprises dexamethasone sodium phosphate.

11. The aqueous pharmaceutical formulation of claim 1, wherein the shelf-life of the formulation is at least about 18, 24, 36, or 48 months when stored between 2° C. to 40° C.

12. The aqueous pharmaceutical formulation of claim 1, wherein the formulation exhibits less than ±0.5 change in pH when stored between 2° C. to 40° C. for at least about 18, 24, 36, or 48 months.

13. The aqueous pharmaceutical formulation of claim 1, wherein the formulation exhibits less than about 0.50% accumulation of impurity A when stored between 2° C. to 40° C. for at least about 18, 24, 36, or 48 months.

14. The aqueous pharmaceutical formulation of claim 1, wherein the formulation exhibits less than about 0.50% accumulation of impurity B when stored between 2° C. to 40° C. for at least about 18, 24, 36, or 48 months.

15. The aqueous pharmaceutical formulation of claim 1, wherein the formulation exhibits less than about 0.50% accumulation of impurity G when stored between 2° C. to 40° C. for at least about 18, 24, 36, or 48 months.

16. The aqueous pharmaceutical formulation of claim 1, wherein the formulation exhibits less than about 0.20% accumulation of unspecified impurities when stored between 2° C. to 40° C. for at least about 18, 24, 36, or 48 months.

17. The aqueous pharmaceutical formulation of claim 1, wherein the formulation exhibits less than about 3.0% accumulation of total impurities when stored between 2° C. to 40° C. for at least about 18, 24, 36, or 48 months.

* * * * *